US007264809B1

(12) United States Patent  
Gayle, III et al.

(10) Patent No.: US 7,264,809 B1
(45) Date of Patent: Sep. 4, 2007

(54) METHODS OF INHIBITING PLATELET ACTIVATION AND RECRUITMENT

(75) Inventors: Richard B. Gayle, III, Woodinville, WA (US); Aaron J. Marcus, Scarsdale, NY (US); Charles R. Maliszewski, Seattle, WA (US)

(73) Assignees: Immunex Corporation, Seattle, WA (US); Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/807,660

(22) PCT Filed: Oct. 13, 1999

(86) PCT No.: PCT/US99/23641

§ 371 (c)(1), (2), (4) Date: Sep. 6, 2001

(87) PCT Pub. No.: WO00/23094

PCT Pub. Date: Apr. 27, 2000

Related U.S. Application Data

(60) Provisional application No. 60/149,010, filed on Aug. 13, 1999, provisional application No. 60/107,466, filed on Nov. 6, 1998, provisional application No. 60/104,585, filed on Oct. 16, 1998.

(51) Int. Cl.
*A61K 39/00* (2006.01)
*C12P 21/02* (2006.01)
*C12N 9/00* (2006.01)

(52) U.S. Cl. .............................. 424/183.1; 424/192.1; 435/69.1; 435/69.2; 435/183

(58) Field of Classification Search ................ 530/300; 435/183; 424/192.1
See application file for complete search history.

(56) References Cited

U.S. PATENT DOCUMENTS

| 5,073,627 A | 12/1991 | Curtis et al. |
| 5,378,601 A | 1/1995 | Gepner-Puszkin |
| 5,506,126 A | 4/1996 | Seed et al. |
| 5,741,771 A * | 4/1998 | Dawson et al. |
| 5,798,241 A | 8/1998 | Beaudoin et al. |
| 6,287,837 B1 | 9/2001 | Beaudoin et al. |
| 6,867,177 B2 | 3/2005 | Pinsky |

FOREIGN PATENT DOCUMENTS

| EP | 0416673 | 3/1991 |
| WO | WO96/30532 | 10/1996 |
| WO | WO96/32471 | 10/1996 |
| WO | WO 00/23459 | 4/2000 |
| WO | WO 01/11949 | 2/2001 |

OTHER PUBLICATIONS

Gayle et al, J Clin Invest 101(9): 1851-1859, May 1998.*
Ngo et al., in The Protein Folding Problem and Tertiary Structure Prediction, 1994, Merz, et al., (ed.), Birkhauser, Boston, MA, pp. 492-495.*
Skolnick et al., From genes to protein structure and function: novel applications of computational approaches in the genomic era, Jan. 2000, Trends in Biotech. 18(1): 34-39.*
Mikayama et al, Proc. Natl. Acad. Sci, USA vol. 90: 10056-10060, Nov. 1993.*
Grinthal et al, Biochemistry 41: 1947-56, 2002.*
Attwood et al, The Babel of Bioinformatics, 2000, Science vol. 290 No. 5491: 471-473.*
Chadwick and Frischauf, *Genomics* 50:357, 1998.
Choudhri, et al., *J. Clin. Invest.* 102:1301, 1998.
Colman et al., *Blood* 68:565, 1986.
Connolly, *J. Clin. Invest.* 97:209, 1996.
Connolly, *Neurosurg.* 38(3):523, 1996.
* Cullen, DNA 7(9):645, 1998.
Gayle III, et al., *J. Clin. Invest.* 101(9):1851, 1998.
Handa and Guidotti, *Biochem. Biophys. Res. Commun.* 218:916, 1996.
Kaczmarek et al., *J. Biol. Chem.* 271:33116, 1996.
Kansas and Tedder, *J. Immunol.* 147:4094, 1991.
Maliszewski et al., *J. Immunol.* 153:3574, 1994.
Marcus and Safier, *FASEB J* 7:516, 1993.
Marcus et al., *Clin. Res.* 40:226A (abstract), 1992.
Marcus et al., *J. Clin. Invest.*, 88:1690, 1991.
* Marcus et al., *J. Clin. Invest.* 99:1351, 1997.
Mulero et al., *J. Biol. Chem.* 274(29):20064, 1999.
Plesner, Int. Rev. Cytol. 158:141, 1995.
Rector et al., *Immunology* 55:481, 1985.
Ronaghi et al., *Science* 281:336, 1998.
Schoenborn, et al., *Cytogen Cell Gen.* 81(3-4):287, 1998.
Sevigny et al., *Biochem. Biophys. Acta* 1334:73, 1997.
Sevigny et al., *Biochem. J.*, 312:351, 1995.
Wang and Guidotti, *J. Biol. Chem.* 271:9898, 1996.
Wang et al., *J. Biol. Chem.* 273:24814, 1998.

* cited by examiner

*Primary Examiner*—Christina Chan
*Assistant Examiner*—Phuong Huynh
(74) *Attorney, Agent, or Firm*—Synnestvedt & Lechner LLP

(57) ABSTRACT

The present invention provides soluble CD39 polypeptides and compositions, and methods for inhibiting platelet activation and recruitment in a mammal comprising administering a soluble CD39 polypeptide.

27 Claims, 24 Drawing Sheets

```
Met Glu Asp Thr Lys Glu Ser Asn Val Lys Thr Phe Cys Ser Lys Asn Ile Leu Ala    19
Ile Leu Gly Phe Ser Ser Ile Ile Ala Val Ile Ala Leu Leu Ala Val Gly Leu Thr    38
Gln Asn Lys Ala Leu Pro Glu Asn Val Lys Tyr Gly Ile Val Leu Asp Ala Gly Ser    57
Ser His Thr Ser Leu Tyr Ile Tyr Lys Trp Pro Ala Glu Lys Glu Asn Asp Thr Gly    76
Val Val His Gln Val Glu Glu Cys Arg Val Lys Gly Pro Gly Ile Ser Lys Phe Val    95
Gln Lys Val Asn Glu Ile Gly Ile Tyr Leu Thr Asp Cys Met Glu Arg Ala Arg Glu   114
Val Ile Pro Arg Ser Gln His Gln Glu Thr Pro Val Tyr Leu Gly Ala Thr Ala Gly   133
Met Arg Leu Leu Arg Met Glu Ser Glu Glu Leu Ala Asp Arg Val Leu Asp Val Val   152
Glu Arg Ser Leu Ser Asn Tyr Pro Phe Asp Phe Gln Gly Ala Arg Ile Ile Thr Gly   171
Gln Glu Glu Gly Ala Tyr Gly Trp Ile Thr Ile Asn Tyr Leu Leu Gly Lys Phe Ser   190
Gln Lys Thr Arg Trp Phe Ser Ile Val Pro Tyr Glu Thr Asn Asn Gln Glu Thr Phe   209
Gly Ala Leu Asp Leu Gly Gly Ala Ser Thr Gln Val Thr Phe Val Pro Gln Asn Gln   228
Thr Ile Glu Ser Pro Asp Asn Ala Leu Gln Phe Arg Leu Tyr Gly Lys Asp Tyr Asn   247
Val Tyr Thr His Ser Phe Leu Cys Tyr Gly Lys Asp Gln Ala Leu Trp Gln Lys Leu   266
Ala Lys Asp Ile Gln Val Ala Ser Asn Glu Ile Leu Arg Asp Pro Cys Phe His Pro   285
Gly Tyr Lys Lys Val Val Asn Val Ser Asp Leu Tyr Lys Thr Pro Cys Thr Lys Arg   304
Phe Glu Met Thr Leu Pro Phe Gln Gln Phe Glu Ile Gln Gly Ile Gly Asn Tyr Gln   323
Gln Cys His Gln Ser Ile Leu Glu Leu Phe Asn Thr Ser Tyr Cys Pro Tyr Ser Gln   342
Cys Ala Phe Asn Gly Ile Phe Leu Pro Pro Leu Gln Gly Asp Phe Gly Ala Phe Ser   361
Ala Phe Tyr Phe Val Met Lys Phe Leu Asn Leu Thr Ser Glu Lys Val Ser Gln Glu   380
Lys Val Thr Glu Met Met Lys Lys Phe Cys Ala Gln Pro Trp Glu Glu Ile Lys Thr   399
Ser Tyr Ala Gly Val Lys Glu Lys Tyr Leu Ser Glu Tyr Cys Phe Ser Gly Thr Tyr   418
Ile Leu Ser Leu Leu Leu Gln Gly Tyr His Phe Thr Ala Asp Ser Trp Glu His Ile   437
His Phe Ile Gly Lys Ile Gln Gly Ser Asp Ala Gly Trp Thr Leu Gly Tyr Met Leu   456
Asn Leu Thr Asn Met Ile Pro Ala Glu Gln Pro Leu Ser Thr Pro Leu Ser His Ser   475
Thr Tyr Val Phe Leu Met Val Leu Phe Ser Leu Val Leu Phe Thr Val Ala Ile Ile   494
Gly Leu Leu Ile Phe His Lys Pro Ser Tyr Phe Trp Lys Asp Met Val                510
```

*Fig. 1*

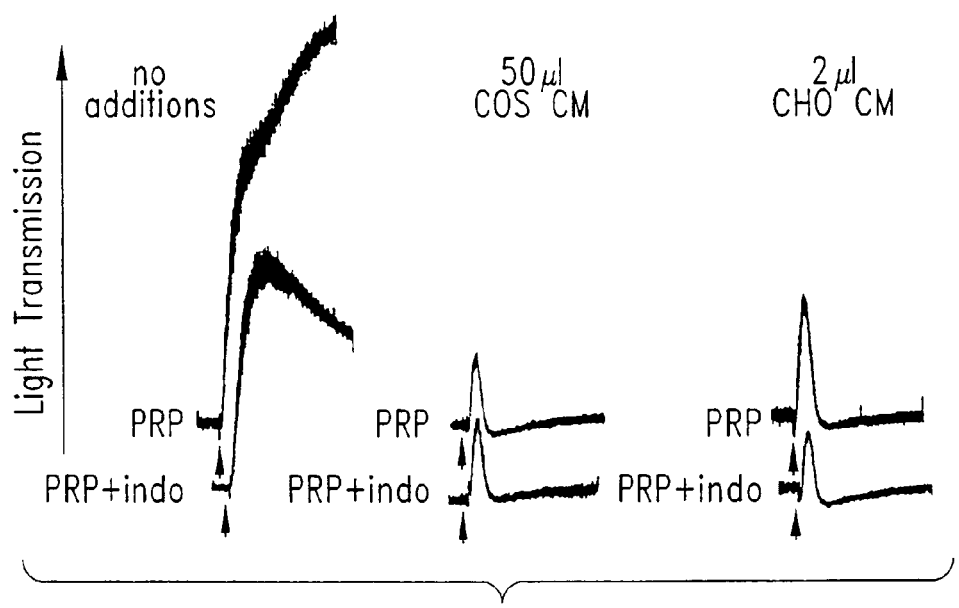
*Fig. 8A*
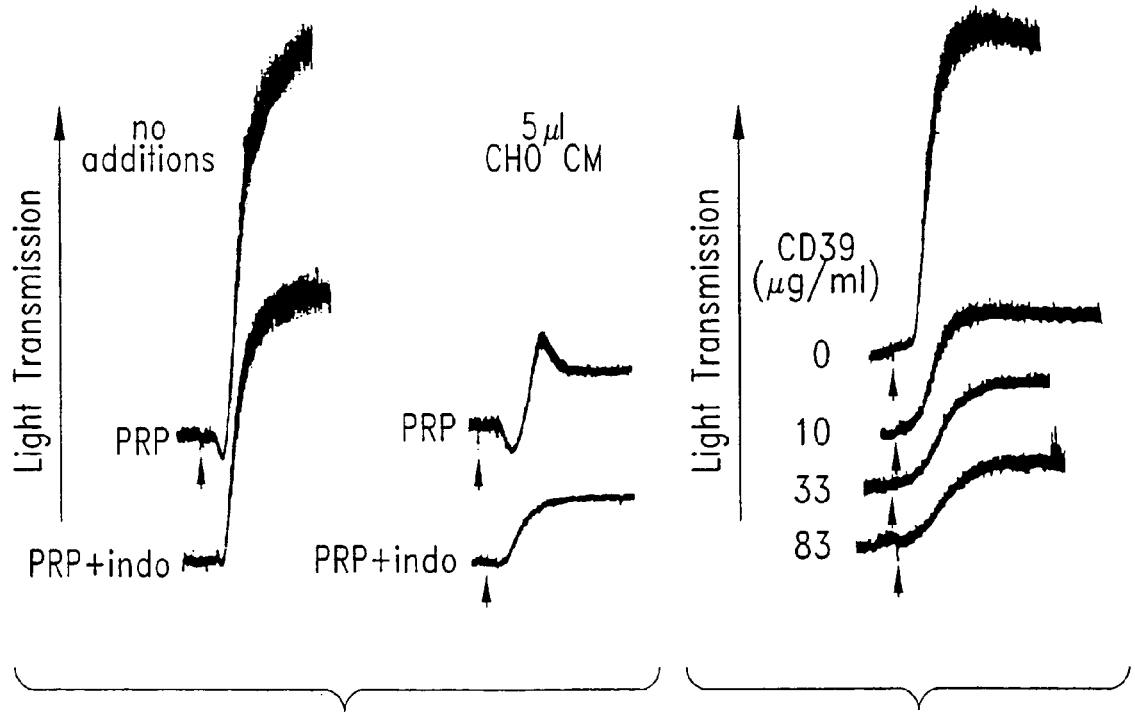
*Fig. 8B*  *Fig. 8C*

Human CD39 (amino acids 1-69 of SEQ ID NO:2)
    MEDTKESNVK TFCSKNILAI LGFSSIIAVI ALLAVGLTQN KALPENVKYG IVLDAGSS...
    |                                                   || | ||||
    MATSWGTVFF MLVVSCVCSA VSHRNQQTWF EGIFLSSMCP INVSASTLYG IMFDAGST...
Human CD39-L4 (SEQ ID NO:31)

SEQUENCE LISTING

<160> NUMBER OF SEQ ID NOS: 37

<210> SEQ ID NO 1
<211> LENGTH: 1599
<212> TYPE: DNA
<213> ORGANISM: Homo sapiens
<220> FEATURE:
<221> NAME/KEY: CDS
<222> LOCATION: (67)..(1596)

<400> SEQUENCE: 1

```
ccacaccaag cagcggctgg gggggggaaa gacgaggaaa gaggaggaaa acaaaagctg      60 ctactt atg gaa gat aca aag gag tct aac gtg aag aca ttt tgc tcc        108
       Met Glu Asp Thr Lys Glu Ser Asn Val Lys Thr Phe Cys Ser
       1               5                  10 aag aat atc cta gcc atc ctt ggc ttc tcc tct atc ata gct gtg ata       156
Lys Asn Ile Leu Ala Ile Leu Gly Phe Ser Ser Ile Ile Ala Val Ile
 15              20                  25                  30 gct ttg ctt gct gtg ggg ttg acc cag aac aaa gca ttg cca gaa aac       204
Ala Leu Leu Ala Val Gly Leu Thr Gln Asn Lys Ala Leu Pro Glu Asn
                 35                  40                  45 gtt aag tat ggg att gtg ctg gat gcg ggt tct tct cac aca agt tta       252
Val Lys Tyr Gly Ile Val Leu Asp Ala Gly Ser Ser His Thr Ser Leu
             50                  55                  60 tac atc tat aag tgg cca gca gaa aag gag aat gac aca ggc gtg gtg       300
Tyr Ile Tyr Lys Trp Pro Ala Glu Lys Glu Asn Asp Thr Gly Val Val
         65                  70                  75 cat caa gta gaa gaa tgc agg gtt aaa ggt cct gga atc tca aaa ttt       348
His Gln Val Glu Glu Cys Arg Val Lys Gly Pro Gly Ile Ser Lys Phe
     80                  85                  90 gtt cag aaa gta aat gaa ata ggc att tac ctg act gat tgc atg gaa       396
Val Gln Lys Val Asn Glu Ile Gly Ile Tyr Leu Thr Asp Cys Met Glu
 95                 100                 105                 110 aga gct agg gaa gtg att cca agg tcc cag cac caa gag aca ccc gtt       444
Arg Ala Arg Glu Val Ile Pro Arg Ser Gln His Gln Glu Thr Pro Val
                115                 120                 125 tac ctg gga gcc acg gca ggc atg cgg ttg ctc agg atg gaa agt gaa       492
Tyr Leu Gly Ala Thr Ala Gly Met Arg Leu Leu Arg Met Glu Ser Glu
            130                 135                 140 gag ttg gca gac agg gtt ctg gat gtg gtg gag agg agc ctc agc aac       540
Glu Leu Ala Asp Arg Val Leu Asp Val Val Glu Arg Ser Leu Ser Asn
        145                 150                 155 tac ccc ttt gac ttc cag ggt gcc agg atc att act ggc caa gag gaa       588
Tyr Pro Phe Asp Phe Gln Gly Ala Arg Ile Ile Thr Gly Gln Glu Glu
    160                 165                 170 ggt gcc tat ggc tgg att act atc aac tat ctg ctg ggc aaa ttc agt       636
Gly Ala Tyr Gly Trp Ile Thr Ile Asn Tyr Leu Leu Gly Lys Phe Ser
175                 180                 185                 190 cag aaa aca agg tgg ttc agc ata gtc cca tat gaa acc aat aat cag       684
Gln Lys Thr Arg Trp Phe Ser Ile Val Pro Tyr Glu Thr Asn Asn Gln
                195                 200                 205 gaa acc ttt gga gct ttg gac ctt ggg gga gcc tct aca caa gtc act       732
Glu Thr Phe Gly Ala Leu Asp Leu Gly Gly Ala Ser Thr Gln Val Thr
            210                 215                 220
```

```
ttt gta ccc caa aac cag act atc gag tcc cca gat aat gct ctg caa        780
Phe Val Pro Gln Asn Gln Thr Ile Glu Ser Pro Asp Asn Ala Leu Gln
        225                 230                 235 ttt cgc ctc tat ggc aag gac tac aat gtc tac aca cat agc ttc ttg        828
Phe Arg Leu Tyr Gly Lys Asp Tyr Asn Val Tyr Thr His Ser Phe Leu
240                 245                 250 tgc tat ggg aag gat cag gca ctc tgg cag aaa ctg gcc aag gac att        876
Cys Tyr Gly Lys Asp Gln Ala Leu Trp Gln Lys Leu Ala Lys Asp Ile
255                 260                 265                 270 cag gtt gca agt aat gaa att ctc agg gac cca tgc ttt cat cct gga        924
Gln Val Ala Ser Asn Glu Ile Leu Arg Asp Pro Cys Phe His Pro Gly
                275                 280                 285 tat aag aag gta gtg aac gta agt gac ctt tac aag acc ccc tgc acc        972
Tyr Lys Lys Val Val Asn Val Ser Asp Leu Tyr Lys Thr Pro Cys Thr
        290                 295                 300 aag aga ttt gag atg act ctt cca ttc cag cag ttt gaa atc cag ggt       1020
Lys Arg Phe Glu Met Thr Leu Pro Phe Gln Gln Phe Glu Ile Gln Gly
        305                 310                 315 att gga aac tat caa caa tgc cat caa agc atc ctg gag ctc ttc aac       1068
Ile Gly Asn Tyr Gln Gln Cys His Gln Ser Ile Leu Glu Leu Phe Asn
320                 325                 330 acc agt tac tgc cct tac tcc cag tgt gcc ttc aat ggg att ttc ttg       1116
Thr Ser Tyr Cys Pro Tyr Ser Gln Cys Ala Phe Asn Gly Ile Phe Leu
335                 340                 345                 350 cca cca ctc cag ggg gat ttt ggg gca ttt tca gct ttt tac ttt gtg       1164
Pro Pro Leu Gln Gly Asp Phe Gly Ala Phe Ser Ala Phe Tyr Phe Val
                355                 360                 365 atg aag ttt tta aac ttg aca tca gag aaa gtc tct cag gaa aag gtg       1212
Met Lys Phe Leu Asn Leu Thr Ser Glu Lys Val Ser Gln Glu Lys Val
        370                 375                 380 act gag atg atg aaa aag ttc tgt gct cag cct tgg gag gag ata aaa       1260
Thr Glu Met Met Lys Lys Phe Cys Ala Gln Pro Trp Glu Glu Ile Lys
        385                 390                 395 aca tct tac gct gga gta aag gag aag tac ctg agt gaa tac tgc ttt       1308
Thr Ser Tyr Ala Gly Val Lys Glu Lys Tyr Leu Ser Glu Tyr Cys Phe
400                 405                 410 tct ggt acc tac att ctc tcc ctc ctt ctg caa ggc tat cat ttc aca       1356
Ser Gly Thr Tyr Ile Leu Ser Leu Leu Leu Gln Gly Tyr His Phe Thr
415                 420                 425                 430 gct gat tcc tgg gag cac atc cat ttc att ggc aag atc cag ggc agc       1404
Ala Asp Ser Trp Glu His Ile His Phe Ile Gly Lys Ile Gln Gly Ser
                435                 440                 445 gac gcc ggc tgg act ttg ggc tac atg ctg aac ctg acc aac atg atc       1452
Asp Ala Gly Trp Thr Leu Gly Tyr Met Leu Asn Leu Thr Asn Met Ile
        450                 455                 460 cca gct gag caa cca ttg tcc aca cct ctc tcc cac tcc acc tat gtc       1500
Pro Ala Glu Gln Pro Leu Ser Thr Pro Leu Ser His Ser Thr Tyr Val
        465                 470                 475 ttc ctc atg gtt cta ttc tcc ctg gtc ctt ttc aca gtg gcc atc ata       1548
Phe Leu Met Val Leu Phe Ser Leu Val Leu Phe Thr Val Ala Ile Ile
480                 485                 490 ggc ttg ctt atc ttt cac aag cct tca tat ttc tgg aaa gat atg gta       1596
Gly Leu Leu Ile Phe His Lys Pro Ser Tyr Phe Trp Lys Asp Met Val
495                 500                 505                 510 tag                                                                    1599

<210> SEQ ID NO 2
<211> LENGTH: 510
<212> TYPE: PRT
```

<213> ORGANISM: Homo sapiens

<400> SEQUENCE: 2

```
Met Glu Asp Thr Lys Glu Ser Asn Val Lys Thr Phe Cys Ser Lys Asn
 1               5                  10                  15

Ile Leu Ala Ile Leu Gly Phe Ser Ser Ile Ala Val Ile Ala Leu
             20                  25                  30

Leu Ala Val Gly Leu Thr Gln Asn Lys Ala Leu Pro Glu Asn Val Lys
             35                  40                  45

Tyr Gly Ile Val Leu Asp Ala Gly Ser Ser His Thr Ser Leu Tyr Ile
         50                  55                  60

Tyr Lys Trp Pro Ala Glu Lys Glu Asn Asp Thr Gly Val Val His Gln
 65                  70                  75                  80

Val Glu Glu Cys Arg Val Lys Gly Pro Gly Ile Ser Lys Phe Val Gln
                 85                  90                  95

Lys Val Asn Glu Ile Gly Ile Tyr Leu Thr Asp Cys Met Glu Arg Ala
            100                 105                 110

Arg Glu Val Ile Pro Arg Ser Gln His Gln Glu Thr Pro Val Tyr Leu
            115                 120                 125

Gly Ala Thr Ala Gly Met Arg Leu Leu Arg Met Glu Ser Glu Glu Leu
        130                 135                 140

Ala Asp Arg Val Leu Asp Val Val Glu Arg Ser Leu Ser Asn Tyr Pro
145                 150                 155                 160

Phe Asp Phe Gln Gly Ala Arg Ile Ile Thr Gly Gln Glu Glu Gly Ala
                165                 170                 175

Tyr Gly Trp Ile Thr Ile Asn Tyr Leu Leu Gly Lys Phe Ser Gln Lys
            180                 185                 190

Thr Arg Trp Phe Ser Ile Val Pro Tyr Glu Thr Asn Asn Gln Glu Thr
        195                 200                 205

Phe Gly Ala Leu Asp Leu Gly Gly Ala Ser Thr Gln Val Thr Phe Val
    210                 215                 220

Pro Gln Asn Gln Thr Ile Glu Ser Pro Asp Asn Ala Leu Gln Phe Arg
225                 230                 235                 240

Leu Tyr Gly Lys Asp Tyr Asn Val Tyr Thr His Ser Phe Leu Cys Tyr
                245                 250                 255

Gly Lys Asp Gln Ala Leu Trp Gln Lys Leu Ala Lys Asp Ile Gln Val
            260                 265                 270

Ala Ser Asn Glu Ile Leu Arg Asp Pro Cys Phe His Pro Gly Tyr Lys
        275                 280                 285

Lys Val Val Asn Val Ser Asp Leu Tyr Lys Thr Pro Cys Thr Lys Arg
    290                 295                 300

Phe Glu Met Thr Leu Pro Phe Gln Gln Phe Glu Ile Gln Gly Ile Gly
305                 310                 315                 320

Asn Tyr Gln Gln Cys His Gln Ser Ile Leu Glu Leu Phe Asn Thr Ser
                325                 330                 335

Tyr Cys Pro Tyr Ser Gln Cys Ala Phe Asn Gly Ile Phe Leu Pro Pro
            340                 345                 350

Leu Gln Gly Asp Phe Gly Ala Phe Ser Ala Phe Tyr Phe Val Met Lys
        355                 360                 365

Phe Leu Asn Leu Thr Ser Glu Lys Val Ser Gln Glu Lys Val Thr Glu
    370                 375                 380

Met Met Lys Lys Phe Cys Ala Gln Pro Trp Glu Glu Ile Lys Thr Ser
385                 390                 395                 400
```

```
Tyr Ala Gly Val Lys Glu Lys Tyr Leu Ser Glu Tyr Cys Phe Ser Gly
            405                 410                 415

Thr Tyr Ile Leu Ser Leu Leu Leu Gln Gly Tyr His Phe Thr Ala Asp
            420                 425                 430

Ser Trp Glu His Ile His Phe Ile Gly Lys Ile Gln Gly Ser Asp Ala
            435                 440                 445

Gly Trp Thr Leu Gly Tyr Met Leu Asn Leu Thr Asn Met Ile Pro Ala
450                 455                 460

Glu Gln Pro Leu Ser Thr Pro Leu Ser His Ser Thr Tyr Val Phe Leu
465                 470                 475                 480

Met Val Leu Phe Ser Leu Val Leu Phe Thr Val Ala Ile Ile Gly Leu
                485                 490                 495

Leu Ile Phe His Lys Pro Ser Tyr Phe Trp Lys Asp Met Val
                500                 505                 510

<210> SEQ ID NO 3
<211> LENGTH: 476
<212> TYPE: PRT
<213> ORGANISM: Artificial Sequence
<220> FEATURE:
<223> OTHER INFORMATION: Description of Artificial Sequence:  Fusion
      construct of human CD39

<400> SEQUENCE: 3

Met Ala Thr Ser Trp Gly Thr Val Phe Phe Met Leu Val Val Ser Cys
1               5                   10                  15

Val Cys Ser Ala Val Ser His Arg Asn Gln Gln Thr Trp Phe Glu Gly
            20                  25                  30

Ile Phe Leu Ser Ser Thr Gln Asn Lys Ala Leu Pro Glu Asn Val Lys
        35                  40                  45

Tyr Gly Ile Val Leu Asp Ala Gly Ser Ser His Thr Ser Leu Tyr Ile
    50                  55                  60

Tyr Lys Trp Pro Ala Glu Lys Glu Asn Asp Thr Gly Val Val His Gln
65                  70                  75                  80

Val Glu Glu Cys Arg Val Lys Gly Pro Gly Ile Ser Lys Phe Val Gln
                85                  90                  95

Lys Val Asn Glu Ile Gly Ile Tyr Leu Thr Asp Cys Met Glu Arg Ala
            100                 105                 110

Arg Glu Val Ile Pro Arg Ser Gln His Gln Glu Thr Pro Val Tyr Leu
        115                 120                 125

Gly Ala Thr Ala Gly Met Arg Leu Leu Arg Met Glu Ser Glu Glu Leu
    130                 135                 140

Ala Asp Arg Val Leu Asp Val Val Glu Arg Ser Leu Ser Asn Tyr Pro
145                 150                 155                 160

Phe Asp Phe Gln Gly Ala Arg Ile Ile Thr Gly Gln Glu Glu Gly Ala
                165                 170                 175

Tyr Gly Trp Ile Thr Ile Asn Tyr Leu Leu Gly Lys Phe Ser Gln Lys
            180                 185                 190

Thr Arg Trp Phe Ser Ile Val Pro Tyr Glu Thr Asn Asn Gln Glu Thr
        195                 200                 205

Phe Gly Ala Leu Asp Leu Gly Gly Ala Ser Thr Gln Val Thr Phe Val
    210                 215                 220

Pro Gln Asn Gln Thr Ile Glu Ser Pro Asp Asn Ala Leu Gln Phe Arg
225                 230                 235                 240

Leu Tyr Gly Lys Asp Tyr Asn Val Tyr Thr His Ser Phe Leu Cys Tyr
                245                 250                 255
```

```
Gly Lys Asp Gln Ala Leu Trp Gln Lys Leu Ala Lys Asp Ile Gln Val
            260                 265                 270

Ala Ser Asn Glu Ile Leu Arg Asp Pro Cys Phe His Pro Gly Tyr Lys
            275                 280                 285

Lys Val Val Asn Val Ser Asp Leu Tyr Lys Thr Pro Cys Thr Lys Arg
            290                 295                 300

Phe Glu Met Thr Leu Pro Phe Gln Gln Phe Glu Ile Gln Gly Ile Gly
305                 310                 315                 320

Asn Tyr Gln Gln Cys His Gln Ser Ile Leu Glu Leu Phe Asn Thr Ser
                325                 330                 335

Tyr Cys Pro Tyr Ser Gln Cys Ala Phe Asn Gly Ile Phe Leu Pro Pro
                340                 345                 350

Leu Gln Gly Asp Phe Gly Ala Phe Ser Ala Phe Tyr Phe Val Met Lys
                355                 360                 365

Phe Leu Asn Leu Thr Ser Glu Lys Val Ser Gln Glu Lys Val Thr Glu
            370                 375                 380

Met Met Lys Lys Phe Cys Ala Gln Pro Trp Glu Glu Ile Lys Thr Ser
385                 390                 395                 400

Tyr Ala Gly Val Lys Glu Lys Tyr Leu Ser Glu Tyr Cys Phe Ser Gly
                405                 410                 415

Thr Tyr Ile Leu Ser Leu Leu Leu Gln Gly Tyr His Phe Thr Ala Asp
                420                 425                 430

Ser Trp Glu His Ile His Phe Ile Gly Lys Ile Gln Gly Ser Asp Ala
            435                 440                 445

Gly Trp Thr Leu Gly Tyr Met Leu Asn Leu Thr Asn Met Ile Pro Ala
450                 455                 460

Glu Gln Pro Leu Ser Thr Pro Leu Ser His Ser Thr
465                 470                 475

<210> SEQ ID NO 4
<211> LENGTH: 476
<212> TYPE: PRT
<213> ORGANISM: Artificial Sequence
<220> FEATURE:
<223> OTHER INFORMATION: Description of Artificial Sequence: Fusion
      construct of human CD39
<220> FEATURE:
<221> NAME/KEY: VARIANT
<222> LOCATION: (39)
<223> OTHER INFORMATION: Any amino acid, preferably Cys or Ser

<400> SEQUENCE: 4

Met Ala Thr Ser Trp Gly Thr Val Phe Phe Met Leu Val Val Ser Cys
1               5                   10                  15

Val Cys Ser Ala Val Ser His Arg Asn Gln Gln Thr Trp Phe Glu Gly
                20                  25                  30

Ile Phe Leu Ser Ser Met Xaa Pro Ile Asn Val Ser Ala Ser Thr Leu
            35                  40                  45

Tyr Gly Ile Val Leu Asp Ala Gly Ser Ser His Thr Ser Leu Tyr Ile
        50                  55                  60

Tyr Lys Trp Pro Ala Glu Lys Glu Asn Asp Thr Gly Val Val His Gln
65                  70                  75                  80

Val Glu Glu Cys Arg Val Lys Gly Pro Gly Ile Ser Lys Phe Val Gln
                85                  90                  95

Lys Val Asn Glu Ile Gly Ile Tyr Leu Thr Asp Cys Met Glu Arg Ala
            100                 105                 110
```

```
Arg Glu Val Ile Pro Arg Ser Gln His Gln Glu Thr Pro Val Tyr Leu
        115                 120                 125
Gly Ala Thr Ala Gly Met Arg Leu Leu Arg Met Glu Ser Glu Glu Leu
130                 135                 140
Ala Asp Arg Val Leu Asp Val Val Glu Arg Ser Leu Ser Asn Tyr Pro
145                 150                 155                 160
Phe Asp Phe Gln Gly Ala Arg Ile Ile Thr Gly Gln Glu Glu Gly Ala
                165                 170                 175
Tyr Gly Trp Ile Thr Ile Asn Tyr Leu Leu Gly Lys Phe Ser Gln Lys
            180                 185                 190
Thr Arg Trp Phe Ser Ile Val Pro Tyr Glu Thr Asn Asn Gln Glu Thr
        195                 200                 205
Phe Gly Ala Leu Asp Leu Gly Gly Ala Ser Thr Gln Val Thr Phe Val
    210                 215                 220
Pro Gln Asn Gln Thr Ile Glu Ser Pro Asp Asn Ala Leu Gln Phe Arg
225                 230                 235                 240
Leu Tyr Gly Lys Asp Tyr Asn Val Tyr Thr His Ser Phe Leu Cys Tyr
                245                 250                 255
Gly Lys Asp Gln Ala Leu Trp Gln Lys Leu Ala Lys Asp Ile Gln Val
            260                 265                 270
Ala Ser Asn Glu Ile Leu Arg Asp Pro Cys Phe His Pro Gly Tyr Lys
        275                 280                 285
Lys Val Val Asn Val Ser Asp Leu Tyr Lys Thr Pro Cys Thr Lys Arg
    290                 295                 300
Phe Glu Met Thr Leu Pro Phe Gln Gln Phe Glu Ile Gln Gly Ile Gly
305                 310                 315                 320
Asn Tyr Gln Gln Cys His Gln Ser Ile Leu Glu Leu Phe Asn Thr Ser
                325                 330                 335
Tyr Cys Pro Tyr Ser Gln Cys Ala Phe Asn Gly Ile Phe Leu Pro Pro
            340                 345                 350
Leu Gln Gly Asp Phe Gly Ala Phe Ser Ala Phe Tyr Phe Val Met Lys
        355                 360                 365
Phe Leu Asn Leu Thr Ser Glu Lys Val Ser Gln Glu Lys Val Thr Glu
    370                 375                 380
Met Met Lys Lys Phe Cys Ala Gln Pro Trp Glu Glu Ile Lys Thr Ser
385                 390                 395                 400
Tyr Ala Gly Val Lys Glu Lys Tyr Leu Ser Glu Tyr Cys Phe Ser Gly
                405                 410                 415
Thr Tyr Ile Leu Ser Leu Leu Leu Gln Gly Tyr His Phe Thr Ala Asp
            420                 425                 430
Ser Trp Glu His Ile His Phe Ile Gly Lys Ile Gln Gly Ser Asp Ala
        435                 440                 445
Gly Trp Thr Leu Gly Tyr Met Leu Asn Leu Thr Asn Met Ile Pro Ala
    450                 455                 460
Glu Gln Pro Leu Ser Thr Pro Leu Ser His Ser Thr
465                 470                 475

<210> SEQ ID NO 5
<211> LENGTH: 1365
<212> TYPE: DNA
<213> ORGANISM: Artificial Sequence
<220> FEATURE:
<223> OTHER INFORMATION: Description of Artificial Sequence: Fusion
      construct of human CD39
<220> FEATURE:
<221> NAME/KEY: CDS
```

-continued

<222> LOCATION: (1)..(1362)

<400> SEQUENCE: 5

```
gca cct act tca agt tct aca aag aaa aca cag cta act agt tca acc      48
Ala Pro Thr Ser Ser Ser Thr Lys Lys Thr Gln Leu Thr Ser Ser Thr
 1               5                  10                  15 cag aac aaa gca ttg cca gaa aac gtt aag tat ggg att gtg ctg gat      96
Gln Asn Lys Ala Leu Pro Glu Asn Val Lys Tyr Gly Ile Val Leu Asp
             20                  25                  30 gcg ggt tct tct cac aca agt tta tac atc tat aag tgg cca gca gaa     144
Ala Gly Ser Ser His Thr Ser Leu Tyr Ile Tyr Lys Trp Pro Ala Glu
         35                  40                  45 aag gag aat gac aca ggc gtg gtg cat caa gta gaa gaa tgc agg gtt     192
Lys Glu Asn Asp Thr Gly Val Val His Gln Val Glu Glu Cys Arg Val
     50                  55                  60 aaa ggt cct gga atc tca aaa ttt gtt cag aaa gta aat gaa ata ggc     240
Lys Gly Pro Gly Ile Ser Lys Phe Val Gln Lys Val Asn Glu Ile Gly
 65                  70                  75                  80 att tac ctg act gat tgc atg gaa aga gct agg gaa gtg att cca agg     288
Ile Tyr Leu Thr Asp Cys Met Glu Arg Ala Arg Glu Val Ile Pro Arg
                 85                  90                  95 tcc cag cac caa gag aca ccc gtt tac ctg gga gcc acg gca ggc atg     336
Ser Gln His Gln Glu Thr Pro Val Tyr Leu Gly Ala Thr Ala Gly Met
            100                 105                 110 cgg ttg ctc agg atg gaa agt gaa gag ttg gca gac agg gtt ctg gat     384
Arg Leu Leu Arg Met Glu Ser Glu Glu Leu Ala Asp Arg Val Leu Asp
        115                 120                 125 gtg gtg gag agg agc ctc agc aac tac ccc ttt gac ttc cag ggt gcc     432
Val Val Glu Arg Ser Leu Ser Asn Tyr Pro Phe Asp Phe Gln Gly Ala
    130                 135                 140 agg atc att act ggc caa gag gaa ggt gcc tat ggc tgg att act atc     480
Arg Ile Ile Thr Gly Gln Glu Glu Gly Ala Tyr Gly Trp Ile Thr Ile
145                 150                 155                 160 aac tat ctg ctg ggc aaa ttc agt cag aaa aca agg tgg ttc agc ata     528
Asn Tyr Leu Leu Gly Lys Phe Ser Gln Lys Thr Arg Trp Phe Ser Ile
                165                 170                 175 gtc cca tat gaa acc aat aat cag gaa acc ttt gga gct ttg gac ctt     576
Val Pro Tyr Glu Thr Asn Asn Gln Glu Thr Phe Gly Ala Leu Asp Leu
            180                 185                 190 ggg gga gcc tct aca caa gtc act ttt gta ccc caa aac cag act atc     624
Gly Gly Ala Ser Thr Gln Val Thr Phe Val Pro Gln Asn Gln Thr Ile
        195                 200                 205 gag tcc cca gat aat gct ctg caa ttt cgc ctc tat ggc aag gac tac     672
Glu Ser Pro Asp Asn Ala Leu Gln Phe Arg Leu Tyr Gly Lys Asp Tyr
    210                 215                 220 aat gtc tac aca cat agc ttc ttg tgc tat ggg aag gat cag gca ctc     720
Asn Val Tyr Thr His Ser Phe Leu Cys Tyr Gly Lys Asp Gln Ala Leu
225                 230                 235                 240 tgg cag aaa ctg gcc aag gac att cag gtt gca agt aat gaa att ctc     768
Trp Gln Lys Leu Ala Lys Asp Ile Gln Val Ala Ser Asn Glu Ile Leu
                245                 250                 255 agg gac cca tgc ttt cat cct gga tat aag aag gta gtg aac gta agt     816
Arg Asp Pro Cys Phe His Pro Gly Tyr Lys Lys Val Val Asn Val Ser
            260                 265                 270 gac ctt tac aag acc ccc tgc acc aag aga ttt gag atg act ctt cca     864
Asp Leu Tyr Lys Thr Pro Cys Thr Lys Arg Phe Glu Met Thr Leu Pro
        275                 280                 285 ttc cag cag ttt gaa atc cag ggt att gga aac tat caa caa tgc cat     912
Phe Gln Gln Phe Glu Ile Gln Gly Ile Gly Asn Tyr Gln Gln Cys His
    290                 295                 300
```

```
caa agc atc ctg gag ctc ttc aac acc agt tac tgc cct tac tcc cag        960
Gln Ser Ile Leu Glu Leu Phe Asn Thr Ser Tyr Cys Pro Tyr Ser Gln
305                 310                 315                 320 tgt gcc ttc aat ggg att ttc ttg cca cca ctc cag ggg gat ttt ggg       1008
Cys Ala Phe Asn Gly Ile Phe Leu Pro Pro Leu Gln Gly Asp Phe Gly
                325                 330                 335 gca ttt tca gct ttt tac ttt gtg atg aag ttt tta aac ttg aca tca       1056
Ala Phe Ser Ala Phe Tyr Phe Val Met Lys Phe Leu Asn Leu Thr Ser
            340                 345                 350 gag aaa gtc tct cag gaa aag gtg act gag atg atg aaa aag ttc tgt       1104
Glu Lys Val Ser Gln Glu Lys Val Thr Glu Met Met Lys Lys Phe Cys
        355                 360                 365 gct cag cct tgg gag gag ata aaa aca tct tac gct gga gta aag gag       1152
Ala Gln Pro Trp Glu Glu Ile Lys Thr Ser Tyr Ala Gly Val Lys Glu
    370                 375                 380 aag tac ctg agt gaa tac tgc ttt tct ggt acc tac att ctc tcc ctc       1200
Lys Tyr Leu Ser Glu Tyr Cys Phe Ser Gly Thr Tyr Ile Leu Ser Leu
385                 390                 395                 400 ctt ctg caa ggc tat cat ttc aca gct gat tcc tgg gag cac atc cat       1248
Leu Leu Gln Gly Tyr His Phe Thr Ala Asp Ser Trp Glu His Ile His
                405                 410                 415 ttc att ggc aag atc cag ggc agc gac gcc ggc tgg act ttg ggc tac       1296
Phe Ile Gly Lys Ile Gln Gly Ser Asp Ala Gly Trp Thr Leu Gly Tyr
            420                 425                 430 atg ctg aac ctg acc aac atg atc cca gct gag caa cca ttg tcc aca       1344
Met Leu Asn Leu Thr Asn Met Ile Pro Ala Glu Gln Pro Leu Ser Thr
        435                 440                 445 cct ctc tcc cac tcc acc taa                                           1365
Pro Leu Ser His Ser Thr
    450
```

<210> SEQ ID NO 6
<211> LENGTH: 454
<212> TYPE: PRT
<213> ORGANISM: Artificial Sequence
<220> FEATURE:
<223> OTHER INFORMATION: Description of Artificial Sequence: Fusion construct of human CD39

<400> SEQUENCE: 6

```
Ala Pro Thr Ser Ser Thr Lys Lys Thr Gln Leu Thr Ser Ser Thr
 1               5                  10                  15

Gln Asn Lys Ala Leu Pro Glu Asn Val Lys Tyr Gly Ile Val Leu Asp
                20                  25                  30

Ala Gly Ser Ser His Thr Ser Leu Tyr Ile Tyr Lys Trp Pro Ala Glu
            35                  40                  45

Lys Glu Asn Asp Thr Gly Val Val His Gln Val Glu Cys Arg Val
        50                  55                  60

Lys Gly Pro Gly Ile Ser Lys Phe Val Gln Lys Val Asn Glu Ile Gly
65                  70                  75                  80

Ile Tyr Leu Thr Asp Cys Met Glu Arg Ala Arg Glu Val Ile Pro Arg
                85                  90                  95

Ser Gln His Gln Glu Thr Pro Val Tyr Leu Gly Ala Thr Ala Gly Met
            100                 105                 110

Arg Leu Leu Arg Met Glu Ser Glu Glu Leu Ala Asp Arg Val Leu Asp
        115                 120                 125

Val Val Glu Arg Ser Leu Ser Asn Tyr Pro Phe Asp Phe Gln Gly Ala
    130                 135                 140
```

```
Arg Ile Ile Thr Gly Gln Glu Glu Gly Ala Tyr Gly Trp Ile Thr Ile
145                 150                 155                 160

Asn Tyr Leu Leu Gly Lys Phe Ser Gln Lys Thr Arg Trp Phe Ser Ile
            165                 170                 175

Val Pro Tyr Glu Thr Asn Asn Gln Glu Thr Phe Gly Ala Leu Asp Leu
        180                 185                 190

Gly Gly Ala Ser Thr Gln Val Thr Phe Val Pro Gln Asn Gln Thr Ile
        195                 200                 205

Glu Ser Pro Asp Asn Ala Leu Gln Phe Arg Leu Tyr Gly Lys Asp Tyr
210                 215                 220

Asn Val Tyr Thr His Ser Phe Leu Cys Tyr Gly Lys Asp Gln Ala Leu
225                 230                 235                 240

Trp Gln Lys Leu Ala Lys Asp Ile Gln Val Ala Ser Asn Glu Ile Leu
            245                 250                 255

Arg Asp Pro Cys Phe His Pro Gly Tyr Lys Lys Val Val Asn Val Ser
        260                 265                 270

Asp Leu Tyr Lys Thr Pro Cys Thr Lys Arg Phe Glu Met Thr Leu Pro
        275                 280                 285

Phe Gln Gln Phe Glu Ile Gln Gly Ile Gly Asn Tyr Gln Gln Cys His
290                 295                 300

Gln Ser Ile Leu Glu Leu Phe Asn Thr Ser Tyr Cys Pro Tyr Ser Gln
305                 310                 315                 320

Cys Ala Phe Asn Gly Ile Phe Leu Pro Pro Leu Gln Gly Asp Phe Gly
            325                 330                 335

Ala Phe Ser Ala Phe Tyr Phe Val Met Lys Phe Leu Asn Leu Thr Ser
        340                 345                 350

Glu Lys Val Ser Gln Glu Lys Val Thr Glu Met Met Lys Lys Phe Cys
        355                 360                 365

Ala Gln Pro Trp Glu Glu Ile Lys Thr Ser Tyr Ala Gly Val Lys Glu
370                 375                 380

Lys Tyr Leu Ser Glu Tyr Cys Phe Ser Gly Thr Tyr Ile Leu Ser Leu
385                 390                 395                 400

Leu Leu Gln Gly Tyr His Phe Thr Ala Asp Ser Trp Glu His Ile His
            405                 410                 415

Phe Ile Gly Lys Ile Gln Gly Ser Asp Ala Gly Trp Thr Leu Gly Tyr
        420                 425                 430

Met Leu Asn Leu Thr Asn Met Ile Pro Ala Glu Gln Pro Leu Ser Thr
        435                 440                 445

Pro Leu Ser His Ser Thr
    450
```

<210> SEQ ID NO 7
<211> LENGTH: 1437
<212> TYPE: DNA
<213> ORGANISM: Artificial Sequence
<220> FEATURE:
<223> OTHER INFORMATION: Description of Artificial Sequence: Fusion
      construct of human CD39
<220> FEATURE:
<221> NAME/KEY: CDS
<222> LOCATION: (1)..(1434)

<400> SEQUENCE: 7

```
atg gcc ctg tgg atc gac agg atg caa ctc ctg tct tgc att gca cta     48
Met Ala Leu Trp Ile Asp Arg Met Gln Leu Leu Ser Cys Ile Ala Leu
  1               5                  10                  15 agt ctt gca ctt gtc aca aac agt gca cct act tca agt tct aca aag     96
```

| | | |
|---|---|---|
| Ser Leu Ala Leu Val Thr Asn Ser Ala Pro Thr Ser Ser Thr Lys<br>          20                        25                    30 | |
| aaa aca cag cta act agt tca acc cag aac aaa gca ttg cca gaa aac<br>Lys Thr Gln Leu Thr Ser Ser Thr Gln Asn Lys Ala Leu Pro Glu Asn<br>        35                      40                    45 | 144 |
| gtt aag tat ggg att gtg ctg gat gcg ggt tct tct cac aca agt tta<br>Val Lys Tyr Gly Ile Val Leu Asp Ala Gly Ser Ser His Thr Ser Leu<br> 50                    55                    60 | 192 |
| tac atc tat aag tgg cca gca gaa aag gag aat gac aca ggc gtg gtg<br>Tyr Ile Tyr Lys Trp Pro Ala Glu Lys Glu Asn Asp Thr Gly Val Val<br>65                   70                    75                    80 | 240 |
| cat caa gta gaa gaa tgc agg gtt aaa ggt cct gga atc tca aaa ttt<br>His Gln Val Glu Glu Cys Arg Val Lys Gly Pro Gly Ile Ser Lys Phe<br>                    85                        90                    95 | 288 |
| gtt cag aaa gta aat gaa ata ggc att tac ctg act gat tgc atg gaa<br>Val Gln Lys Val Asn Glu Ile Gly Ile Tyr Leu Thr Asp Cys Met Glu<br>        100                    105                  110 | 336 |
| aga gct agg gaa gtg att cca agg tcc cag cac caa gag aca ccc gtt<br>Arg Ala Arg Glu Val Ile Pro Arg Ser Gln His Gln Glu Thr Pro Val<br>        115                    120                  125 | 384 |
| tac ctg gga gcc acg gca ggc atg cgg ttg ctc agg atg gaa agt gaa<br>Tyr Leu Gly Ala Thr Ala Gly Met Arg Leu Leu Arg Met Glu Ser Glu<br>        130                    135                  140 | 432 |
| gag ttg gca gac agg gtt ctg gat gtg gtg gag agg agc ctc agc aac<br>Glu Leu Ala Asp Arg Val Leu Asp Val Val Glu Arg Ser Leu Ser Asn<br>145                    150                    155                    160 | 480 |
| tac ccc ttt gac ttc cag ggt gcc agg atc att act ggc caa gag gaa<br>Tyr Pro Phe Asp Phe Gln Gly Ala Arg Ile Ile Thr Gly Gln Glu Glu<br>                165                    170                  175 | 528 |
| ggt gcc tat ggc tgg att act atc aac tat ctg ctg ggc aaa ttc agt<br>Gly Ala Tyr Gly Trp Ile Thr Ile Asn Tyr Leu Leu Gly Lys Phe Ser<br>        180                    185                  190 | 576 |
| cag aaa aca agg tgg ttc agc ata gtc cca tat gaa acc aat aat cag<br>Gln Lys Thr Arg Trp Phe Ser Ile Val Pro Tyr Glu Thr Asn Asn Gln<br>        195                    200                  205 | 624 |
| gaa acc ttt gga gct ttg gac ctt ggg gga gcc tct aca caa gtc act<br>Glu Thr Phe Gly Ala Leu Asp Leu Gly Gly Ala Ser Thr Gln Val Thr<br>        210                    215                  220 | 672 |
| ttt gta ccc caa aac cag act atc gag tcc cca gat aat gct ctg caa<br>Phe Val Pro Gln Asn Gln Thr Ile Glu Ser Pro Asp Asn Ala Leu Gln<br>225                    230                    235                    240 | 720 |
| ttt cgc ctc tat ggc aag gac tac aat gtc tac aca cat agc ttc ttg<br>Phe Arg Leu Tyr Gly Lys Asp Tyr Asn Val Tyr Thr His Ser Phe Leu<br>                    245                    250                  255 | 768 |
| tgc tat ggg aag gat cag gca ctc tgg cag aaa ctg gcc aag gac att<br>Cys Tyr Gly Lys Asp Gln Ala Leu Trp Gln Lys Leu Ala Lys Asp Ile<br>        260                    265                  270 | 816 |
| cag gtt gca agt aat gaa att ctc agg gac cca tgc ttt cat cct gga<br>Gln Val Ala Ser Asn Glu Ile Leu Arg Asp Pro Cys Phe His Pro Gly<br>        275                    280                  285 | 864 |
| tat aag aag gta gtg aac gta agt gac ctt tac aag acc ccc tgc acc<br>Tyr Lys Lys Val Val Asn Val Ser Asp Leu Tyr Lys Thr Pro Cys Thr<br>        290                    295                  300 | 912 |
| aag aga ttt gag atg act ctt cca ttc cag cag ttt gaa atc cag ggt<br>Lys Arg Phe Glu Met Thr Leu Pro Phe Gln Gln Phe Glu Ile Gln Gly<br>305                    310                    315                    320 | 960 |
| att gga aac tat caa caa tgc cat caa agc atc ctg gag ctc ttc aac<br>Ile Gly Asn Tyr Gln Gln Cys His Gln Ser Ile Leu Glu Leu Phe Asn<br>                    325                    330                  335 | 1008 |

```
acc agt tac tgc cct tac tcc cag tgt gcc ttc aat ggg att ttc ttg    1056
Thr Ser Tyr Cys Pro Tyr Ser Gln Cys Ala Phe Asn Gly Ile Phe Leu
            340                 345                 350 cca cca ctc cag ggg gat ttt ggg gca ttt tca gct ttt tac ttt gtg    1104
Pro Pro Leu Gln Gly Asp Phe Gly Ala Phe Ser Ala Phe Tyr Phe Val
        355                 360                 365 atg aag ttt tta aac ttg aca tca gag aaa gtc tct cag gaa aag gtg    1152
Met Lys Phe Leu Asn Leu Thr Ser Glu Lys Val Ser Gln Glu Lys Val
370                 375                 380 act gag atg atg aaa aag ttc tgt gct cag cct tgg gag gag ata aaa    1200
Thr Glu Met Met Lys Lys Phe Cys Ala Gln Pro Trp Glu Glu Ile Lys
385                 390                 395                 400 aca tct tac gct gga gta aag gag aag tac ctg agt gaa tac tgc ttt    1248
Thr Ser Tyr Ala Gly Val Lys Glu Lys Tyr Leu Ser Glu Tyr Cys Phe
            405                 410                 415 tct ggt acc tac att ctc tcc ctc ctt ctg caa ggc tat cat ttc aca    1296
Ser Gly Thr Tyr Ile Leu Ser Leu Leu Leu Gln Gly Tyr His Phe Thr
        420                 425                 430 gct gat tcc tgg gag cac atc cat ttc att ggc aag atc cag ggc agc    1344
Ala Asp Ser Trp Glu His Ile His Phe Ile Gly Lys Ile Gln Gly Ser
    435                 440                 445 gac gcc ggc tgg act ttg ggc tac atg ctg aac ctg acc aac atg atc    1392
Asp Ala Gly Trp Thr Leu Gly Tyr Met Leu Asn Leu Thr Asn Met Ile
450                 455                 460 cca gct gag caa cca ttg tcc aca cct ctc tcc cac tcc acc taa       1437
Pro Ala Glu Gln Pro Leu Ser Thr Pro Leu Ser His Ser Thr
465                 470                 475

<210> SEQ ID NO 8
<211> LENGTH: 478
<212> TYPE: PRT
<213> ORGANISM: Artificial Sequence
<220> FEATURE:
<223> OTHER INFORMATION: Description of Artificial Sequence:  Fusion
      construct of human CD39

<400> SEQUENCE: 8

Met Ala Leu Trp Ile Asp Arg Met Gln Leu Leu Ser Cys Ile Ala Leu
1               5                   10                  15

Ser Leu Ala Leu Val Thr Asn Ser Ala Pro Thr Ser Ser Ser Thr Lys
            20                  25                  30

Lys Thr Gln Leu Thr Ser Ser Thr Gln Asn Lys Ala Leu Pro Glu Asn
        35                  40                  45

Val Lys Tyr Gly Ile Val Leu Asp Ala Gly Ser Ser His Thr Ser Leu
    50                  55                  60

Tyr Ile Tyr Lys Trp Pro Ala Glu Lys Glu Asn Asp Thr Gly Val Val
65                  70                  75                  80

His Gln Val Glu Glu Cys Arg Val Lys Gly Pro Gly Ile Ser Lys Phe
                85                  90                  95

Val Gln Lys Val Asn Glu Ile Gly Ile Tyr Leu Thr Asp Cys Met Glu
            100                 105                 110

Arg Ala Arg Glu Val Ile Pro Arg Ser Gln His Gln Glu Thr Pro Val
        115                 120                 125

Tyr Leu Gly Ala Thr Ala Gly Met Arg Leu Leu Arg Met Glu Ser Glu
    130                 135                 140

Glu Leu Ala Asp Arg Val Leu Asp Val Val Glu Arg Ser Leu Ser Asn
145                 150                 155                 160

Tyr Pro Phe Asp Phe Gln Gly Ala Arg Ile Ile Thr Gly Gln Glu Glu
                165                 170                 175
```

```
Gly Ala Tyr Gly Trp Ile Thr Ile Asn Tyr Leu Leu Gly Lys Phe Ser
            180                 185                 190

Gln Lys Thr Arg Trp Phe Ser Ile Val Pro Tyr Glu Thr Asn Asn Gln
        195                 200                 205

Glu Thr Phe Gly Ala Leu Asp Leu Gly Gly Ala Ser Thr Gln Val Thr
    210                 215                 220

Phe Val Pro Gln Asn Gln Thr Ile Glu Ser Pro Asp Asn Ala Leu Gln
225                 230                 235                 240

Phe Arg Leu Tyr Gly Lys Asp Tyr Asn Val Tyr Thr His Ser Phe Leu
                245                 250                 255

Cys Tyr Gly Lys Asp Gln Ala Leu Trp Gln Lys Leu Ala Lys Asp Ile
            260                 265                 270

Gln Val Ala Ser Asn Glu Ile Leu Arg Asp Pro Cys Phe His Pro Gly
        275                 280                 285

Tyr Lys Lys Val Val Asn Val Ser Asp Leu Tyr Lys Thr Pro Cys Thr
    290                 295                 300

Lys Arg Phe Glu Met Thr Leu Pro Phe Gln Gln Phe Glu Ile Gln Gly
305                 310                 315                 320

Ile Gly Asn Tyr Gln Gln Cys His Gln Ser Ile Leu Glu Leu Phe Asn
                325                 330                 335

Thr Ser Tyr Cys Pro Tyr Ser Gln Cys Ala Phe Asn Gly Ile Phe Leu
            340                 345                 350

Pro Pro Leu Gln Gly Asp Phe Gly Ala Phe Ser Ala Phe Tyr Phe Val
        355                 360                 365

Met Lys Phe Leu Asn Leu Thr Ser Glu Lys Val Ser Gln Glu Lys Val
    370                 375                 380

Thr Glu Met Met Lys Lys Phe Cys Ala Gln Pro Trp Glu Glu Ile Lys
385                 390                 395                 400

Thr Ser Tyr Ala Gly Val Lys Glu Lys Tyr Leu Ser Glu Tyr Cys Phe
                405                 410                 415

Ser Gly Thr Tyr Ile Leu Ser Leu Leu Leu Gln Gly Tyr His Phe Thr
            420                 425                 430

Ala Asp Ser Trp Glu His Ile His Phe Ile Gly Lys Ile Gln Gly Ser
        435                 440                 445

Asp Ala Gly Trp Thr Leu Gly Tyr Met Leu Asn Leu Thr Asn Met Ile
    450                 455                 460

Pro Ala Glu Gln Pro Leu Ser Thr Pro Leu Ser His Ser Thr
465                 470                 475

<210> SEQ ID NO 9
<211> LENGTH: 24
<212> TYPE: PRT
<213> ORGANISM: Artificial Sequence
<220> FEATURE:
<223> OTHER INFORMATION: Description of Artificial Sequence: Synthetic
      signal sequence

<400> SEQUENCE: 9

Met Ala Leu Trp Ile Asp Arg Met Gln Leu Leu Ser Cys Ile Ala Leu
  1               5                  10                  15

Ser Leu Ala Leu Val Thr Asn Ser
            20

<210> SEQ ID NO 10
<211> LENGTH: 8
<212> TYPE: PRT
```

```
<213> ORGANISM: Artificial Sequence
<220> FEATURE:
<223> OTHER INFORMATION: Description of Artificial Sequence:  Synthetic
      peptide

<400> SEQUENCE: 10

Asp Tyr Lys Asp Asp Asp Asp Lys
1               5

<210> SEQ ID NO 11
<211> LENGTH: 43
<212> TYPE: PRT
<213> ORGANISM: Artificial Sequence
<220> FEATURE:
<223> OTHER INFORMATION: Description of Artificial Sequence:  Fusion
      construct of human CD39

<400> SEQUENCE: 11

Met Ala Leu Trp Ile Asp Arg Met Gln Leu Leu Ser Cys Ile Ala Leu
1               5                  10                  15

Ser Leu Ala Leu Val Thr Asn Ser Ala Pro Thr Ser Ser Ser Thr Lys
            20                  25                  30

Lys Thr Gln Leu Thr Ser Ser Thr Gln Asn Lys
        35                  40

<210> SEQ ID NO 12
<211> LENGTH: 29
<212> TYPE: PRT
<213> ORGANISM: Artificial Sequence
<220> FEATURE:
<223> OTHER INFORMATION: Description of Artificial Sequence:  Fusion
      construct of human CD39

<400> SEQUENCE: 12

Met Ala Leu Trp Ile Asp Arg Met Gln Leu Leu Ser Cys Ile Ala Leu
1               5                  10                  15

Ser Leu Ala Leu Val Thr Asn Ser Ala Thr Gln Asn Lys
            20                  25

<210> SEQ ID NO 13
<211> LENGTH: 31
<212> TYPE: PRT
<213> ORGANISM: Artificial Sequence
<220> FEATURE:
<223> OTHER INFORMATION: Description of Artificial Sequence:  Fusion
      construct of human CD39

<400> SEQUENCE: 13

Met Ala Leu Trp Ile Asp Arg Met Gln Leu Leu Ser Cys Ile Ala Leu
1               5                  10                  15

Ser Leu Ala Leu Val Thr Asn Ser Ala Ser Ser Thr Gln Asn Lys
            20                  25                  30

<210> SEQ ID NO 14
<211> LENGTH: 87
<212> TYPE: DNA
<213> ORGANISM: Artificial Sequence
<220> FEATURE:
<223> OTHER INFORMATION: Description of Artificial Sequence:  Synthetic
      oligonucleotide

<400> SEQUENCE: 14
ccggctggac tttgggctac atgctgaacc tgaccaacat gatcccagct gagcaaccat      60
tgtccacacc tctctcccac gagcccc                                         87
```

```
<210> SEQ ID NO 15
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gatcggggct cgtgggagag aggtgtggac aatggttgct cagctgggat catgttggtc      60
aggttcagca tgtagcccaa agtccag                                          87

<210> SEQ ID NO 16
<211> LENGTH: 740
<212> TYPE: DNA
<213> ORGANISM: Homo sapiens
<220> FEATURE:
<221> NAME/KEY: CDS
<222> LOCATION: (42)..(737)

<400> SEQUENCE: 16
cggtaccgct agcgtcgaca ggcctaggat atcgatacgt a gag ccc aga tct tgt       56
                                             Glu Pro Arg Ser Cys
                                               1               5 gac aaa act cac aca tgc cca ccg tgc cca gca cct gaa gcc gag ggc        104
Asp Lys Thr His Thr Cys Pro Pro Cys Pro Ala Pro Glu Ala Glu Gly
             10                  15                  20 gcg ccg tca gtc ttc ctc ttc ccc cca aaa ccc aag gac acc ctc atg        152
Ala Pro Ser Val Phe Leu Phe Pro Pro Lys Pro Lys Asp Thr Leu Met
         25                  30                  35 atc tcc cgg acc cct gag gtc aca tgc gtg gtg gtg gac gtg agc cac        200
Ile Ser Arg Thr Pro Glu Val Thr Cys Val Val Val Asp Val Ser His
     40                  45                  50 gaa gac cct gag gtc aag ttc aac tgg tac gtg gac ggc gtg gag gtg        248
Glu Asp Pro Glu Val Lys Phe Asn Trp Tyr Val Asp Gly Val Glu Val
 55                  60                  65 cat aat gcc aag aca aag ccg cgg gag gag cag tac aac agc acg tac        296
His Asn Ala Lys Thr Lys Pro Arg Glu Glu Gln Tyr Asn Ser Thr Tyr
 70                  75                  80                  85 cgg gtg gtc agc gtc ctc acc gtc ctg cac cag gac tgg ctg aat ggc        344
Arg Val Val Ser Val Leu Thr Val Leu His Gln Asp Trp Leu Asn Gly
                 90                  95                 100 aag gac tac aag tgc aag gtc tcc aac aaa gcc ctc cca gcc ccc atc        392
Lys Asp Tyr Lys Cys Lys Val Ser Asn Lys Ala Leu Pro Ala Pro Met
            105                 110                 115 cag aaa acc atc tcc aaa gcc aaa ggg cag ccc cga gaa cca cag gtg        440
Gln Lys Thr Ile Ser Lys Ala Lys Gly Gln Pro Arg Glu Pro Gln Val
        120                 125                 130 tac acc ctg ccc cca tcc cgg gat gag ctg acc aag aac cag gtc agc        488
Tyr Thr Leu Pro Pro Ser Arg Asp Glu Leu Thr Lys Asn Gln Val Ser
    135                 140                 145 ctg acc tgc ctg gtc aaa ggc ttc tat ccc agg cac atc gcc gtg gag        536
Leu Thr Cys Leu Val Lys Gly Phe Tyr Pro Arg His Ile Ala Val Glu
150                 155                 160                 165 tgg gag agc aat ggg cag ccg gag aac aac tac aag acc acg cct ccc        584
Trp Glu Ser Asn Gly Gln Pro Glu Asn Asn Tyr Lys Thr Thr Pro Pro
                170                 175                 180 gtg ctg gac tcc gac ggc tcc ttc ttc ctc tac agc aag ctc acc gtg        632
Val Leu Asp Ser Asp Gly Ser Phe Phe Leu Tyr Ser Lys Leu Thr Val
            185                 190                 195 gac aag agc agg tgg cag cag ggg aac gtc ttc tca tgc tcc gtg atg        680
```

```
Asp Lys Ser Arg Trp Gln Gln Gly Asn Val Phe Ser Cys Ser Val Met
        200                 205                 210 cat gag gct ctg cac aac cac tac acg cag aag agc ctc tcc ctg tct      728
His Glu Ala Leu His Asn His Tyr Thr Gln Lys Ser Leu Ser Leu Ser
        215                 220                 225 ccg ggt aaa tga                                                       740
Pro Gly Lys
230

<210> SEQ ID NO 17
<211> LENGTH: 232
<212> TYPE: PRT
<213> ORGANISM: Homo sapiens

<400> SEQUENCE: 17

Glu Pro Arg Ser Cys Asp Lys Thr His Thr Cys Pro Pro Cys Pro Ala
 1               5                  10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Asp Tyr Lys Cys Lys Val Ser Asn Lys Ala
            100                 105                 110

Leu Pro Ala Pro Met Gln Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Arg
145                 150                 155                 160

His Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ctttccatcc tgagcaac                                                    18

<210> SEQ ID NO 19
```

<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
aaaaaactag tcagaacaaa gctttgccag aaaacg                      36

<210> SEQ ID NO 20
<211> LENGTH: 24
<212> TYPE: PRT
<213> ORGANISM: Mus sp.

<400> SEQUENCE: 20

Met Phe His Val Ser Phe Arg Tyr Ile Phe Gly Ile Pro Pro Leu Ile
 1               5                  10                  15

Leu Val Leu Leu Pro Val Thr Ser
            20

<210> SEQ ID NO 21
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ctagttctgg agactacaaa gatgacgatg acaaaaccca gaacaa          46

<210> SEQ ID NO 22
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
agctttgttc tgggttttgt catcgtcatc tttgtagtct ccagaa          46

<210> SEQ ID NO 23
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ccggctggac tttgggctac atgctgaacc tgaccaacat gatcccagct gagcaaccat   60
tgtccacacc tctctcccac tccacctaa                                    89

<210> SEQ ID NO 24
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ggccttaggt ggagtgggag agaggtgtgg acaatggttg ctcagctggg atcatgttgg   60

```
tcaggttcag catgtagccc aaagtccag                                        89
```

<210> SEQ ID NO 25
<211> LENGTH: 1464
<212> TYPE: DNA
<213> ORGANISM: Artificial Sequence
<220> FEATURE:
<221> NAME/KEY: CDS
<222> LOCATION: (1)..(1461)
<220> FEATURE:
<223> OTHER INFORMATION: Description of Artificial Sequence: Fusion
      construct of human CD39

<400> SEQUENCE: 25

```
atg gcc ctg tgg atc gac agg atg caa ctc ctg tct tgc att gca cta        48
Met Ala Leu Trp Ile Asp Arg Met Gln Leu Leu Ser Cys Ile Ala Leu
1               5                   10                  15 agt ctt gca ctt gtc aca aac agt gca cct act tca agt tct aca aag        96
Ser Leu Ala Leu Val Thr Asn Ser Ala Pro Thr Ser Ser Ser Thr Lys
            20                  25                  30 aaa aca cag cta act agt tca gga gac tac aaa gat gac gat gac aaa       144
Lys Thr Gln Leu Thr Ser Ser Gly Asp Tyr Lys Asp Asp Asp Asp Lys
        35                  40                  45 acc cag aac aaa gca ttg cca gaa aac gtt aag tat ggg att gtg ctg       192
Thr Gln Asn Lys Ala Leu Pro Glu Asn Val Lys Tyr Gly Ile Val Leu
    50                  55                  60 gat gcg ggt tct tct cac aca agt tta tac atc tat aag tgg cca gca       240
Asp Ala Gly Ser Ser His Thr Ser Leu Tyr Ile Tyr Lys Trp Pro Ala
65                  70                  75                  80 gaa aag gag aat gac aca ggc gtg gtg cat caa gta gaa gaa tgc agg       288
Glu Lys Glu Asn Asp Thr Gly Val Val His Gln Val Glu Glu Cys Arg
                85                  90                  95 gtt aaa ggt cct gga atc tca aaa ttt gtt cag aaa gta aat gaa ata       336
Val Lys Gly Pro Gly Ile Ser Lys Phe Val Gln Lys Val Asn Glu Ile
            100                 105                 110 ggc att tac ctg act gat tgc atg gaa aga gct agg gaa gtg att cca       384
Gly Ile Tyr Leu Thr Asp Cys Met Glu Arg Ala Arg Glu Val Ile Pro
        115                 120                 125 agg tcc cag cac caa gag aca ccc gtt tac ctg gga gcc acg gca ggc       432
Arg Ser Gln His Gln Glu Thr Pro Val Tyr Leu Gly Ala Thr Ala Gly
    130                 135                 140 atg cgg ttg ctc agg atg gaa agt gaa gag ttg gca gac agg gtt ctg       480
Met Arg Leu Leu Arg Met Glu Ser Glu Glu Leu Ala Asp Arg Val Leu
145                 150                 155                 160 gat gtg gtg gag agg agc ctc agc aac tac ccc ttt gac ttc cag ggt       528
Asp Val Val Glu Arg Ser Leu Ser Asn Tyr Pro Phe Asp Phe Gln Gly
                165                 170                 175 gcc agg atc att act ggc caa gag gaa ggt gcc tat ggc tgg att act       576
Ala Arg Ile Ile Thr Gly Gln Glu Glu Gly Ala Tyr Gly Trp Ile Thr
            180                 185                 190 atc aac tat ctg ctg ggc aaa ttc agt cag aaa aca agg tgg ttc agc       624
Ile Asn Tyr Leu Leu Gly Lys Phe Ser Gln Lys Thr Arg Trp Phe Ser
        195                 200                 205 ata gtc cca tat gaa acc aat aat cag gaa acc ttt gga gct ttg gac       672
Ile Val Pro Tyr Glu Thr Asn Asn Gln Glu Thr Phe Gly Ala Leu Asp
    210                 215                 220 ctt ggg gga gcc tct aca caa gtc act ttt gta ccc caa aac cag act       720
Leu Gly Gly Ala Ser Thr Gln Val Thr Phe Val Pro Gln Asn Gln Thr
225                 230                 235                 240 atc gag tcc cca gat aat gct ctg caa ttt cgc ctc tat ggc aag gac       768
Ile Glu Ser Pro Asp Asn Ala Leu Gln Phe Arg Leu Tyr Gly Lys Asp
                245                 250                 255
```

```
tac aat gtc tac aca cat agc ttc ttg tgc tat ggg aag gat cag gca      816
Tyr Asn Val Tyr Thr His Ser Phe Leu Cys Tyr Gly Lys Asp Gln Ala
        260                 265                 270 ctc tgg cag aaa ctg gcc aag gac att cag gtt gca agt aat gaa att      864
Leu Trp Gln Lys Leu Ala Lys Asp Ile Gln Val Ala Ser Asn Glu Ile
            275                 280                 285 ctc agg gac cca tgc ttt cat cct gga tat aag aag gta gtg aac gta      912
Leu Arg Asp Pro Cys Phe His Pro Gly Tyr Lys Lys Val Val Asn Val
290                 295                 300 agt gac ctt tac aag acc ccc tgc acc aag aga ttt gag atg act ctt      960
Ser Asp Leu Tyr Lys Thr Pro Cys Thr Lys Arg Phe Glu Met Thr Leu
305                 310                 315                 320 cca ttc cag cag ttt gaa atc cag ggt att gga aac tat caa caa tgc     1008
Pro Phe Gln Gln Phe Glu Ile Gln Gly Ile Gly Asn Tyr Gln Gln Cys
                325                 330                 335 cat caa agc atc ctg gag ctc ttc aac acc agt tac tgc cct tac tcc     1056
His Gln Ser Ile Leu Glu Leu Phe Asn Thr Ser Tyr Cys Pro Tyr Ser
                340                 345                 350 cag tgt gcc ttc aat ggg att ttc ttg cca cca ctc cag ggg gat ttt     1104
Gln Cys Ala Phe Asn Gly Ile Phe Leu Pro Pro Leu Gln Gly Asp Phe
            355                 360                 365 ggg gca ttt tca gct ttt tac ttt gtg atg aag ttt tta aac ttg aca     1152
Gly Ala Phe Ser Ala Phe Tyr Phe Val Met Lys Phe Leu Asn Leu Thr
370                 375                 380 tca gag aaa gtc tct cag gaa aag gtg act gag atg atg aaa aag ttc     1200
Ser Glu Lys Val Ser Gln Glu Lys Val Thr Glu Met Met Lys Lys Phe
385                 390                 395                 400 tgt gct cag cct tgg gag gag ata aaa aca tct tac gct gga gta aag     1248
Cys Ala Gln Pro Trp Glu Glu Ile Lys Thr Ser Tyr Ala Gly Val Lys
                405                 410                 415 gag aag tac ctg agt gaa tac tgc ttt tct ggt acc tac att ctc tcc     1296
Glu Lys Tyr Leu Ser Glu Tyr Cys Phe Ser Gly Thr Tyr Ile Leu Ser
            420                 425                 430 ctc ctt ctg caa ggc tat cat ttc aca gct gat tcc tgg gag cac atc     1344
Leu Leu Leu Gln Gly Tyr His Phe Thr Ala Asp Ser Trp Glu His Ile
        435                 440                 445 cat ttc att ggc aag atc cag ggc agc gac gcc ggc tgg act ttg ggc     1392
His Phe Ile Gly Lys Ile Gln Gly Ser Asp Ala Gly Trp Thr Leu Gly
450                 455                 460 tac atg ctg aac ctg acc aac atg atc cca gct gag caa cca ttg tcc     1440
Tyr Met Leu Asn Leu Thr Asn Met Ile Pro Ala Glu Gln Pro Leu Ser
465                 470                 475                 480 aca cct ctc tcc cac tcc acc taa                                     1464
Thr Pro Leu Ser His Ser Thr
                485

<210> SEQ ID NO 26
<211> LENGTH: 487
<212> TYPE: PRT
<213> ORGANISM: Artificial Sequence
<220> FEATURE:
<223> OTHER INFORMATION: Description of Artificial Sequence: Fusion
      construct of human CD39

<400> SEQUENCE: 26

Met Ala Leu Trp Ile Asp Arg Met Gln Leu Leu Ser Cys Ile Ala Leu
 1               5                  10                  15

Ser Leu Ala Leu Val Thr Asn Ser Ala Pro Thr Ser Ser Ser Thr Lys
            20                  25                  30

Lys Thr Gln Leu Thr Ser Ser Gly Asp Tyr Lys Asp Asp Asp Asp Lys
```

-continued

```
                35                  40                  45
Thr Gln Asn Lys Ala Leu Pro Glu Asn Val Lys Tyr Gly Ile Val Leu
 50                  55                  60

Asp Ala Gly Ser Ser His Thr Ser Leu Tyr Ile Tyr Lys Trp Pro Ala
 65                  70                  75                  80

Glu Lys Glu Asn Asp Thr Gly Val Val His Gln Val Glu Glu Cys Arg
                 85                  90                  95

Val Lys Gly Pro Gly Ile Ser Lys Phe Val Gln Lys Val Asn Glu Ile
                100                 105                 110

Gly Ile Tyr Leu Thr Asp Cys Met Glu Arg Ala Arg Glu Val Ile Pro
            115                 120                 125

Arg Ser Gln His Gln Glu Thr Pro Val Tyr Leu Gly Ala Thr Ala Gly
130                 135                 140

Met Arg Leu Leu Arg Met Glu Ser Glu Glu Leu Ala Asp Arg Val Leu
145                 150                 155                 160

Asp Val Val Glu Arg Ser Leu Ser Asn Tyr Pro Phe Asp Phe Gln Gly
                165                 170                 175

Ala Arg Ile Ile Thr Gly Gln Glu Gly Ala Tyr Gly Trp Ile Thr
            180                 185                 190

Ile Asn Tyr Leu Leu Gly Lys Phe Ser Gln Lys Thr Arg Trp Phe Ser
        195                 200                 205

Ile Val Pro Tyr Glu Thr Asn Asn Gln Glu Thr Phe Gly Ala Leu Asp
        210                 215                 220

Leu Gly Gly Ala Ser Thr Gln Val Thr Phe Val Pro Gln Asn Gln Thr
225                 230                 235                 240

Ile Glu Ser Pro Asp Asn Ala Leu Gln Phe Arg Leu Tyr Gly Lys Asp
                245                 250                 255

Tyr Asn Val Tyr Thr His Ser Phe Leu Cys Tyr Gly Lys Asp Gln Ala
                260                 265                 270

Leu Trp Gln Lys Leu Ala Lys Asp Ile Gln Val Ala Ser Asn Glu Ile
            275                 280                 285

Leu Arg Asp Pro Cys Phe His Pro Gly Tyr Lys Lys Val Val Asn Val
290                 295                 300

Ser Asp Leu Tyr Lys Thr Pro Cys Thr Lys Arg Phe Glu Met Thr Leu
305                 310                 315                 320

Pro Phe Gln Gln Phe Glu Ile Gln Gly Ile Gly Asn Tyr Gln Gln Cys
                325                 330                 335

His Gln Ser Ile Leu Glu Leu Phe Asn Thr Ser Tyr Cys Pro Tyr Ser
            340                 345                 350

Gln Cys Ala Phe Asn Gly Ile Phe Leu Pro Pro Leu Gln Gly Asp Phe
        355                 360                 365

Gly Ala Phe Ser Ala Phe Tyr Phe Val Met Lys Phe Leu Asn Leu Thr
    370                 375                 380

Ser Glu Lys Val Ser Gln Glu Lys Val Thr Glu Met Met Lys Lys Phe
385                 390                 395                 400

Cys Ala Gln Pro Trp Glu Glu Ile Lys Thr Ser Tyr Ala Gly Val Lys
                405                 410                 415

Glu Lys Tyr Leu Ser Glu Tyr Cys Phe Ser Gly Thr Tyr Ile Leu Ser
            420                 425                 430

Leu Leu Leu Gln Gly Tyr His Phe Thr Ala Asp Ser Trp Glu His Ile
        435                 440                 445

His Phe Ile Gly Lys Ile Gln Gly Ser Asp Ala Gly Trp Thr Leu Gly
    450                 455                 460
```

```
Tyr Met Leu Asn Leu Thr Asn Met Ile Pro Ala Glu Gln Pro Leu Ser
465                 470                 475                 480

Thr Pro Leu Ser His Ser Thr
                485
```

<210> SEQ ID NO 27
<211> LENGTH: 464
<212> TYPE: PRT
<213> ORGANISM: Artificial Sequence
<220> FEATURE:
<223> OTHER INFORMATION: Description of Artificial Sequence: Fusion construct of human CD39

<400> SEQUENCE: 27

```
Met Ala Leu Trp Ile Asp Arg Met Gln Leu Leu Ser Cys Ile Ala Leu
  1               5                  10                  15

Ser Leu Ala Leu Val Thr Asn Ser Ala Thr Gln Asn Lys Ala Leu Pro
                 20                  25                  30

Glu Asn Val Lys Tyr Gly Ile Val Leu Asp Ala Gly Ser Ser His Thr
             35                  40                  45

Ser Leu Tyr Ile Tyr Lys Trp Pro Ala Glu Lys Glu Asn Asp Thr Gly
 50                  55                  60

Val Val His Gln Val Glu Glu Cys Arg Val Lys Gly Pro Gly Ile Ser
 65                  70                  75                  80

Lys Phe Val Gln Lys Val Asn Glu Ile Gly Ile Tyr Leu Thr Asp Cys
                 85                  90                  95

Met Glu Arg Ala Arg Glu Val Ile Pro Arg Ser Gln His Gln Glu Thr
            100                 105                 110

Pro Val Tyr Leu Gly Ala Thr Ala Gly Met Arg Leu Leu Arg Met Glu
            115                 120                 125

Ser Glu Glu Leu Ala Asp Arg Val Leu Asp Val Val Glu Arg Ser Leu
130                 135                 140

Ser Asn Tyr Pro Phe Asp Phe Gln Gly Ala Arg Ile Ile Thr Gly Gln
145                 150                 155                 160

Glu Glu Gly Ala Tyr Gly Trp Ile Thr Ile Asn Tyr Leu Leu Gly Lys
                165                 170                 175

Phe Ser Gln Lys Thr Arg Trp Phe Ser Ile Val Pro Tyr Glu Thr Asn
            180                 185                 190

Asn Gln Glu Thr Phe Gly Ala Leu Asp Leu Gly Gly Ala Ser Thr Gln
            195                 200                 205

Val Thr Phe Val Pro Gln Asn Gln Thr Ile Glu Ser Pro Asp Asn Ala
210                 215                 220

Leu Gln Phe Arg Leu Tyr Gly Lys Asp Tyr Asn Val Tyr Thr His Ser
225                 230                 235                 240

Phe Leu Cys Tyr Gly Lys Asp Gln Ala Leu Trp Gln Lys Leu Ala Lys
                245                 250                 255

Asp Ile Gln Val Ala Ser Asn Glu Ile Leu Arg Asp Pro Cys Phe His
            260                 265                 270

Pro Gly Tyr Lys Lys Val Val Asn Val Ser Asp Leu Tyr Lys Thr Pro
            275                 280                 285

Cys Thr Lys Arg Phe Glu Met Thr Leu Pro Phe Gln Gln Phe Glu Ile
            290                 295                 300

Gln Gly Ile Gly Asn Tyr Gln Gln Cys His Gln Ser Ile Leu Glu Leu
305                 310                 315                 320

Phe Asn Thr Ser Tyr Cys Pro Tyr Ser Gln Cys Ala Phe Asn Gly Ile
```

-continued

```
                325                 330                 335
Phe Leu Pro Pro Leu Gln Gly Asp Phe Gly Ala Phe Ser Ala Phe Tyr
            340                 345                 350

Phe Val Met Lys Phe Leu Asn Leu Thr Ser Glu Lys Val Ser Gln Glu
            355                 360                 365

Lys Val Thr Glu Met Met Lys Lys Phe Cys Ala Gln Pro Trp Glu Glu
            370                 375                 380

Ile Lys Thr Ser Tyr Ala Gly Val Lys Glu Lys Tyr Leu Ser Glu Tyr
385                 390                 395                 400

Cys Phe Ser Gly Thr Tyr Ile Leu Ser Leu Leu Gln Gly Tyr His
            405                 410                 415

Phe Thr Ala Asp Ser Trp Glu His Ile His Phe Ile Gly Lys Ile Gln
            420                 425                 430

Gly Ser Asp Ala Gly Trp Thr Leu Gly Tyr Met Leu Asn Leu Thr Asn
            435                 440                 445

Met Ile Pro Ala Glu Gln Pro Leu Ser Thr Pro Leu Ser His Ser Thr
450                 455                 460

<210> SEQ ID NO 28
<211> LENGTH: 474
<212> TYPE: PRT
<213> ORGANISM: Artificial Sequence
<220> FEATURE:
<223> OTHER INFORMATION: Description of Artificial Sequence:  Fusion
      construct of human CD39

<400> SEQUENCE: 28

Met Ala Leu Trp Ile Asp Arg Met Gln Leu Leu Ser Cys Ile Ala Leu
1               5                   10                  15

Ser Leu Ala Leu Val Thr Asn Ser Ala Ser Thr Lys Lys Thr Gln Leu
            20                  25                  30

Thr Ser Ser Thr Gln Asn Lys Ala Leu Pro Glu Asn Val Lys Tyr Gly
        35                  40                  45

Ile Val Leu Asp Ala Gly Ser Ser His Thr Ser Leu Tyr Ile Tyr Lys
    50                  55                  60

Trp Pro Ala Glu Lys Glu Asn Asp Thr Gly Val Val His Gln Val Glu
65                  70                  75                  80

Glu Cys Arg Val Lys Gly Pro Gly Ile Ser Lys Phe Val Gln Lys Val
            85                  90                  95

Asn Glu Ile Gly Ile Tyr Leu Thr Asp Cys Met Glu Arg Ala Arg Glu
            100                 105                 110

Val Ile Pro Arg Ser Gln His Gln Glu Thr Pro Val Tyr Leu Gly Ala
            115                 120                 125

Thr Ala Gly Met Arg Leu Leu Arg Met Glu Ser Glu Glu Leu Ala Asp
            130                 135                 140

Arg Val Leu Asp Val Val Glu Arg Ser Leu Ser Asn Tyr Pro Phe Asp
145                 150                 155                 160

Phe Gln Gly Ala Arg Ile Ile Thr Gly Gln Glu Glu Gly Ala Tyr Gly
            165                 170                 175

Trp Ile Thr Ile Asn Tyr Leu Leu Gly Lys Phe Ser Gln Lys Thr Arg
            180                 185                 190

Trp Phe Ser Ile Val Pro Tyr Glu Thr Asn Asn Gln Glu Thr Phe Gly
            195                 200                 205

Ala Leu Asp Leu Gly Gly Ala Ser Thr Gln Val Thr Phe Val Pro Gln
            210                 215                 220
```

```
Asn Gln Thr Ile Glu Ser Pro Asp Asn Ala Leu Gln Phe Arg Leu Tyr
225                 230                 235                 240

Gly Lys Asp Tyr Asn Val Tyr Thr His Ser Phe Leu Cys Tyr Gly Lys
                245                 250                 255

Asp Gln Ala Leu Trp Gln Lys Leu Ala Lys Asp Ile Gln Val Ala Ser
            260                 265                 270

Asn Glu Ile Leu Arg Asp Pro Cys Phe His Pro Gly Tyr Lys Lys Val
        275                 280                 285

Val Asn Val Ser Asp Leu Tyr Lys Thr Pro Cys Thr Lys Arg Phe Glu
    290                 295                 300

Met Thr Leu Pro Phe Gln Gln Phe Glu Ile Gln Gly Ile Gly Asn Tyr
305                 310                 315                 320

Gln Gln Cys His Gln Ser Ile Leu Glu Leu Phe Asn Thr Ser Tyr Cys
                325                 330                 335

Pro Tyr Ser Gln Cys Ala Phe Asn Gly Ile Phe Leu Pro Pro Leu Gln
            340                 345                 350

Gly Asp Phe Gly Ala Phe Ser Ala Phe Tyr Phe Val Met Lys Phe Leu
        355                 360                 365

Asn Leu Thr Ser Glu Lys Val Ser Gln Glu Lys Val Thr Glu Met Met
    370                 375                 380

Lys Lys Phe Cys Ala Gln Pro Trp Glu Glu Ile Lys Thr Ser Tyr Ala
385                 390                 395                 400

Gly Val Lys Glu Lys Tyr Leu Ser Glu Tyr Cys Phe Ser Gly Thr Tyr
                405                 410                 415

Ile Leu Ser Leu Leu Leu Gln Gly Tyr His Phe Thr Ala Asp Ser Trp
            420                 425                 430

Glu His Ile His Phe Ile Gly Lys Ile Gln Gly Ser Asp Ala Gly Trp
        435                 440                 445

Thr Leu Gly Tyr Met Leu Asn Leu Thr Asn Met Ile Pro Ala Glu Gln
    450                 455                 460

Pro Leu Ser Thr Pro Leu Ser His Ser Thr
465                 470

<210> SEQ ID NO 29
<211> LENGTH: 473
<212> TYPE: PRT
<213> ORGANISM: Artificial Sequence
<220> FEATURE:
<223> OTHER INFORMATION: Description of Artificial Sequence: Fusion
      construct of human CD39

<400> SEQUENCE: 29

Met Ala Leu Trp Ile Asp Arg Met Gln Leu Leu Ser Cys Ile Ala Leu
1               5                   10                  15

Ser Leu Ala Leu Val Thr Asn Ser Ser Thr Lys Lys Thr Gln Leu Thr
            20                  25                  30

Ser Ser Thr Gln Asn Lys Ala Leu Pro Glu Asn Val Lys Tyr Gly Ile
        35                  40                  45

Val Leu Asp Ala Gly Ser Ser His Thr Ser Leu Tyr Ile Tyr Lys Trp
    50                  55                  60

Pro Ala Glu Lys Glu Asn Asp Thr Gly Val Val His Gln Val Glu Glu
65                  70                  75                  80

Cys Arg Val Lys Gly Pro Gly Ile Ser Lys Phe Val Gln Lys Val Asn
                85                  90                  95

Glu Ile Gly Ile Tyr Leu Thr Asp Cys Met Glu Arg Ala Arg Glu Val
            100                 105                 110
```

```
Ile Pro Arg Ser Gln His Gln Glu Thr Pro Val Tyr Leu Gly Ala Thr
            115                 120                 125
Ala Gly Met Arg Leu Leu Arg Met Glu Ser Glu Leu Ala Asp Arg
        130                 135                 140
Val Leu Asp Val Val Glu Arg Ser Leu Ser Asn Tyr Pro Phe Asp Phe
145                 150                 155                 160
Gln Gly Ala Arg Ile Ile Thr Gly Gln Glu Gly Ala Tyr Gly Trp
            165                 170                 175
Ile Thr Ile Asn Tyr Leu Leu Gly Lys Phe Ser Gln Lys Thr Arg Trp
        180                 185                 190
Phe Ser Ile Val Pro Tyr Glu Thr Asn Asn Gln Glu Thr Phe Gly Ala
            195                 200                 205
Leu Asp Leu Gly Gly Ala Ser Thr Gln Val Thr Phe Val Pro Gln Asn
        210                 215                 220
Gln Thr Ile Glu Ser Pro Asp Asn Ala Leu Gln Phe Arg Leu Tyr Gly
225                 230                 235                 240
Lys Asp Tyr Asn Val Tyr Thr His Ser Phe Leu Cys Tyr Gly Lys Asp
            245                 250                 255
Gln Ala Leu Trp Gln Lys Leu Ala Lys Asp Ile Gln Val Ala Ser Asn
        260                 265                 270
Glu Ile Leu Arg Asp Pro Cys Phe His Pro Gly Tyr Lys Lys Val Val
            275                 280                 285
Asn Val Ser Asp Leu Tyr Lys Thr Pro Cys Thr Lys Arg Phe Glu Met
        290                 295                 300
Thr Leu Pro Phe Gln Gln Phe Glu Ile Gln Gly Ile Gly Asn Tyr Gln
305                 310                 315                 320
Gln Cys His Gln Ser Ile Leu Glu Leu Phe Asn Thr Ser Tyr Cys Pro
            325                 330                 335
Tyr Ser Gln Cys Ala Phe Asn Gly Ile Phe Leu Pro Pro Leu Gln Gly
        340                 345                 350
Asp Phe Gly Ala Phe Ser Ala Phe Tyr Phe Val Met Lys Phe Leu Asn
            355                 360                 365
Leu Thr Ser Glu Lys Val Ser Gln Glu Lys Val Thr Glu Met Met Lys
        370                 375                 380
Lys Phe Cys Ala Gln Pro Trp Glu Glu Ile Lys Thr Ser Tyr Ala Gly
385                 390                 395                 400
Val Lys Glu Lys Tyr Leu Ser Glu Tyr Cys Phe Ser Gly Thr Tyr Ile
            405                 410                 415
Leu Ser Leu Leu Leu Gln Gly Tyr His Phe Thr Ala Asp Ser Trp Glu
        420                 425                 430
His Ile His Phe Ile Gly Lys Ile Gln Gly Ser Asp Ala Gly Trp Thr
            435                 440                 445
Leu Gly Tyr Met Leu Asn Leu Thr Asn Met Ile Pro Ala Glu Gln Pro
        450                 455                 460
Leu Ser Thr Pro Leu Ser His Ser Thr
465                 470

<210> SEQ ID NO 30
<211> LENGTH: 463
<212> TYPE: PRT
<213> ORGANISM: Artificial Sequence
<220> FEATURE:
<223> OTHER INFORMATION: Description of Artificial Sequence: Fusion
      construct of human CD39
```

-continued

<400> SEQUENCE: 30

```
Met Glu Thr Asp Thr Leu Leu Trp Val Leu Leu Trp Val Pro
 1               5                  10                  15

Gly Ser Thr Gly Ala Pro Thr Ser Thr Gln Asn Lys Ala Leu Pro Glu
             20                  25                  30

Asn Val Lys Tyr Gly Ile Val Leu Asp Ala Gly Ser Ser His Thr Ser
             35                  40                  45

Leu Tyr Ile Tyr Lys Trp Pro Ala Glu Lys Glu Asn Asp Thr Gly Val
         50                  55                  60

Val His Gln Val Glu Glu Cys Arg Val Lys Gly Pro Gly Ile Ser Lys
 65                  70                  75                  80

Phe Val Gln Lys Val Asn Glu Ile Gly Ile Tyr Leu Thr Asp Cys Met
                 85                  90                  95

Glu Arg Ala Arg Glu Val Ile Pro Arg Ser Gln His Gln Glu Thr Pro
            100                 105                 110

Val Tyr Leu Gly Ala Thr Ala Gly Met Arg Leu Leu Arg Met Glu Ser
            115                 120                 125

Glu Glu Leu Ala Asp Arg Val Leu Asp Val Val Glu Arg Ser Leu Ser
130                 135                 140

Asn Tyr Pro Phe Asp Phe Gln Gly Ala Arg Ile Ile Thr Gly Gln Glu
145                 150                 155                 160

Glu Gly Ala Tyr Gly Trp Ile Thr Ile Asn Tyr Leu Leu Gly Lys Phe
                165                 170                 175

Ser Gln Lys Thr Arg Trp Phe Ser Ile Val Pro Tyr Glu Thr Asn Asn
            180                 185                 190

Gln Glu Thr Phe Gly Ala Leu Asp Leu Gly Gly Ala Ser Thr Gln Val
            195                 200                 205

Thr Phe Val Pro Gln Asn Gln Thr Ile Glu Ser Pro Asp Asn Ala Leu
        210                 215                 220

Gln Phe Arg Leu Tyr Gly Lys Asp Tyr Asn Val Tyr Thr His Ser Phe
225                 230                 235                 240

Leu Cys Tyr Gly Lys Asp Gln Ala Leu Trp Gln Lys Leu Ala Lys Asp
                245                 250                 255

Ile Gln Val Ala Ser Asn Glu Ile Leu Arg Asp Pro Cys Phe His Pro
            260                 265                 270

Gly Tyr Lys Lys Val Val Asn Val Ser Asp Leu Tyr Lys Thr Pro Cys
        275                 280                 285

Thr Lys Arg Phe Glu Met Thr Leu Pro Phe Gln Gln Phe Glu Ile Gln
290                 295                 300

Gly Ile Gly Asn Tyr Gln Gln Cys His Gln Ser Ile Leu Glu Leu Phe
305                 310                 315                 320

Asn Thr Ser Tyr Cys Pro Tyr Ser Gln Cys Ala Phe Asn Gly Ile Phe
                325                 330                 335

Leu Pro Pro Leu Gln Gly Asp Phe Gly Ala Phe Ser Ala Phe Tyr Phe
            340                 345                 350

Val Met Lys Phe Leu Asn Leu Thr Ser Glu Lys Val Ser Gln Glu Lys
        355                 360                 365

Val Thr Glu Met Met Lys Lys Phe Cys Ala Gln Pro Trp Glu Glu Ile
370                 375                 380

Lys Thr Ser Tyr Ala Gly Val Lys Glu Lys Tyr Leu Ser Glu Tyr Cys
385                 390                 395                 400

Phe Ser Gly Thr Tyr Ile Leu Ser Leu Leu Leu Gln Gly Tyr His Phe
                405                 410                 415
```

```
Thr Ala Asp Ser Trp Glu His Ile His Phe Ile Gly Lys Ile Gln Gly
        420                 425                 430

Ser Asp Ala Gly Trp Thr Leu Gly Tyr Met Leu Asn Leu Thr Asn Met
        435                 440                 445

Ile Pro Ala Glu Gln Pro Leu Ser Thr Pro Leu Ser His Ser Thr
    450                 455                 460
```

<210> SEQ ID NO 31
<211> LENGTH: 58
<212> TYPE: PRT
<213> ORGANISM: Homo sapiens

<400> SEQUENCE: 31

```
Met Ala Thr Ser Trp Gly Thr Val Phe Phe Met Leu Val Val Ser Cys
 1               5                  10                  15

Val Cys Ser Ala Val Ser His Arg Asn Gln Gln Thr Trp Phe Glu Gly
            20                  25                  30

Ile Phe Leu Ser Ser Met Cys Pro Ile Asn Val Ser Ala Ser Thr Leu
        35                  40                  45

Tyr Gly Ile Met Phe Asp Ala Gly Ser Thr
    50                  55
```

<210> SEQ ID NO 32
<211> LENGTH: 11
<212> TYPE: PRT
<213> ORGANISM: artificial
<220> FEATURE:
<223> OTHER INFORMATION: linker sequence

<400> SEQUENCE: 32

```
Gly Gly Gly Gly Ser Gly Gly Gly Gly Ser
 1               5                  10
```

<210> SEQ ID NO 33
<211> LENGTH: 13
<212> TYPE: PRT
<213> ORGANISM: artificial
<220> FEATURE:
<223> OTHER INFORMATION: linker sequence

<400> SEQUENCE: 33

```
Gly Ala Gly Gly Ala Gly Ser Gly Gly Gly Gly Ser
 1               5                  10
```

<210> SEQ ID NO 34
<211> LENGTH: 10
<212> TYPE: PRT
<213> ORGANISM: artificial
<220> FEATURE:
<223> OTHER INFORMATION: linker sequence

<400> SEQUENCE: 34

```
Gly Gly Gly Gly Ser Gly Gly Gly Gly Ser
 1               5                  10
```

<210> SEQ ID NO 35
<211> LENGTH: 9
<212> TYPE: PRT
<213> ORGANISM: artificial
<220> FEATURE:
<223> OTHER INFORMATION: linker sequence

<400> SEQUENCE: 35

```
-continued

Gly Thr Pro Gly Thr Pro Gly Thr Pro
1               5

<210> SEQ ID NO 36
<211> LENGTH: 26
<212> TYPE: PRT
<213> ORGANISM: artificial
<220> FEATURE:
<223> OTHER INFORMATION: linker sequence

<400> SEQUENCE: 36

Gly Gly Gly Gly Ser Gly Gly Gly Gly Ser Gly Gly Gly Gly Ser Gly
1               5                   10                  15

Gly Gly Gly Ser Gly Gly Gly Gly Gly Ser
            20                  25

<210> SEQ ID NO 37
<211> LENGTH: 4
<212> TYPE: PRT
<213> ORGANISM: artificial
<220> FEATURE:
<223> OTHER INFORMATION: linker sequence

<400> SEQUENCE: 37

Thr Ser Ser Gly
1
```

METHODS OF INHIBITING PLATELET ACTIVATION AND RECRUITMENT

REFERENCE TO RELATED APPLICATIONS

The present application is related to U.S. Provisional Application Ser. Nos. 60/104,585, filed 16 Oct. 1998, 60/107,466, filed 6 Nov. 1998, and 60/149,010, filed 13 Aug. 1999.

FIELD OF THE INVENTION

This invention relates to soluble CD39 compounds and compositions, the preparation thereof, and the use thereof to inhibit platelet activation and recruitment in a mammal.

BACKGROUND OF THE INVENTION

CD39 is a cell-surface antigen that was originally identified as a marker for mature B cells, but is also expressed on less mature B cells, Epstein-Barr Virus-transformed B cells, activated T cells, endothelial cells and some myeloid cell lines (Dörken et al., in *Leukocyte Typing IV*; W. Knapp, B. Dörken, and W. R. Gilks, Eds; Oxford University Press, New York, N.Y.; pp. 89-90, 1989). Monoclonal antibodies against CD39 induce B cell homotypic adhesion, an activity that may be important in the regulation of immune function (Kansas and Tedder, *J. Immunol.* 147:4094-4102, 1991). Molecular cloning and characterization of CD39 indicated that it is unique cell surface molecule that contains two potential transmembrane regions and a hydrophobic segment within the putative extracellular domain (Maliszewski et al., *J. Immunol.* 153:3574, 1994). The amino acid sequence of CD39 was reported to exhibit some homology with a guanosine diphosphatase from yeast (Maliszewski et al., supra).

In 1996, an ATP diphosphohydrolase was cloned from potato tubers (Handa and Guidotti, *Biochem. Biophys. Res. Commun.* 218:916, 1996). The amino acid sequences of this and several other NTPases demonstrated a high degree of similarity, particularly within several small "apyrase conserved regions" (ACR). CD39 shares these conserved regions with soluble ATP-diphosphorylase from potato tubers, other apyrases and related enzymes. It was subsequently reported that native and recombinant full-length CD39 possess E-type ATP diphosphohydrolase (ATPDase) activity (Marcus et al., *J. Clin. Invest.* 99:1351, 1997); Kaczmarek et al., *J. Biol. Chem.* 271:33116, 1996); Wang and Guidotti, *J. Biol. Chem.* 271:9898, 1996). ATPDases degrade nucleoside tri- and/or diphosphates, but not monophosphates (Plesner, *Int. Rev. Cytol.* 158:141, 1995).

Vascular endothelial cells constituitively express a cell-surface ADPase (ecto-ATP diphosphohydrolase, apyrase, EC 3.6.1.5), one of at least 3 thromboregulatory systems which function in the maintenance of blood fluidity (Marcus and Safier, *FASEB J.* 7:516, 1983; Marcus et al., *J. Clin. Invest.* 88:1690, 1991). This ecto-ADPase, which belongs to the E-type ATPDase family, rapidly metabolizes ADP in the platelet releasate, terminating further platelet recruitment and aggregation.

Immunoprecipitation of HUVEC detergent lysates with anti-CD39 mAb resulted in complete capture of cell-associated ADPase activity, suggesting that CD39 is the only ecto-ADPase on endothelial cells (Marcus et al., *J. Clin. Invest.* 99:1351, 1997). In the same study, COS cell transfectants expressing recombinant CD39 at the cell surface totally inhibited ADP-induced platelet aggregation. Thus, CD39 plays a prominent role in thromboregulation (see also, Gayle et al., *J. Clin. Invest.*, 101:1851, 1998; WO96/30532).

Excessive platelet activation (i.e., stimulation by an agonist) and recruitment, leading to platelet aggression and vessel occlusion at sites of vascular injury in the coronary, carotid, and peripheral arteries, presents a major therapeutic challenge in cardiovascular medicine. Excessive platelet activation and recruitment is a contributing factor in clinical disorders including stroke, unstable angina, myocardial infarction, and restenosis following percutaneous coronary intervention including angioplasty, atherectomy, stent placement, and bypass surgery.

Glycoprotein IIb/IIIa an antagonists, such as the monoclonal antibody marketed as ReoPro® (Centocor Inc.), are presently under development for the inhibition of platelet aggregation in patients undergoing percutaneous coronary intervention, and in patients with acute coronary syndromes such as unstable angina and myocardial infarction. The activation glycoprotein IIb/IIIa receptors, however, is a late event in the cascade that leads to platelet aggregation.

There is a great need to identify additional therapeutic strategies and compositions for the pharmacological neutralization of platelet reactivity (activation, recruitment, aggregation). In particular, there is a need to identify compounds and compositions which target early portions of coagulation pathways such as the ADP-dependent activation and recruitment of platelets. There is, in fact, an urgent need to identify new strategies and compositions for the treatment of stroke, which is the third leading cause of death in the United States. In the case of stroke, an advantageous therapeutic agent will reduce intravascular thrombus burden and accompanying neurological defects without increasing intracerebral hemorrhage.

SUMMARY OF THE INVENTION

Soluble forms of CD39 having apyrase activity constitute a novel approach to the prevention and/or treatment of disease. The present invention provides soluble CD39 polypeptides and nucleic acids, compositions comprising a pharmaceutically acceptable carrier and a soluble CD39 polypeptide, and methods of making and using soluble CD39 polypeptides having apyrase activity. The effectiveness of soluble CD39 polypeptides have been demonstrated in vitro, ex vivo, and in vivo.

The invention is directed to soluble CD39 polypeptides selected from the group consisting of: (a) polypeptides having an amino acid sequence as set forth in FIG. 1 (SEQ ID NO:2) wherein the amino terminus is selected from the group consisting of amino acids 36-44, and the carboxy terminus is selected from the group consisting of amino acids 471-478: (b) fragments of the polypeptides of (a) wherein said fragments have apyrase activity: (c) variants of the polypeptides of (a) or (b), wherein said variants have apyrase activity; aid (d) fusion polypeptides comprising the polypeptides of (a), (b), or (c), wherein said fusion polypeptides have apyrase activity. The invention provides compositions comprising a pharmaceutically acceptable carrier and a soluble CD39 polypeptide.

The invention is also directed to nucleic acids encoding a soluble CD39 polypeptide. The invention provides DNAs, vectors, recombinant cells, and recombinant methods for the production of soluble CD39 polypeptides.

The invention is further directed to the use of soluble CD39 polypeptides for inhibiting platelet activation and recruitment, for inhibiting angiogenesis, or for degrading nucleoside tri- and/or di-phosphates in a mammal in need of such treatment. The invention encompasses the use of a soluble CD39 polypeptide for the preparation of a medicament for inhibiting platelet activation and platelet recruitment, for inhibiting angiogenesis, or for degrading nucleoside tri- and/or di-phosphates in a mammal in need of such treatment. These and other aspects of the present invention will become evident upon reference to the following drawings, examples, and detailed description.

BRIEF DESCRIPTION OF THE DRAWINGS

FIG. 1 shows the predicted amino acid sequence (SEQ ID NO:2) of human CD39. The predicted amino acid sequence contains 6 potential N-linked glycosylation sites (double underline), and 11 cysteine residues (bold face). The two predicted transmembrane regions are underlined (single underline).

FIG. 5 shows the immunoaffinity purification and characterization of soluble CD39 (solCD39).

FIG. 8 shows a comparison of platelet reactivity as modulated by different agonists and inhibitors. The effects of CM from cells expressing solCD39 on platelet aggregation induced by 5 µM ADP (FIG. 8A) and collagen (FIG. 8B) were compared in PRP and PRP treated with 10 µM indomethacin. In FIG. 8B, 1 µg/ml collagen was used in the upper samples and 3.3 µg/ml in the lower (indomethacin-treated) samples. FIG. 8C shows the inhibition of collagen-induced aggregation by increasing quantities of solCD39 in PRP from a donor who had ingested aspirin. The arrows indicate the addition of agonist. Data are presented as relative light transmission vs time (4 min.).

FIG. 9 shows the effect of FSBA-treated solCD39 on platelet reactivity.

DETAILED DESCRIPTION OF THE INVENTION

Figure 2:
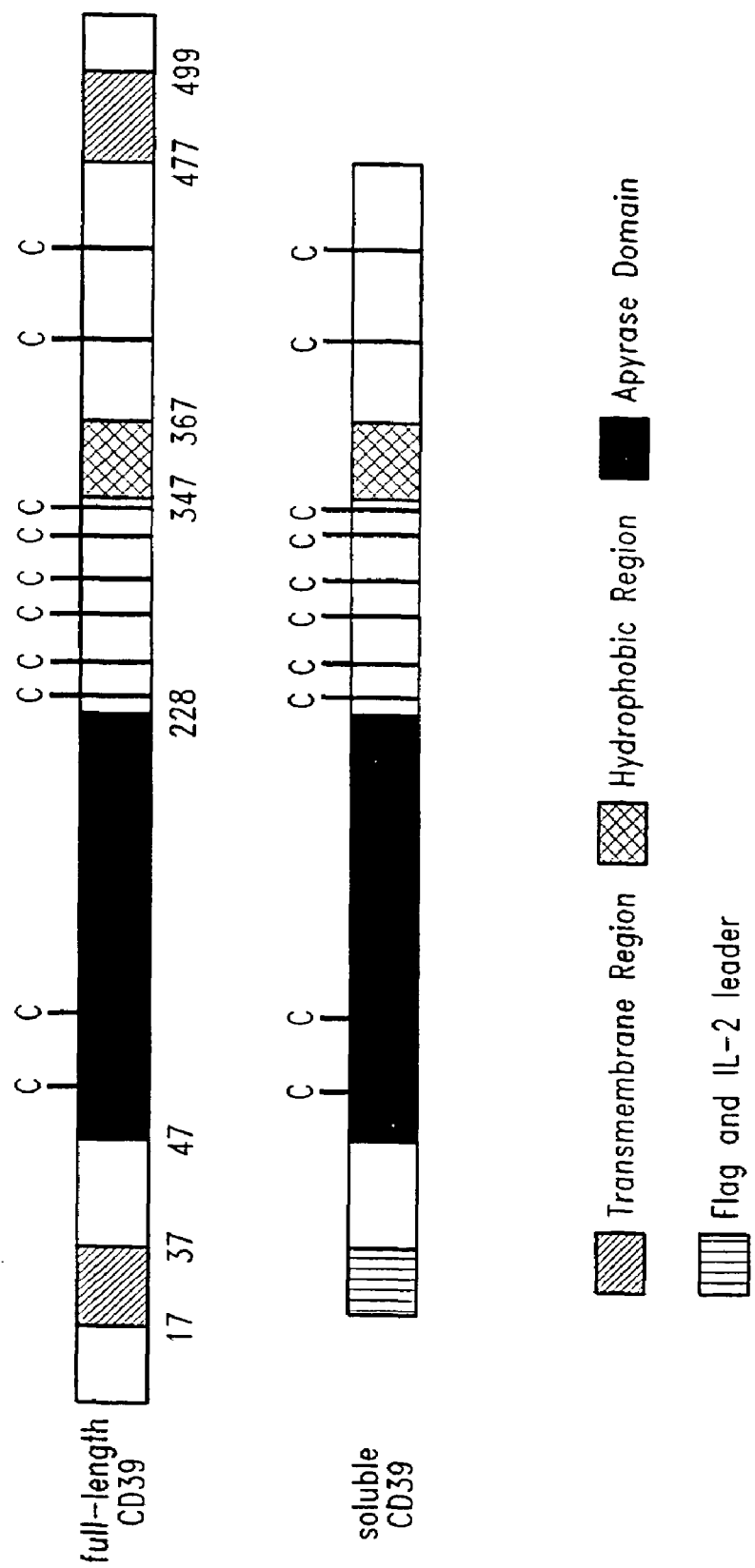
FIG. 2 shows the domain structure of full length CD39 and of an engineered soluble form of CD39. The locations of transmembrane regions near the amino- and carboxy-termini, the centrally located hydrophobic sequence, and a section containing the four putative apyrase conserved regions (ACR) are indicated. Cysteine residues are marked as "C". The soluble CD39 contains a FLAG® peptide and new leader sequence and lacks the two transmembrane regions.

A cDNA encoding the cell-surface molecule CD39 has been isolated, cloned and sequenced. The nucleic acid sequence and predicted amino acid sequence of this cDNA are shown in SEQ ID NO:1 and SEQ ID NO:2. The present invention provides methods of using soluble forms of CD39, which were constructed by removing the amino- and carboxy-terminal transmembrane domains. Soluble CD39 retains the capacity of wildtype CD39 to metabolize ATP and ADP at physiologically relevant concentrations as well as the ability to block and reverse ADP-induced platelet activation and recruitment, including platelet aggregation. The use of soluble forms of CD39 is advantageous because purification of the polypeptides from recombinant host cells is facilitated, and because soluble polypeptides are generally more suitable than membrane-bound forms for clinical administration. Because CD39 inhibits platelet activation and recruitment, and therefore platelet aggregation, the present invention provides methods and compositions for inhibiting formation of a thrombus at a site in a mammal at which platelets are inappropriately activated, methods for use in controlling platelet reactivity, thereby regulating the hemostatic and thrombotic processes, and methods of inhibiting and/or reversing platelet aggregation.

A. Hemostasis

Hemostasis is defined as the arrest of bleeding from damaged blood vessels, and results from a sequence of physiologic and biochemical events. At least three interacting biological systems are involved in hemostasis: components of the blood vessels (such as the subendothelial matrix), platelets, and plasma proteins (Marcus, A. J.: *Disorders of Hemostasis*, Ratnoff and Forbes, eds., W.B. Saunders, Philadelphia, 1996; pages 79-137; Marcus, A. J.: *Platelet Activation*, in: *Atherosclerosis and Coronary Artery Disease*, vol. 1, Fuster, Ross and Topol, eds., Lipincott-Raven, Philadelphia, 1996; pages 607-637). A defect or defects in one or more of these systems can result in hemorrhagic disorder; conversely, the inappropriate activation of hemostasis culminates in development of arterial or venous thrombosis.

When a blood vessel is injured, it contracts, exposing subendothelial matrix components such as collagen, von Willebrand factor, fibronectin, thrombospondin, laminin, and microfibrils. Platelets adhere to, and are activated by, these components; collagen is an especially effective agonist for platelet activation. At least four physiologic events are initiated by platelet-collagen contact: the platelets release biologically active compounds; they express P-selectin on their cell surface (where it mediates adhesion of neutrophils, monocytes and subsets of lymphocytes); the platelet eicosanoid pathway is activated (starting with the liberation of arachidonic acid which forms prostaglandin $H_2$); and the platelets undergo a drastic change in shape, from smooth disks to spiny spheres.

The biologically active compounds released by platelets are numerous, and multi-functional. Included in this group of components are serotonin, ATP, ADP, calcium, adhesive proteins (fibrinogen, fibronectin, thrombospondin, vitronectin, von Willebrand factor), growth factors (platelet-derived growth factor, transforming growth factor-β, platelet factor 4) and coagulation factors (factor V, high-molecular weight kininogen, factor XI, protein S and plasminogen activator inhibitor-I (PAI-I)). Some of these compounds play a role in the recruitment of additional platelets and/or other cells such as neutrophils and monocytes to the site of activation, whereas others are involved in feedback mechanisms to down-regulate excessive thrombus formation.

At least three separate endothelial thromboregulatory systems exist: the eicosanoids including the prostaglandins $PGI_1$ and $PGD_2$; endothelium-dependent relaxing factor (EDRF/NO); and the ecto-nucleotidase ATP-diphosphohydrolase (ATPDase) which has both ADPase and ATPase activities. While collagen and thrombin are the prime inducers of platelet secretion, ADP is the most important agonist of platelet aggregation present in the platelet releasate. Catabolism of ADP to AMP by the ecto-ADPase blocks further recruitment of additional platelets to the site, reverses the aggregation response and blocks subsequent thrombus response.

Ecto-nucleotidase activity is demonstrable in vitro in an aggregrometry system in which EDRF/NO effects and $PGI_2$ production are blocked by hemoglobin and aspirin respectively (Marcus and Safier, *FASEB J* 7:516; 1993). In this system, loss of platelet stimulatory activity in the supernatant fluid correlates with ADP catabolism. An ADPase activity has been identified in the membrane fraction of human endothelial cells; enzyme activity detected by polyacrylamide gel electrophoresis indicated both ATPase and ADPase (Marcus et al., *Clin. Res.* 40:226A (abstract), 1992).

B. Utility of the Claimed Invention

Significant research efforts are directed to the discovery and characterization of platelet aggregation inhibitors because of the potential utility of such inhibitors in treating occlusive vascular disease. For example, WO 95/12412 discloses platelet-specific chimeric antibodies and methods of using the same in treating various thrombotic disorders. A prototype description of the efforts to develop this therapeutic agent and obtain approval for its use as a human therapeutic agent (generic name: abciximab, trade name: ReoPro®) was described by B. S. Coller in *Circulation* 92:2373 (1995).

CD39 is an ecto-ADPase (apyrase) located on the surface of endothelial cells. This enzyme is mainly responsible for the maintenance of blood fluidity, thus maintaining platelets in the baseline (resting) state. This is accomplished by metabolism of the major platelet agonist, adenosine diphosphate, to adenosine monophosphate, which is not an agonist. Because ADP is the most important agonist of platelet aggregation, and is present in platelet releasate, a substance which catabolizes ADP is useful in treating or preventing disease states that involve inappropriate aggregation of platelets.

Examples of the therapeutic uses of soluble CD39 and compositions thereof include the treatment of individuals who suffer from coronary artery disease or injury following myocardial infarction, atherosclerosis, arteriosclerosis, preeclampsia, embolism, platelet-associated ischemic disorders including lung ischemia, coronary ischemia, and cerebral ischemia, and for the prevention of reocclusion following thrombosis, thrombotic disorders including coronary artery thrombosis, cerebral artery thrombosis, intracardiac thrombosis, peripheral artery thrombosis, venous thrombosis, and thrombosis and coagulopathies associated with exposure to a foreign or injured tissue surface, in combination with angioplasty, carotid endarterectomy, anastomosis of vascular grafts, and chronic cardiovascular devices such as in-dwelling catheters or shunts. Other instances in which it would be useful to inhibit increased ADP release due to increased platelet stimulation would be in individuals at high risk for thrombus formation or reformation (severe arteriosclerosis), and inhibition of occlusion, reocclusion, stenosis and/or restenosis of blood vessels. Individuals who will benefit from therapies that involve inhibiting ADP-induced aggregation of platelets include those at risk for advanced coronary artery disease, and those that are or will be undergoing angioplasty procedures (i.e., balloon angioplasty, laser angioplasty, coronary atherectomy and similar techniques). Inhibition of platelet aggregation will also be useful in individuals undergoing surgery that has a high risk of thrombus formation (i.e., coronary bypass surgery, insertion of a prosthetic valve or vessel and the like), and in the prevention or treatment of deep venous thrombosis (DVT), pulmonary embolism (PE), transient ischemic attacks (TIAs) and other related conditions where arterial occlusion is the common underlying feature. In addition, the ability of CD39 to block platelet activation and recruitment is useful for preventing stroke and for treating patients experiencing stroke due to vascular occlusion. In particular, the methods, compounds, and compositions of the present invention have the ability to inhibit microvascular thrombosis, improve postischemic cerebral blood flow, and reduce cerebral infarction volumes and neurological deficit without inducing intracerebral hemorrhage, in stroke. Soluble CD39 and compositions thereof according to the present invention can also be administered in any other therapeutic setting where it would be useful to degrade nucleoside tri- and/or diphosphates. As an example, soluble CD39 may be used as an anti-neoplastic agent to inhibit angiogenesis and/or prevent the survival benefits that ATP provides to tumor cells, or to treat other diseases or conditions mediated by angiogenesis such as occular neovascularization.

Soluble CD39 polypeptides also have many non-therapeutic uses, since they may be used in any application where soluble ATPase and/or ADPase activity is advantageous. As an example, soluble CD39 polypeptides may be used in compositions for preserving platelets such as those described by Gepner-Puszkin (U.S. Pat. No. 5,378,601). As another example, soluble CD39 polypeptides may be used in pyrophosphate-based DNA sequencing methodologies such as those described by Ronaghi et al. (*Science* 281:336, 1998). As a further example, soluble CD39 polypeptides can be used to screen for apyrase inhibitors.

C. CD39 Polypeptides

The molecular cloning and structural characterization of CD39 is presented in Maliszewski et al. (*J. Immunol.* 153:3574, 1994). CD39 contains two putative transmembrane regions, near the amino and carboxy termini, which may serve to anchor the native protein in the cell membrane. The portion of the molecule between the transmembrane regions is external to the cell. As used herein, the term "CD39 polypeptides" includes CD39, homologs of CD39, variants, fragments, and derivatives of CD39, fusion polypeptides comprising CD39, and soluble forms of CD39 polypeptides.

Soluble polypeptides are polypeptides that are capable of being secreted from the cells in which they are expressed. A secreted soluble polypeptide may be identified (and distinguished from its non-soluble membrane-bound counterparts) by separating intact cells which express the desired polypeptide from the culture medium, e.g., by centrifugation, and assaying the medium (supernatant) for the presence of the desired polypeptide. The presence of the desired polypeptide in the medium indicates that the polypeptide was secreted from the cells and thus is a soluble form of the polypeptide. The use of soluble forms of CD39 is advantageous for many applications. Purification of the polypeptides from recombinant host cells is facilitated, since the soluble polypeptides are secreted from the cells. Moreover, soluble polypeptides are generally more suitable than membrane-bound forms for parenteral administration and for many enzymatic procedures.

Apyrase activity resides in the extracellular domain of CD39. Thus, for applications requiring biological activity, useful CD39 polypeptides include soluble forms of CD39 such as those having an amino terminus selected from the group consisting of amino acids 36-44 of SEQ ID NO:2, and a carboxy terminus selected from the group consisting of amino acids 471-478 of SEQ ID NO:2, and which exhibit CD39 biological activity. Soluble CD39 polypeptides also include those polypeptides which include part of either or both of the transmembrane regions, provided that the soluble CD39 polypeptide is capable of being secreted from a cell, and retains CD39 biological activity. Soluble CD39 polypeptides further include oligomers or fusion polypeptides comprising the extracellular portion of CD39, and fragments of any of these polypeptides that have biological activity.

The term "biological activity," as used herein, includes apyrase enzymatic activity as well as the ex vivo and in vivo activities of CD39. Apyrases catalyze the hydrolysis of nucleoside tri- and/or di-phosphates, but a given apyrase may display different relative specificities for either nucleoside triphosphates or nucleoside diphosphates. Biological activity of soluble forms of CD39 may be determined, for example, in an ectonucleotidase or apyrase assay (e.g. ATPase or ADPase assays), or in an assay that measures inhibition of platelet aggregation. Exemplary assays are disclosed herein; those of skill in the art will appreciate that other, similar types of assays can be used to measure biological activity.

Among the soluble CD39 polypeptides provided herein are variants (also referred to as analogs) of native CD39 polypeptides that retain a biological activity of CD39. Such variants include polypeptides that are substantially homologous to native CD39, but which have an amino acid sequence different from that of a native CD39 because of one or more deletions, insertions or substitutions. Particular embodiments include, but are not limited to, CD39 polypeptides that comprise from one to ten deletions, insertions or substitutions of amino acid residues, when compared to a native CD39 sequence. The CD39-encoding DNAs of the present invention include variants that differ from a native CD39 DNA sequence because of one or more deletions, insertions or substitutions, but that encode a biologically active polypeptide. Included as variants of CD39 polypeptides are those variants that are naturally occurring, such as allelic forms and alternatively spliced forms, as well as variants that have been constructed by modifying the amino acid sequence of a CD39 polypeptide or the nucleotide sequence of a nucleic acid encoding a CD39 polypeptide.

Generally, substitutions for one or more amino acids present in the native polypeptide should be made conservatively. Examples of conservative substitutions include substitution of amino acids outside of the active domain(s), and substitution of amino acids that do not alter the secondary and/or tertiary structure of CD39. Additional examples include substituting one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are known in the art.

When a deletion or insertion strategy is adopted, the potential effect of the deletion or insertion on biological activity must be considered. Subunits of the inventive polypeptides may be constructed by deleting terminal or internal residues or sequences. Additional guidance as to the types of mutations that can be made is provided by a comparison of the sequence of CD39 to polypeptides that have similar structures, as well as by performing structural analysis of the inventive polypeptides.

The native sequence of full length CD39 is set forth in FIG. 1 (SEQ ID NO:2). In some preferred embodiments the CD39 variants are at least about 70% identical in amino acid sequence to the amino acid sequence of native CD39 as set forth in the sequence listing; in some preferred embodiments the CD39 variants are at least about 80% identical in amino acid sequence to the amino acid sequence of native CD39 as set forth in the sequence listing. In some more preferred embodiments the variants of CD39 are at least about 90% identical in amino acid sequence to the amino acid sequence of native CD39 as set forth in the sequence listing; in some more preferred embodiments the variants of CD39 are at least about 95% identical in amino acid sequence to the amino acid sequence of native CD39 as set forth in the sequence listing. In some most preferred embodiments, variants of CD39 are at least about 98% identical in amino acid sequence to the amino acid sequence of native CD39 as set forth in the sequence listing; in some most preferred embodiments, variants of CD39 are at least about 99% identical in amino acid sequence to the amino acid sequence of native CD39 as set forth in the sequence listing. Percent identity, in the case of both polypeptides and nucleic acids, may be determined by visual inspection. Percent identity may be determined using the alignment method of Needleman and Wunsch (J. Mol. Biol. 48:443, 1970) as revised by Smith and Waterman (Adv. Appl. Math 2:482, 1981. Preferably, percent identity is determined by using a computer program, for example, the GAP computer program version 10.x available from the Genetics Computer Group (GCG; Madison, Wis., see also Devereux et al., Nucl. Acids Res. 12:387, 1984). The preferred default parameters for the GAP program include: (1) a unary comparison matrix (containing a value of 1 for identities and 0 for non-identities) for nucleotides, and the weighted comparison matrix of Gribskov and Burgess, Nucl. Acids Res. 14:6745, 1986, as described by Schwartz and Dayhoff, eds., Atlas of Protein Sequence and Structure, National Biomedical Research Foundation, pp. 353-358, 1979 for amino acids; (2) a penalty of 30 (amino acids) or 50 (nucleotides) for each gap and an additional 1 (amino acids) or 3 (nucleotides) penalty for each symbol in each gap; (3) no penalty for end gaps; and (4) no maximum penalty for long gaps. Other programs used by one skilled in the art of sequence comparison may also be used. For fragments of CD39, the percent identity is calculated based on that portion of CD39 that is present in the fragment.

The primary amino acid structure of soluble CD39 may be modified to create CD39 derivatives by forming covalent or aggregative conjugates with other chemical moieties, such as glycosyl groups, lipids, phosphate, acetyl groups and the like. Covalent derivatives of CD39 are prepared by linking particular functional groups to CD39 amino acid side chains or at the N-terminus or C-terminus of a CD39 polypeptide or the extracellular domain thereof. CD39 derivatives also include CD39 polypeptides bound to various insoluble substrates, including cyanogen bromide-activated agarose structures, or similar agarose structures, or adsorbed to polyolefin surfaces (with or without glutaraldehyde cross-linking).

Fusion polypeptides of soluble CD39 within the scope of this invention include covalent or aggregative conjugates of CD39 or its fragments with other polypeptides, such as by synthesis in recombinant culture as N-terminal or C-terminal fusions. One class of fusion polypeptides are discussed below in connection with soluble CD39 oligomers. As another example, a fusion polypeptide may comprise a signal peptide (which is also variously referred to as a signal sequence, signal, leader peptide, leader sequence, or leader) at the N-terminal region or C-terminal region of a CD39 polypeptide which co-translationally or post-translationally directs transfer of the polypeptide from its site of synthesis to a site inside or outside of the cell membrane or cell wall (e.g. the α-factor leader of Saccharomyces; several leader sequences are discussed in the examples that follow). It is particularly advantageous to fuse a signal peptide that promotes extracellular secretion to the N-terminus of a soluble CD39 polypeptide. In this case, the signal peptide is typically cleaved upon secretion of the soluble CD39 from the cell.

In a particularly preferred embodiment, one or more amino acids are added to the N-terminus of a soluble CD39 polypeptide in order to improve the expression levels and/or stability of the CD39 polypeptide. The one or more amino acids include an Ala residue, fragments derived from the N-terminus of another member of the CD39 family (e.g., CD39L2, CD39L3, CD39L4) or from another polypeptide such as IL-2, and other peptides, either naturally-occurring or designed based upon structural predictions, capable of adopting a stable secondary structure.

In a most preferred embodiment, a soluble CD39 polypeptide is initially synthesized as a fusion polypeptide comprising: (a) a signal peptide that promotes extracellular secretion of the soluble CD39 from the cell, the signal peptide being cleaved upon secretion, (b) one or more amino acids added to the N-terminus of the soluble CD39 polypeptide in order to improve expression levels and/or stability, and (c) a fragment of CD39 that possesses biological activity.

CD39 fusion polypeptides can also comprise polypeptides added to provide novel polyfunctional entities. Further, soluble CD39-containing fusion polypeptides can comprise peptides added to facilitate purification and identification of soluble CD39. Such peptides include, for example, poly-His or the antigenic identification peptides described in U.S. Pat. No. 5,011,912 and in Hopp et al., *Bio/Technology* 6:1204, 1988. One such peptide is the FLAG® peptide, Asp-Tyr-Lys-Asp-Asp-Asp-Asp-Lys (SEQ ID NO: 10), which is highly antigenic and provides an epitope reversibly bound by a specific monoclonal antibody, enabling rapid assay and facile purification of expressed recombinant polypeptide. A murine hybridoma designated 4E11 produces a monoclonal antibody that binds the FLAG® peptide in the presence of certain divalent metal cations, as described in U.S. Pat. No. 5,011,912, hereby incorporated by reference. The 4E11 hybridoma cell line has been deposited with the American Type Culture Collection under accession no. HB 9259. Monoclonal antibodies that bind the FLAG® peptide are available from Eastman Kodak Co., Scientific Imaging Systems Division, New Haven, Conn.

Another particularly useful class of fusion polypeptides includes those that allow localization or concentration of CD39 at a site of platelet activation and recruitment. Such fusion polypeptides comprise a moiety that specifically binds activated platelets and CD39, and can be prepared using recombinant DNA technology, or by using standard techniques for conjugation of polypeptides. For example, WO 95/12412 discloses platelet-specific chimeric antibodies and methods of using the same in treating various thrombotic disorders. These antibodies, or other platelet specific antibodies (for example, antibodies to P-selectin/CD62), are useful in forming fusion polypeptides with CD39. Moreover, humanized or single chain antibodies can be prepared, based on such platelet specific antibodies.

Counterstructure molecules (molecules that specifically bind polypeptides expressed on the cell surface of activated platelets) and fragments thereof that bind to platelets are also useful in forming fusion polypeptides that bind specifically to activated platelets. Exemplary counterstructures include ligands for P-selectin/CD62 (see, i.e., Varki A., *Proc Natl Acad Sci USA* 91:7390, 1994; Sammar et al., *Int Immunol* 6:1027, 1994; Lenter et al., *J Cell Biol* 125:471, 1994).

Encompassed by the present invention are oligomers that contain CD39 polypeptides. CD39 oligomers may be in the form of covalently-linked or non-covalently-linked multimers, including dimers, trimers, or higher oligomers. Oligomers may be linked by disulfide bonds formed between cysteine residues on different CD39 polypeptides. Alternatively, oligomers may be formed by constructing fusion polypeptides of CD39 and the Fc region of an immunoglobulin molecule, such as human $IgG_1$, to yield a CD39/Fc fusion polypeptide. The term "Fc polypeptide" as used herein includes native and mutein forms of polypeptides derived from the Fc region of an antibody. Truncated forms of such polypeptides containing the hinge region that promotes dimerization are also included. One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., (*EMBO J.* 13:3992-4001, 1994). The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors. The CD39/Fc fusion polypeptides are allowed to assemble much like heavy chains of an antibody molecule to form divalent CD39. If fusion polypeptides are made with both heavy and light chains of an antibody, it is possible to form a CD39 oligomer with as many as four CD39 extracellular regions.

In some embodiments of the invention, oligomers comprising multiple CD39 polypeptides are joined via covalent or non-covalent interactions between peptide moieties fused to the C39-polypeptides. Such peptide moieties may be peptide linkers (spacers), or peptides that have the property of promoting oligomerization. Leucine zippers and certain polypeptides derived from antibodies are among the peptides that can promote oligomerization of polypeptides.

The present invention comprises fusion polypeptides with or without spacer amino acid linking groups. For example, two soluble CD39 domains can be linked with a linker sequence, such as $(Gly)_4Ser(Gly)_5Ser$ (SEQ ID NO:32), which is described in U.S. Pat. No. 5,073,627. Other linker sequences include, for example, GlyAlaGlyGlyAlaGlySer $(Gly)_5Ser$ (SEQ ID NO:33), $(Gly_4Ser)_2$ (SEQ ID NO:34), $(GlyThrPro)_3$ (SEQ ID NO:35), and $(Gly_4Ser)_3$ $Gly_4SerGly_5Ser$ (SEQ ID NO:36). Alternatively, CD39 can be linked to another polypeptide (non-CD39) with or without a spacer amino acid linking group. As shown in Example 9, ThrSerSer or ThrSerSerGly (SEQ ID NO:37) linkers may be used to fuse IL2 residues to soluble CD39. For the expression of soluble CD39, the inventors have made the surprising and unexpected discovery that the fusion of 12 amino acids from the N-terminus of mature human IL2 to the solCD39 coding region, results in high levels of both expression and activity in the supernatants of transfected cells. Among the particularly preferred embodiments of the invention, therefore, are soluble CD39 polypeptides having an amino acid sequence SEQ ID NO:6 and nucleic acids, such as SEQ ID NO:5, that encode soluble CD39 polypeptides having an amino acid sequence SEQ ID NO:6.

The present invention further includes soluble CD39 polypeptides with or without associated native-pattern glycosylation. CD39 expressed in yeast or mammalian expression systems (e.g., COS-7 cells) may be similar to or significantly different from a native CD39 polypeptide in molecular weight and glycosylation pattern, depending upon the choice of expression system. Expression of CD39 polypeptides in bacterial expression systems, such as *E. coli*, provides non-glycosylated molecules.

Different host cells may process polypeptides differentially, resulting in heterogeneous mixtures of polypeptides with variable N- or C-termini. Expression of soluble CD39 polypeptides in microbial expression systems, such as *E. coli*, generally provides a homogeneous polypeptide preparation. Polypeptides may be differentially processed by a eukaryotic cell, resulting in variable N- and C-termini, and hence yield a heterogeneous polypeptide preparation. The present invention includes polypeptides, produced by eukaryotic host cells, which have variable N-termini or C-termini. In one embodiment of the inventive CD39 polypeptides, the amino and carboxy termini can be about five amino acids different from those disclosed herein.

The skilled artisan will also recognize that the position(s) at which a signal peptide is cleaved may differ from that predicted by computer program, and may vary according to such factors as the type of host cells employed in expressing a recombinant soluble CD39 polypeptide. A polypeptide preparation according to the invention may therefore include a mixture of polypeptide molecules having different N-terminal amino acids, resulting from cleavage of the signal peptide at more than one site.

D. Nucleic Acids

The invention encompasses full length nucleic acid molecules encoding soluble CD39 as well as isolated fragments and oligonucleotides derived from the nucleotide sequence of SEQ ID NO:1. Such nucleic acid sequences may include nucleotides 178-1494 of SEQ ID NO:1 or a fragment thereof, and DNA and/or RNA sequences that hybridize to the coding region of the nucleotide sequence of SEQ ID NO:1, or its complement, under conditions of moderate stringency, and which encode polypeptides or fragments thereof of the invention.

Nucleic acid sequences encoding soluble CD39 polypeptides having altered glycosylation sites, deleted or substituted Cys residues, or modified proteolytic cleavage sites, nucleic acid sequences encoding sub-units of CD39 polypeptides or fusion polypeptides of CD39 with other peptides, allelic variants of CD39, mammalian homologs of CD39, and nucleic acid sequences encoding CD39 polypeptides derived from alternative mRNA constructs, or those that encode peptide having substituted or additional amino acids, are examples of nucleic acid sequences according to the invention.

Due to degeneracy of the genetic code, there can be considerable variation in nucleotide sequences encoding the same amino acid sequence. Included as embodiments of the invention are sequences capable of hybridizing under moderately stringent conditions (e.g., prewashing solution of 5×SSC, 0.5% SDS, 1.0 mM EDTA (pH 8.0) and hybridization conditions of 50° C., 5×SSC, overnight) to the DNA sequences encoding soluble CD39, and other sequences which are degenerate to those which encode soluble CD39. The skilled artisan can determine additional combinations of salt and temperature that constitute moderate hybridization stringency. Conditions of higher stringency include higher temperatures for hybridization and post-hybridization washes, and/or lower salt concentration.

In a preferred embodiment, CD39 DNAs include those that encode polypeptides that are at least about 70% or at least 80% identical in amino acid sequence to the amino acid sequence of native CD39 polypeptide as set forth in SEQ ID NO:1. In a more preferred embodiment, the encoded variants of CD39 are at least about 90% or at least about 95% identical in amino acid sequence to the native form of CD39; in a most preferred embodiment, the encoded variants of CD39 are at least about 98% or at least about 99% identical in amino acid sequence to the native form of CD39. For DNAs that encode a fragment of CD39, percent identity of the fragment is based on percent identity to the corresponding portion of full-length CD39.

Mutations can be introduced into nucleic acids by synthesizing oligonucleotides containing a mutant sequence, flanked by restriction sites enabling ligation to fragments of the native sequence. Following ligation, the resulting reconstructed sequence encodes a variant having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, January 1985, 12-19); Smith et al. (*Genetic Engineering: Principles and Methods*, Plenum Press, 1981); and U.S. Pat. Nos. 4,518,584 and 4,737,462 disclose suitable techniques, and are incorporated by reference herein.

The well known polymerase chain reaction (PCR) procedure also may be employed to generate and amplify a DNA sequence encoding a desired polypeptide or fragment thereof. Oligonucleotides that define the desired termini of the DNA fragment are employed as 5' and 3' primers. The oligonucleotides may additionally contain recognition sites for restriction endonucleases to facilitate insertion of the amplified DNA fragment into an expression vector. PCR techniques are described in Saiki et al., *Science* 239:487, 1988; *Recombinant DNA Methodology*, Wu et al., eds., Academic Press, Inc., San Diego, 1989, pp. 189-196; and *PCR Protocols: A Guide to Methods and Applications*, Innis et al., eds., Academic Press, Inc., 1990.

DNA sequences that encode CD39 polypeptides comprising various additions or substitutions of amino acid residues or sequences, or deletions of terminal or internal residues or sequences not needed for biological activity can be prepared. For example, N-glycosylation sites can be modified to preclude glycosylation while allowing expression of a homogeneous, reduced carbohydrate variant using yeast expression systems. N-glycosylation sites in eukaryotic polypeptides are characterized by an amino acid triplet Asn-X-Y, wherein X is any amino acid except Pro and Y is Ser or Thr. Appropriate modifications to the nucleotide sequence encoding this triplet will result in substitutions, additions or deletions that prevent attachment of carbohydrate residues at the Asn side chain.

In another example, sequences encoding Cys residues can be altered to cause the Cys residues to be deleted or replaced with other amino acids, preventing formation of incorrect intramolecular disulfide bridges upon renaturation. Thus, Cys residues may be replaced with another amino acid or deleted without affecting polypeptide tertiary structure or disulfide bond formation.

Other approaches to mutagenesis involve modification of sequences encoding dibasic amino acid residues to enhance expression in yeast systems in which KEX2 protease activity is present. Other variants are prepared by modification of adjacent dibasic amino acid residues, to enhance expression in yeast systems in which KEX2 protease activity is present. EP 212,914 discloses the use of site-specific mutagenesis to inactivate KEX2 protease processing sites in a polypeptide. KEX2 protease processing sites are inactivated by deleting, adding or substituting residues to alter Arg-Arg, Arg-Lys, and Lys-Arg pairs to eliminate the occurrence of these adjacent basic residues. Similar modification may be made to sequences encoding sites recognized and cleaved by other proteolytic enzymes. Sub-units of a CD39 polypeptide may be constructed by deleting sequences encoding terminal or internal residues or sequences not necessary for biological activity. Sequences encoding fusion polypeptides as described below may be constructed by ligating sequences encoding additional amino acid residues to the inventive sequences without affecting biological activity.

Mutations in nucleotide sequences constructed for expression of a soluble CD39 must, of course, preserve the reading frame phase of the coding sequences and preferably will not create complementary regions that could hybridize to produce secondary mRNA structures such as loops or hairpins which would adversely affect translation of the receptor mRNA. Although a mutation site may be predetermined, it is not necessary that the nature of the mutation per se be predetermined. For example, in order to select for optimum characteristics of mutants at a given site, random mutagenesis may be conducted at the target codon and the expressed mutated polypeptides screened for the desired activity.

Not all mutations in the nucleotide sequence which encodes a CD39 polypeptide will be expressed in the final product, for example, nucleotide substitutions may be made to enhance expression, primarily to avoid secondary structure loops in the transcribed mRNA (see EPA 75,444A, incorporated herein by reference), or to provide codons that are more readily translated by the selected host, e.g., the well-known *E. coli* preference codons for *E. coli* expression.

In the genome, CD39 polypeptides are encoded by multi-exon genes. The present invention further includes alternative mRNA constructs which can be attributed to different mRNA splicing events following transcription and which hybridize with the cDNAs disclosed herein under conditions of moderate stringency. CD39 polypeptides according to the invention include allelic variations of the sequence shown in SEQ ID NO:1, and sequences encoding CD39 polypeptides that comprise additional amino acids to those of SEQ ID NO:1.

The isolated nucleic acid sequences of this invention are sufficiently free of association with nucleic acid sequences encoding other proteinaceous material, and from other materials found in living cells, such as proteins, lipids or carbohydrates, to allow the skilled artisan to prepare vectors for the expression of soluble CD39 polypeptides.

E. Recombinant Expression Systems

The present invention also provides recombinant cloning and expression vectors containing CD39 DNA, as well as host cells containing the recombinant vectors. Expression vectors comprising CD39 DNA may be used to prepare soluble CD39 polypeptides encoded by the DNA. The expression vectors carrying the recombinant CD39 DNA sequence are transferred, for example by transfection or transformation, into a substantially homogeneous culture of a suitable host microorganism or mammalian cell line. Transformed host cells are cells which have been transformed or transfected with nucleotide sequences encoding CD39 polypeptides and express CD39 polypeptides. Expressed CD39 polypeptides will be located within the host cell and/or secreted into culture supernatant fluid, depending upon the nature of the host cell and the gene construct inserted into the host cell. The skilled artisan will recognize that the procedure for purifying the expressed CD39 will vary according to such factors as the type of host cells employed.

Any suitable expression system may be employed. Recombinant expression vectors for expression of soluble CD39 by recombinant DNA techniques include a CD39 DNA sequence comprising a synthetic or cDNA-derived DNA fragment encoding a CD39 polypeptide, operably linked to a suitable transcriptional or translational regulatory nucleotide sequence, such as one derived from a mammalian, microbial, viral, or insect gene.

Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the CD39 DNA sequence. Thus, a promoter nucleotide sequence is operably linked to a CD39 DNA sequence if the promoter nucleotide sequence controls the transcription of the CD39 DNA sequence. An origin of replication that confers the ability to replicate in the desired host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the CD39 sequence so that the CD39 is initially translated as a fusion polypeptide comprising the signal peptide. A signal peptide that is functional in the intended host cells promotes extracellular secretion of the CD39 polypeptide. The signal peptide is cleaved from the CD39 polypeptide upon secretion of soluble CD39 from the cell.

Regarding signal peptides that may be employed in producing soluble CD39, the native signal peptide may be replaced by a heterologous signal peptide or leader sequence, if desired. The choice of signal peptide or leader may depend on factors such as the type of host cells in which the recombinant polypeptide is to be produced. To illustrate, examples of heterologous signal peptides that are functional in mammalian host cells include the signal sequence for interleukin-7 (IL-7) described in U.S. Pat. No. 4,965,195, the signal sequence for interleukin-2 receptor described in Cosman et al., *Nature* 312:768, 1984; the interleukin-4 receptor signal peptide described in EP 367,566; the type I interleukin-1 receptor signal peptide described in U.S. Pat. No. 4,968,607; and the type II interleukin-1 receptor signal peptide described in EP 460,846. For the expression of soluble CD39, the inventors have made the surprising and unexpected discovery that the use of a leader containing sequences derived from a human IL-2 polypeptide (SEQ ID NO:9) results in high levels of ATPase activity in the supernatants of transfected cells. Among the particularly preferred embodiments of the invention, therefore, are nucleic acids encoding soluble CD39 polypeptides having an amino acid sequence SEQ ID NO:8.

Suitable host cells for expression of CD39 polypeptides include prokaryotes, yeast or higher eukaryotic cells. Mammalian or insect cells are generally preferred for use as host cells. Appropriate cloning and expression vectors for use with bacterial, fungal, yeast, and mammalian cellular hosts are described, for example, in Pouwels et al. *Cloning Vectors: A Laboratory Manual*, Elsevier, New York, 1985. Cell-free translation systems could also be employed to produce soluble CD39 polypeptides using RNAs derived from DNA constructs disclosed herein.

Prokaryotes include gram negative or gram positive organisms, for example, *E. coli* or *Bacilli*. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, polypeptides may include an N-terminal methionine residue to facilitate expression of the recombinant polypeptide in the prokaryotic host cell. The N-terminal Met may be cleaved from the expressed recombinant polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a CD39 DNA sequence are inserted into the pBR322 vector. Other commercially available vectors include, for example, pKK223-3 (Pharmacia Fine Chemicals, Uppsala, Sweden) and pGEM 1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage λ $P_L$ promoter and a cI857ts thermolabile repressor sequence. Plasmid vectors available from the American Type Culture Collection which incorporate derivatives of the λ $P_L$ promoter include plasmid pHUB2 (resident in *E. coli* strain JMB9, ATCC 37092) and pPLc28 (resident in *E. coli* RR1, ATCC 53082).

Soluble CD39 may also be expressed in yeast host cells, preferably from the *Saccharomyces* genus (e.g., *S. cerevisiae*). Other genera of yeast, such as *Pichia* or *Kluyveromyces*, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase. Other suitable vectors and promoters for use in yeast expression are further described in Hitzeman, EPA-73,657. Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of recombinant polypeptides. The α-factor leader sequence is often inserted between the promoter sequence and the structural gene sequence. See, e.g., Kurjan et al., *Cell* 30:933, 1982 and Bitter et al., *Proc. Natl. Acad. Sci. USA* 81:5330, 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 μg/ml adenine and 20 μg/ml uracil.

Yeast host cells transformed by vectors containing an ADH2 promoter sequence may be grown for inducing expression in a "rich" medium. An example of a rich medium is one consisting of 1% yeast extract, 2% peptone, and 1% glucose supplemented with 80 μg/ml adenine and 80 μg/ml uracil. Derepression of the ADH2 promoter occurs when glucose is exhausted from the medium.

Mammalian or insect host cell culture systems also may be employed to express recombinant CD39 polypeptides. Bacculovirus systems for production of heterologous polypeptides in insect cells are reviewed by Luckow and Summers, *Bio/Technology* 6:47, 1988. Established cell lines of mammalian origin may also be used. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by McMahan et al. (*EMBO J.* 10: 2821, 1991). For the production of therapeutic polypeptides it is particularly advantageous to use a mammalian host cell line which has been adapted to grow in media that does not contain animal proteins. The use of such a cell line for the expression of soluble CD39 is described in Example 13.

Established methods for introducing DNA into mammalian cells have been described (Kaufman, R. J., *Large Scale Mammalian Cell Culture*, 1990, pp. 15-69). Additional protocols using commercially available reagents, such as Lipofectamine (Gibco/BRL) or Lipofectamine-Plus, can be used to transfect cells (Felgner et al., *Proc. Natl. Acad. Sci. USA* 84:7413-7417, 1987). In addition, electroporation can be used to transfect mammalian cells using conventional procedures, such as those in Sambrook et al. *Molecular Cloning: A Laboratory Manual*, 2 ed. Vol. 1-3, Cold Spring Harbor Laboratory Press, 1989). Selection of stable transformants can be performed using methods known in the art, such as, for example, resistance to cytotoxic drugs. Kaufman et al., *Meth. in Enzymology* 185:487-511, 1990, describes several selection schemes, such as dihydrofolate reductase (DHFR) resistance. A suitable host strain for DHFR selection can be CHO strain DX-B11, which is deficient in DHFR (Urlaub and Chasin, *Proc. Natl. Acad. Sci. USA* 77:4216-4220, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., *Nature* 273:113, 1978; Kaufman, *Meth. in Enzymology*, 1990). Smaller or larger SV40 fragments can also be used, provided the approximately 250 bp sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., *Animal Cell Technology*, 1997, pp. 529-534) and the tripartite leader (TPL) and VA gene RNAs from Adenovirus 2 (Gingeras et al., *J. Biol. Chem.* 257:13475-13491, 1982). The internal ribosome entry site (IRES) sequences of viral origin allows dicistronic mRNAs to be translated efficiently (Oh and Sarnow, *Current Opinion in Genetics and Development* 3:295-300, 1993; Ramesh et al., *Nucleic Acids Research* 24:2697-2700, 1996). Expression of a heterologous cDNA as part of a dicistronic mRNA followed by the gene for a selectable marker (e.g. DHFR) has been shown to improve transfectability of the host and expression of the heterologous cDNA (Kaufman, *Meth. in Enzymology*, 1990). Exemplary expression vectors that employ dicistronic mRNAs are pTR-DC/GFP described by Mosser et al., *Biotechniques* 22:150-161, 1997, and p2A5I described by Morris et al., *Animal Cell Technology*, 1997, pp. 529-534.

A useful high expression vector, pCAVNOT, has been described by Mosley et al., *Cell* 59:335-348, 1989. Other expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984, has been deposited as ATCC 39890. Additional useful mammalian expression vectors are described in EP-A-0367566, and in U.S. patent application Ser. No. 07/701,415, filed May 16, 1991, incorporated by reference herein. The vectors can be derived from retroviruses. In place of the native signal sequence, a heterologous signal sequence can be added, such as the signal sequence for IL-7 described in U.S. Pat. No. 4,965,195; the signal sequence for IL-2 receptor described in Cosman et al., *Nature* 312:768, 1984; the IL-4 signal peptide described in EP 367,566; the type I IL-1 receptor signal peptide described in U.S. Pat. No. 4,968,607; and the type II IL-1 receptor signal peptide described in EP 460,846.

Another useful expression vector, pFLAG, can be used. FLAG® technology is centered on the fusion of a low molecular weight (1 kD), hydrophilic, FLAG® marker peptide to the N-Terminus of a recombinant polypeptide expressed by the pFLAG-1™ Expression Vector (obtained from IBI Kodak).

F. Purification of Soluble CD39 Polypeptides

Soluble CD39 polypeptides may be prepared by culturing transformed host cells under culture conditions necessary to express CD39 polypeptides. The resulting expressed polypeptides may then be purified from culture media or cell extracts. Supernatant fluid from the cultured, transformed host cells may be concentrated using a commercially available protein concentration filter, for example, an Amicon or Millipore Pellicon ultrafiltration unit. Following the concentration step, the concentrate may be applied to a cation exchange matrix. Suitable cation exchangers include various insoluble matrices comprising sulfonic or carboxymethyl groups; sulfonic groups are preferred. The matrices can be acrylamide, agarose, dextran, cellulose or other types commonly employed in protein purification. Subsequently, an anion exchange resin is employed, for example, a matrix or substrate having pendant diethylaminoethyl (DEAE) or quaternary amino groups; quaternary amino groups are preferred. The matrices can be acrylamide, agarose, dextran, cellulose or other types commonly employed in protein purification. Additionally, a gel filtration medium may be employed to further purify CD39 polypeptides according to approximate molecular weight. Alternatively, certain of these steps may not be performed, or may be performed in the reverse order.

One or more reverse-phase high performance liquid chromatography (RP-HPLC) steps employing hydrophobic RP-HPLC media, (e.g., silica gel having pendant methyl or other aliphatic groups) may be employed to further purify CD39. A substantially purified and homogeneous polypeptide having CD39 biological activity may be eluted from a polyacrylamide gel subsequent to electrophoretic separation. Some or all of the foregoing purification steps, in various combinations, can also be employed to provide a substantially purified and homogeneous recombinant polypeptide containing less than about 1% by mass of protein contaminants residual of production processes, or alternatively, which is greater than about 95% pure by gel electrophoresis.

Affinity chromatography may be utilized to purify soluble CD39. Affinity purification of soluble CD39 from conditioned media is described in Example 12C. Moreover, small amounts of purified CD39 may be obtained by immunoprecipitating CD39 with a monoclonal antibody, electrophoresing the immunoprecipitate on a polyacrylamide gel, excising the portion of the gel containing the CD39, and eluting the CD39 from the excised portion of the gel.

Recombinant polypeptides produced in bacterial culture are generally isolated by disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells may be employed to express CD39 as a secreted polypeptide. This simplifies purification. Secreted recombinant polypeptide from a yeast host cell fermentation can be purified by methods analogous to those disclosed by Urdal et al. (*J. Chromatog.* 296:171, 1984). Urdal et al. describe two sequential, reversed-phase HPLC steps for purification of recombinant human IL-2 on a preparative HPLC column.

The desired degree of purity of soluble CD39 polypeptides depends on the intended use of the polypeptide. A relatively high degree of purity is desired when the polypeptide is to be administered in vivo, for example. Advantageously, soluble CD39 polypeptides are purified such that no protein bands corresponding to other (non-CD39) polypeptides are detectable upon analysis by SDS-polyacrylamide gel electrophoresis (SDS-PAGE). Following electrophoresis, the protein band may be visualized by silver staining, Coomassie blue staining, or (if the protein is radiolabeled) by autoradiography. It will be recognized by one skilled in the pertinent field that multiple bands corresponding to CD39 polypeptide may be visualized by SDS-PAGE, due to differential glycosylation, differential post-translational processing, and the like.

G. Therapeutic Compositions of CD39 Polypeptides

The present invention provides compositions comprising an effective amount of a soluble CD39 polypeptide in a pharmaceutically acceptable carrier. As used herein, the terms "therapy," "therapeutic," "treat," and "treatment" generally include prophylaxis, i.e., prevention, of a disease or condition in addition to therapy or treatment for an extant disease or condition. Therapeutic compositions of soluble CD39 polypeptides may therefore need to be administered before, during, or after the presentation of symptoms. For therapeutic use, a soluble CD39 polypeptide is administered to a patient for treatment in a manner appropriate to the indication. Thus, for example, soluble CD39 pharmaceutical compositions which are administered to achieve a desired therapeutic effect can be given by bolus injection, continuous infusion, sustained release from implants or the like, or other suitable technique. Ideally, development of a stable form of CD39 or closely related biologically active variant would allow its use in oral form, a preferable route of administration. Since CD39 is aspirin-insensitive, these two therapeutic agents (CD39 compositions and aspirin) can be used in combination, for maximal benefit.

Typically, a soluble CD39 therapeutic agent will be administered in the form of a pharmaceutical composition comprising purified soluble CD39 in conjunction with physiologically acceptable carriers, including excipients or diluents. Such carriers will be nontoxic to patients at the dosages and concentrations employed. As described in the examples that follow, the administration of CD39 in murine and porcine models of thrombosis does not cause any observable toxic effects. Moreover, a second dose of CD39 does not evoke any signs of immunogenicity. Ordinarily, the preparation of such compositions entails combining a soluble CD39 composition with buffers, antioxidants such as ascorbic acid, low molecular weight (less than about 10 residues) polypeptides, polypeptides, amino acids, carbohydrates including glucose, sucrose or dextrans, chelating agents such as EDTA, glutathione and other stabilizers and excipients. Neutral buffered saline or saline mixed with conspecific serum albumin are exemplary appropriate diluents.

One type of sustained release technology which may be used in administering soluble CD39 compositions is that utilizing hydrogel materials, for example, photopolymerizable hydrogels (Sawhney et al., *Macromolecules* 26:581; 1993). Similar hydrogels have been used to prevent post-surgical adhesion formation (Hill-West et al., *Obstet. Gynecol.* 83:59, 1994) and to prevent thrombosis and vessel narrowing following vascular injury (Hill-West et al., *Proc. Natl. Acad. Sci. USA* 91:5967, 1994). Polypeptides can be incorporated into such hydrogels to provide sustained, localized release of active agents (West and Hubbel, *Reactive Polymers* 25:139, 1995; Hill-West et al., *J. Surg. Res.* 58:759; 1995). The sustained, localized release of CD39 when incorporated into hydrogels would be amplified by the long half life of CD39, which is demonstrated in the Examples below.

Accordingly, the soluble CD39 compositions described herein can also be incorporated into hydrogels, for application to tissues for which localized inhibition of hemostasis is desirable. For example, a hydrogel incorporating a CD39 polypeptide can be applied to tissue after surgery, to prevent or reduce post-surgical adhesion formation, or can be applied using a catheter-based delivery system following angioplasty to prevent or reduce restenosis. Those of skill in the art will be able to formulate an appropriate hydrogel by applying standard pharmacokinetic studies, for example as discussed in West and Hubbell, supra.

Effective amounts may vary, depending on the age, type and severity of the condition to be treated, body weight, desired duration of treatment, method of administration, and other parameters. Effective dosages are determined by a physician or other qualified medical professional. Typical dosages are 0.01-100 mg/kg body weight, preferably 0.1-10 mg/kg body weight. In some embodiments a single administration is sufficient; in some embodiments the soluble CD39 polypeptide is administered on a daily basis for up to a week or as much as a month or more.

The biological effectiveness of soluble CD39 polypeptides is easily evaluable: at given time intervals after administration, a prolongation of the bleeding time in the setting of unchanged platelet count should be measurable if released platelet ADP has been metabolized by the CD39 composition administered. This would indicate that a therapeutic effect has likely been obtained, as said measurement correlates with clinical improvement. A therapeutic effect can also be validated by testing platelet reactivity to ADP and other platelet agonists ex vivo. Actual measurements of enzyme (apyrase) activity can also be made following administration of soluble CD39. These and other methods of measuring biological effectiveness are illustrated in the Examples below.

H. Abbreviations Used in the Specification
  ACR, apyrase conserved regions;
  AG, Affigel beads;
  ASA, acetylsalicylic acid;
  ATPDase, ATP diphosphohydolase;
  CHO, Chinese hamster ovary;
  CM, conditioned medium;
  DHFR, dihydrofolate reductase;
  FSBA, fluorosulfonylbenzoyl-adenosine;
  HUVEC, human umbilical vein endothelial cells;
  PRP, platelet-rich plasma;
  PTCA, percutaneous transluminal coronary angioplasty;
  solCD39, recombinant soluble human CD39;
  TBS, Tris-buffered saline

EXAMPLES

The following examples are intended to illustrate particular embodiments and not to limit the scope of the invention.

Example 1

Assay For CD39 Expression

This example describes the use of a monoclonal antibody in a FACS assay to analyze expression of CD39. The B73 mAb, a monoclonal anti-CD39, is a murine IgG1 that was derived from BALB/c mice immunized with the RPMI 1788 cell line (Rector et al., *Immunology* 55:481, 1985) and characterized as CD39-specific by flow cytometric analysis and immunoprecipitation/SDS-PAGE. Monoclonal anti-CD39 is purified from ascites fluid by affinity chromatography using a protein A column, eluted with 0.05 M sodium citrate, pH 3.0, neutralized and stored a 4° C. at a concentration of about 1 mg/ml.

Cells to be analyzed (e.g., MP-1 cells, U937 cells, U937 cells stimulated with 5 ng/ml phorbol myristate acetate (PMA), or Daudi cells) are suspended to a concentration of $10^6$ cell in 50 µl of phosphate buffered saline (PBS) containing 100 µg/ml human IgG1, and incubated for 30 minutes. The cells are then pelleted by centrifugation, resuspended in PBS/azide containing a first antibody (anti-CD39 or control antibody) and incubated (i.e., for 30 minutes at 4° C.) The cells are then washed two times in PBS/azide, resuspended, and incubated with a labeled second antibody, for example, goat anti-murine immunoglobulin conjugated to phycoerythrin, then washed again. The cells are analyzed by flow cytometry, and levels of CD39 determined.

Example 2

Immunoselection of Cells Expressing CD39

This example describes a panning (immunoselection) technique for cells expressing CD39. For the preparation of pan plates, purified anti-CD39 or control antibody is diluted in phosphate buffered saline containing 0.1% heat-inactivated fetal calf serum (PBS/FCS). A titration of anti-CD39 can be performed to determine the most effective concentration of anti-CD39. Pan plates are prepared by adding three ml of antibody solution or PBS/FCS alone to each plate. The plates are incubated for approximately one hour at room temperature, washed five times with PBS/FCS, and three ml of PBS/FCS containing 0.02% sodium azide are added to each plate.

The cells to be analyzed (e.g., MP-1, U937, or Daudi cells) are suspended in PBS/500 µM EDTA/0.02% sodium azide (PEA) containing 5% goat serum, 5% rabbit serum and 100 µg/ml human $IgG_1$, to a concentration of $2 \times 10^6$ cells/ml; 500 µl of each cell suspension is added to the prepared pan plates. The pan plates are incubated with the cell suspension for approximately two hours at room temperature, then the plates are washed gently three times with PEA containing 10% FCS (PEA/FCS), and three times with PEA. The plates are examined with a microscope, and the relative number of cells bound to each plate is determined.

Example 3 cDNA Library Construction

This example describes preparation of a cDNA library from a human B cell line referred to as MP-1, for expression cloning of human CD39.

The library construction techniques were substantially similar to that described by Ausubel et al., eds., *Current Protocols In Molecular Biology*, Vol. 1, 1987. Briefly, total RNA was extracted from 8M guanidine HCl-lysed MP-1 cell cultures using differential ethanol precipitation and poly $(A)^+$ mRNA was isolated and enriched by oligo dT cellulose chromatography. Double-stranded cDNA was made from an RNA template substantially as described by Gubler et al., *Gene* 25:263, 1983. Poly$(A)^+$ mRNA fragments were converted to RNA-cDNA hybrids using reverse transcriptase primed with random hexanucleotides. The RNA-cDNA hybrids were then converted into double-stranded cDNA fragments using RNAase H in combination with DNA polymerase I. The resulting double-stranded cDNA was blunt-ended with T4 DNA polymerase.

Unkinased (i.e. unphosphorylated) BglII adaptors were ligated to 5' ends of the above blunt-ended cDNA duplexes, using the adaptor cloning method described in Haymerle et al., *Nucleic Acids Res.* 14:8615, 1986. Under the described conditions, only the 24-mer oligonucleotide (top strand) will covalently bond to the cDNA during the ligation reaction. The non-covalently bound adaptors (including the complementary 20-mer oligonucleotide described above and any unligated adaptors) were removed by gel filtration chromatography at 65° C., leaving 24 nucleotide non-self-complementary overhangs on the cDNA termini.

The adaptored cDNA was inserted into adaptored pDC303, a mammalian expression vector that also replicates in *E. coli*. pDC303 was assembled from pDC201 (a derivative of pMLSV, previously described by Cosman et al., *Nature* 312: 768, 1984), SV40 and cytomegalovirus DNA and comprises, in sequence with the direction of transcription from the origin of replication, the following components: (1) SV40 sequences from coordinates 5171-270 containing the origin of replication, enhancer sequences and early and late promoters; (2) cytomegalovirus promoter and enhancer regions (nucleotides 671-63 from the sequence published by Boechart et al. (*Cell* 41:521, 1985); (3) adenovirus-2 from coordinates 5779-6079 containing the first exon of the tripartite leader (TPL), segment 7101-7172 and 9634-9693 containing the second exon and part of the third exon of the TPL and a multiple cloning site (MCS) containing sites for XhoI, KpnI, SmaI and BglI; (4) SV40 segments from coordinates 4127-4100 and 2770-2533 containing the polyadenylation and termination signals for early transcription; (5) adenovirus-2 sequences from coordinates 10532-11156 of the virus-associated RNA genes VAI and VAII of pDC201; and (6) pBR322 sequences from coordinates 4363-2486 and 1094-375 containing the ampicillin resistance gene and origin of replication.

The MP-1 cDNA library in pDC303 was introduced into *E. coli* strain DH10B by electroporation. Recombinants were plated to provide approximately 5,000 colonies per plate. These recombinants were pooled to give a bulk stock of approximately 500,000 recombinants for screening. DNA was prepared from transformed bacteria and isolated by cesium chloride centrifugation.

Example 4

Molecular Cloning of Human CD39 cDNA

This example describes the isolation of a DNA molecule encoding CD39 from the expression cloning library described in Example 3.

A. Round I: Transfection and Immunoselection

The isolated plasmid DNA was transfected into a subconfluent layer of COS-7 cells using DEAE-dextran and a chloroquine treatment substantially according to the procedures described in McMahan et al., *EMBO J.* 10:2821; 1991.

COS-7 cells were maintained in transfection and growth medium (Dulbecco's modified Eagles' medium containing 10% (v/v) fetal calf serum, 50 U/ml penicillin, 50 µg/ml streptomycin, 2 mM L-glutamine and 50 µg/ml gentamicin) and were plated to a density of approximately $1.5 \times 10^6$ cells in 10 ml transfection and growth medium in 10 cm dishes. Medium was removed from adherent cells growing in a layer to approximately 70% confluency, and replaced with 10 ml complete medium containing 66.5 µM chloroquine. About 500 µl of a DNA solution (5 µg DNA, 0.5 mg/ml DEAE-dextran in transfection and growth medium containing 66.5 µM chloroquine) was added to the cells and the mixture was incubated at 37° C. in 10% $CO_2$ for about five hours.

Following incubation, media was removed and the cells were shocked by addition of 5 ml transfection and growth medium containing 10% DMSO (dimethylsulfoxide) for 2.5-20 minutes. Shocking was followed by replacement of the solution with 10 ml fresh transfection and growth medium. Twelve plates of cells were grown in culture for two to three days to permit transient expression of the inserted DNA sequences. The cells were trypsinized after about 24 hours of growth in order to remove them from the plates. After an additional one to two days, cells expressing CD39 were selected by panning, essentially as described in Example 2. The cells were incubated in the mAb 73 pan plates for two hours at room temperature, after which unbound cells were removed by gently rinsing three times with PEA/FCS, then three times with PEA.

The cells that were not removed by rinsing were expressing CD39; cells expressing CD39 were lysed by the addition of 700 μl lysing buffer containing sodium dodecyl sulfate (SDS) and incubation for 20 minutes at room temperature. Lysates were transferred from each dish to individual microfuge tubes containing 100 μl of 5 M NaCl. The tubes were capped, mixed thoroughly by inverting about 20 times, and stored at 4° C. overnight. After overnight incubation at 4° C., high molecular weight DNA (debris) was removed by centrifugation, and 2 μg of glycogen was added to each supernatant. The supernatants were then extracted twice with phenol/chloroform and once with chloroform/isoamyl alcohol. DNA was ethanol precipitated, washed with 80% ethanol, and vacuum dried. The purified DNA was then electroporated into *E. coli*, which were then plated out on ampicillin plates. A large-scale transformation was carried out in this manner, yielding a total of approximately 48,000 colonies (sub-library 1). DNA was prepared from the colonies using CsCl; frozen stocks of the colonies were prepared at the same time.

B. Round II: Electroporation and Immunoselection

The DNA from sub-library 1 was electroporated into COS cells (10×10 cm plates). Transfected COS cells were incubated, harvested and panned substantially as described for Round I above. DNA was isolated and a sub-library (sub-library 2) of approximately 50,000 independent colonies was prepared substantially as described above.

C. Round III: Electroporation and FACS Selection

The DNA from sub-library 2 was electroporated into COS cells (10×10 cm plates). Transfected COS cells were incubated and harvested substantially as described for Round I above. The harvested cells were analyzed by FACS substantially as described in Example 1 above. A small subpopulation of cells expressing CD39 was observed, and was sorted out from the larger mixture of cells; DNA was isolated from the sorted cells. A sub-library (sub-library 3) of approximately 5,000 independent colonies was prepared. The DNA was pooled into 10 pools of approximately 500 colonies each; isolated DNA and frozen stocks of bacteria were prepared for each pool.

D. Round IV: Transfection and Immunoselection

The DNA from sub-library 3 was transfected into COS cells using DEAE-dextran and chloroquine treatment, and incubated, substantially as described for Round I above, except that the cells were incubated on fibronectin-treated, chambered slides (10 slides, 1 for each pool, and 4 control slides) instead of 10 cm plates. After two days of growth, the cells were harvested as described, and analyzed by FACS substantially as described in Example 1 above, as well as by a slide dipping technique. In the slide dipping technique, the slides were incubated with $^{125}$I-labeled mAb 73 and fixed with glutaraldehyde. The results were determined by autoradiography using light microscopy to detect cell containing silver granules.

Two pools containing approximately 500 individual clones each were identified as potentially positive for production of CD39. The pools were titered and plated to provide plates containing an average of approximately 150 colonies each. A replicate nitrocellulose filter was prepared from each plate; each plate was then scraped to provide smaller pools of plasmid DNA.

E. Round V: Transfection and Immunoselection

COS-7 cells were transfected with the DNA from the smaller pools by DEAE-dextran, according to the same procedure described above. The transfected cells were screened by slide dipping and FACS as described previously. Two of the smaller pools contained clones that were positive for CD39 as indicated by the presence of an expressed gene product that bound mAb 73.

A total of 156 colonies was picked from the replicate filter corresponding to one of the positive smaller pools, and inoculated into culture medium for overnight growth. After overnight growth, the cultures were arranged in a matrix format of 12 rows and 13 columns. Subpools of culture medium were prepared by pooling medium from each row and each column for a total of 24 subpools. The subpools were used to prepare DNA for a final round of transfection and screening. An intersection of a positive row and a positive column indicated a potential positive colony One potential positive colony (i.e. clone) was identified.

A streak plate was prepared from the positive clone (clone 1), and minipreps of DNA were made from nine individual colonies from the streak plate. The DNA was digested with Bgl II and analyzed by SDS-PAGE. Nine of nine individual colonies from clone I contained identical inserts of 1.8-2.0 Kb. A single isolate that contained the 1.8-2.0 Kb insert was picked and inoculated into 10 ml culture medium for overnight growth. DNA was prepared and sequenced by dideoxynucleotide sequencing. The nucleotide and deduced amino acid sequence of clone 1 is given in SEQ ID NO:1. A cloning vector containing human CD39 sequence, designated pCD39 was deposited with the American Type Culture Collection, Rockville, Md. (ATCC) on Sep. 29, 1992, under the Budapest Treaty, and assigned accession number 69077. A murine homolog of CD39 was isolated by cross-species hybridization; the amino acid sequence of the murine homolog is described in Maliszewski et al., J. Immunol. 153:3574, 1994.

Example 5

Preparation of CD39 mAbs

This example describes the preparation of additional monoclonal antibodies against CD39, including antibodies against the region that contains apyrase activity. Preparations of purified CD39 fragments exhibiting ADPase activity, for example, or transfected cells expressing such CD39 polypeptides, are employed as immunogens to generate monoclonal antibodies against CD39 using conventional techniques, such as those disclosed in U.S. Pat. No. 4,411, 993. DNA encoding CD39 fragments can also be used as an immunogen, for example, as reviewed by Pardoll and Beckerleg in *Immunity* 3:165, 1995. Such antibodies are useful for interfering with CD39-induced platelet aggregation, as components of diagnostic or research assays for CD39 or CD39 activity, and in affinity purification of CD39.

To immunize rodents, CD39 immunogen is emulsified in an adjuvant (such as complete or incomplete Freund's adjuvant, alum, or another adjuvant, such as Ribi adjuvant R700 (Ribi, Hamilton, Mont.), and injected in amounts ranging from 10-100 μg subcutaneously into a selected rodent, for example, BALB/c mice or Lewis rats. DNA may be given intradermally (Raz et al., *Proc. Natl. Acad. Sci. USA* 91:9519, 1994) or intramuscularly (Wang et al., *Proc. Natl. Acad. Sci. USA* 90:4156, 1993); saline has been found to be a suitable diluent for DNA-based antigens. Ten days to three weeks days later, the immunized animals are boosted with additional immunogen and periodically boosted thereafter on a weekly, biweekly or every third week immunization schedule.

Serum samples are periodically taken by retro-orbital bleeding or tail-tip excision for testing by dot-blot assay (antibody sandwich), ELISA (enzyme-linked immunosorbent assay), immunoprecipitation, or other suitable assays, including FACS analysis. Following detection of an appropriate antibody titer, positive animals are given an intravenous injection of antigen in saline. Three to four days later, the animals are sacrificed, splenocytes harvested, and fused to a murine myeloma cell line (e.g., NS1 or preferably Ag 8.653 [ATCC CRL 1580]). Hybridoma cell lines generated by this procedure are plated in multiple microtiter plates in a selective medium (for example, one containing hypoxanthine, aminopterin, and thymidine, or HAT) to inhibit proliferation of non-fused cells, myeloma-myeloma hybrids, and splenocyte-splenocyte hybrids.

Hybridoma clones thus generated can be screened by ELISA for reactivity with CD39, for example, by adaptations of the techniques disclosed by Engvall et al., *Immunochem.* 8:871, 1971 and in U.S. Pat. No. 4,703,004. A preferred screening technique is the antibody capture technique described by Beckman et al., *J. Immunol.* 144:4212, 1990. Positive clones are then injected into the peritoneal cavities of syngeneic rodents to produce ascites containing high concentrations (>1 mg/ml) of anti-CD39 monoclonal antibody. The resulting monoclonal antibody can be purified by ammonium sulfate precipitation followed by gel exclusion chromatography. Alternatively, affinity chromatography based upon binding of antibody to protein A or protein G can also be used, as can affinity chromatography based upon binding to CD39 polypeptide. An alternative strategy is to employ full-length CD39 immunogen, selecting for antibodies that bind CD39, and winnowing out those that bind to previously defined epitopes, for example by screening with a fragment of CD39 that represents a previously defined epitope.

Monoclonal antibodies are also prepared by immunizing CD39 knockout mice, such as those described in Example 19D, with CD39 immunogen. Since the entire CD39 sequence is seen as "foreign" in the knockout mice, this strategy can lead to the generation of antibodies recognizing epitopes that are shared across species lines, including antibodies that antagonize or agonize CD39 bioactivity.

Example 6

Physiological Activity of CD39

This example demonstrates that CD39 is the endothelial cell ecto-ADPase responsible for inhibition of platelet function. Human umbilical vein endothelial cells (HUVEC) constitutively inhibit platelet responsiveness to prothrombotic stimuli by catabolism of exogenous platelet-derived ADP. The endothelial ecto-ADPase has been identified as CD39 (Marcus et al., *J. Clin. Invest.* 99:1351, 1997). Anti-CD39 antibodies immunoprecipitated ADPase activity from a preparation derived from endothelial membranes, and COS cells transfected with an expression vector comprising CD39 acquired ecto-ADPase activity whereas COS cells transfected with a control vector did not. Ecto-ADPase activity was measured in a manner similar to that described in Marcus et al., *J. Clin. Investigation* 88:1690, 1991, by conversion of $^{14}$C-ADP to AMP by transfectant monolayers as well as membrane preparations, and was greater than or comparable to activity of intact HUVEC monolayers and solubilized membranes HUVEC mRNA was analyzed by RT-PCR using primer pairs derived from the sequence of the human CD39 lymphoid cell activation antigen with emphasis on its N-terminal portion. Lymphoid CD39 cDNA was used for direct comparison of PCR product sizes. The data demonstrated identity between HUVEC and lymphoid CD39 in the 4 fragments spanning the portion analyzed (approximately 1250 of the 1850 bp of lymphoid CD39). Northern blot analyses revealed that the mRNA for CD39 in HUVEC was expressed in the same band pattern as in MP-1 cells, from which CD39 was originally cloned.

Confocal microscopy and fluorescence activated cell sorting, using mAb73, were used to determine if HUVEC cells expressed CD39. The FACS protocol was substantially as described in Example 1. For confocal microscopy, cells (human umbilical vein endothelial or transfected COS-1 cells) grown on coverslip glass were washed with PBS and fixed with 3% paraformaldehyde for 30 minutes at room temperature. Auto fluorescence was quenched by treatment with 50 mM $NH_4Cl$ for 10 minutes. Cells were then incubated in PBS containing 5% NGS (normal goat serum) plus 0.1% triton X-100 to block non-specific binding and to permeabilize cells. Cells were then incubated with anti-CD39 antibody at 5 µg/ml in PBS containing 5% NGS +0.1% triton X-100 for 1 hour at room temperature. Following three washes with PBS containing 5% NGS +0.1% triton X-100 cells were incubated with goat anti-mouse labeled with Texas Red (Molecular Probes) at 5 µg/ml in addition to 10 mM YOYO (Molecular Probes) for nucleic acid counter stain, for 1 hour at room temperature. Cells were washed 3 times with PBS containing 5% NGS +0.1% triton X-100 and mounted in 100 mg/ml DABCO (1,4 diaxabicyclo [2.2.2] octane) (Sigma) in 50% glycerol. Cells were then viewed with Multiprobe 2001 laser scanning confocal microscope (Molecular Dynamics). One image was collected of CD39 staining (Texas Red) and a second image was collected of cell nuclei (YOYO).

Both the confocal microscopy and FACS experiments demonstrated that HUVEC express CD39. The patterns of expression were similar to those seen in cells transfected with full-length human CD39.

The physiological activity of CD39 was illustrated by the ability of CD39-transfected COS cells to inhibit and completely reverse platelet aggregation by 10 µM ADP. CD39-transfected COS cells, as well as MP-1 cells and HUVEC, metabolized this quantity of ADP to AMP within three to four minutes and, when added to platelet rich plasma (substantially as described in Marcus et al., supra), they rapidly reversed platelet aggregation. This activity occurred within the time frame of platelet adhesion to injured subendothelium, a process leading to immediate ADP release, recruitment of additional platelets and formation of a hemostatic plug or thrombus. This time course paralleled platelet inhibition by CD39-expressing cells, and was commensurate with their ADPase activities. The activity of ADPase/CD39 was independent of formation of other known thromboregulators, nitric acid or prostacyclin. These results demonstrate the importance of ADPase/CD39 as a physiological, constitutively expressed endothelial cell thromboregulator.

Example 7

Phosphate Release Assay for ATPase Activity

This example describes an ATPase assay that may be used to track enzyme activity. Samples (approximately 100 µl of either concentrated CM or purified polypeptide) are combined with 20 µl of 10× assay buffer (200 mM HEPES, 1.2 M NaCl, 50 mM KCl, 15 mM $CaCl_2$, 15 mM $MgCl_2$ and 3 mM ATP) and sterile water is added to a final volume of 200 µl. Radiolabeled ATP (0.8 µCi γ [$^{32}$P] ATP; Amersham, Arlington Heights, Ill.) is added and the mixture incubated for 20 minutes at 37° C. Stop mix (0.5 ml of 20% activated charcoal/1 M HCl) is added and the reaction is placed on ice for 10 minutes. After centrifugation (14K rpm for 10 minutes), the supernatant is assayed for free $^{32}$P using a scintillation counter. Data are expressed as raw counts or net counts, or as picomoles of ATP degraded per minute.

Example 8

Binding Assay

This example describes an assay to asses the binding of CD39 polypeptides to CD39 antibodies by biospecific interaction analysis (BIA) using a biosensor, an instrument that combines a biological recognition mechanism with a sensing device or transducer. An exemplary biosensor is BIAcore™, from Pharmacia Biosensor AB (Uppsala, Sweden; see Fägerstam L. G., *Techniques in Protein Chemistry II*, ed. J. J. Villafranca, Acad. Press, NY, 1991). BIAcore™ uses the optical phenomenon surface plasmon resonance (Kretschmann and Raether, *Z. Naturforschung, Teil. A* 23:2135, 1968) to monitor the interaction of two biological molecules. Molecule pairs having affinity constants in the range $10^5$ to $10^{10}$ $M^{-1}$, and association rate constants in the range of $10^3$ to $10^6$ $M^{-1}s^{-1}$, are suitable for characterization with BIAcore™.

The biosensor chips are coated with CD39 antibody (e.g., mAb73). The different constructs of CD39 to be assessed are then added at increasing concentrations; the chip is regenerated between the different constructs, for example, by the addition of sodium hydroxide. The resultant data can analyzed to qualitatively or quantitatively asses production of CD39 polypeptides. Affinity of the CD39 polypeptides for the CD39 antibodies can also be determined. In a similar manner, other monoclonal antibodies or polypeptides that specifically bind CD39 can be immobilized on a biosensor chip to asses the binding of various CD39 polypeptides.

Example 9

Transient Expression of Soluble CD39 Polypeptides

This example describes the preparation of constructs for the transient expression of soluble CD39 polypeptides.

A. Reagents Used

The B73 mAb, a murine IgG1 recognizing human CD39, was kindly provided by Dr. Guy Delespesse (U. Montreal, Quebec, Canada). The M2 mAb recognizing the FLAG® peptide (DYKDDDDK, SEQ ID NO:10), a murine IgG1, was prepared at Immunex Corp. Affigel 10 (Bio-Rad, Hercules, Calif.) and CNBr-activated Sepharose 4B (Pharmacia Biotech, Piscataway, N.J.) immunoaffinity columns were prepared according to manufacturers' instructions. Typically, coupling efficiencies in the range of 3-5 mg mAb per ml of affinity gel slurry were obtained.

B. Construction of a Soluble CD39 (solCD39) Expression Plasmid

To generate a soluble molecule having the properties of CD39 the N-terminal and C-terminal portions of CD39, including the two transmembrane regions (see FIG. 2), were removed. To allow transport of soluble CD39 into the medium, a leader sequence providing for secretion was added at the amino terminus of the polypeptide.

Constructs of soluble human CD39 (solCD39) were made in the mammalian expression vector pDC206 (Kozlosky et al. *Oncogene*. 10:299, 1995), utilizing human IL2 (huIL2), human growth hormone (huGH) and murine IL7 (muIL7) leaders).

The DNA sequences between the putative transmembrane regions of full-length CD39, including nucleotides 178-1494 of SEQ ID NO:1, were amplified using PCR and the C-terminal transmembrane coding region was replaced with a stop codon. The PCR product was fused to a synthetic DNA fragment encoding an 8 amino acid peptide tag (FLAG®) and ligated with a muIL7 leader (muIL7L) into the plasmid pDC206 vector via Spe1 and Bgl2 restriction sites. This construct encoded N-terminally FLAG-tagged solCD39.

Alternate leaders were introduced by ligating the Spe1/Bgl2 FLAG-solCD39 fragment into two different pDC206 plasmids, with leaders derived from: (1) human growth hormone (huGHL), and (2) a human proinsulin/IL2 fusion polypeptide (huIL2L, Cullen, *DNA*. 7:645, 1988). The coding region of the latter construct, which is shown in SEQ ID NOs:25 and 26, includes sequences encoding the huIL2 leader (huIL2L, nucleotides 1-72, amino acids 1-24 in SEQ ID NO:25), the first 12 amino acids of mature human IL2 (nucleotides 73-108, amino acids 25-36 in SEQ ID NO:25), a four amino acid linker (nucleotides 109-120, amino acids 37-40 in SEQ ID NO:25), the FLAG tag (nucleotides 121-144, amino acids 41-48 of SEQ ID NO:25), and sol CD39 (nucleotides 145-1461, amino acids 49-487 of SEQ ID NO:25).

The constructs comprising the muIL7 leader, the human growth hormone leader, and the human proinsulin/IL2 leader were designated pIL7LFlagSolCD39, pGHLFlagSolCD39, and pIL2LFlagSolCD39 respectively.

Each construct was used to transiently transfect subconfluent layers of COS-1 cells using DEAE dextran followed by chloroquine as described by Cosman et al., *Nature* 312:768, 1984. As a negative control, a CD40 ligand construct (pIl2LCD40lig, Spriggs et al., *J. Exp. Med.* 176:1543, 1992) was also transfected into COS-1 cells.

C. Preparation of Conditioned Medium from solCD39 Transfectants

The transfected COS-1 cells were incubated (37° C., 5% $CO_2$) in 0.5% FCS-supplemented DMEM-F12 medium in 10 $cm^2$ Petri dishes or 175 $cm^2$ tissue culture flasks. After 5 days, conditioned medium (CM) from these cultures was collected, and cells and debris were removed by centrifugation. The CM was concentrated 4-10 fold using a pressurized, stirred cell fitted with a YM-10 (10 kD cutoff) membrane (Amicon Corp., Danvers, Mass.).

D. ATPase Activity in Conditioned Medium from solCD39 Transfectants

ATPase activity in the CM from solCD39 transfectants (100 µL of 10-fold concentrated supernatant) was assayed essentially as described in Example 7, except that the 10× assay buffer contained 30 mM cold ATP. The results are shown in TABLE 1.

The transfections were repeated and the CM (10, 20 and 30 μL, unconcentrated) was assayed essentially as described in Example 7. The results are shown in TABLE 2. Because the pIL2LFlagSolCD39 showed higher ATPase activity in COS-1 supernatants than pIL7LFlagSolCD39 and pGHLFlagSolCD39, this construct was selected for further investigation. ATPase levels in CM from COS-1 cells transfected with pIL2LFlagSolCD39 increased with time in culture over at least 4 days post-transfection.

TABLE 1

ATPase Activity in Concentrated CM from solCD39 Transfectants

| Sample | CPM Release × $10^3$ (raw counts) |
|---|---|
| pIL2LFlagSolCD39 | 99.96 |
| pIL7LFlagSolCD39 | 39.47 |
| pGHLFlagSolCD39 | 21.14 |
| pIL2LCD40lig | 10.53 |
| media only | 7.89 |

TABLE 2

ATPase Activity in CM from solCD39 Transfectants

| Sample | Vol (μL) | CPM Release × $10^3$ (net counts) |
|---|---|---|
| pIL2LFlagSolCD39 | 10 | 24.71 |
|  | 20 | 43.92 |
|  | 30 | 56.93 |
| pIL7LFlagSolCD39 | 10 | 5.01 |
|  | 20 | 9.75 |
|  | 30 | 14.23 |
| pGHLFlagSolCD39 | 10 | 5.51 |
|  | 20 | 7.22 |
|  | 30 | 9.95 |

E. Immunoaffinity Depletion of solCD39 from COS-1 CM

To confirm that recombinant solCD39 accounted for the ATPase activity observed in the CM, CM from COS-1 transfectants was incubated with immunoaffinity beads prior to enzyme assay.

CM was collected from COS-1 cells transfected with pIL2LFlagSolCD39, which had been cultured for 5 days in DMEM/F12 supplemented with 5% FCS. A 100 μl aliquot of drained Affigel beads (AG) conjugated with either chicken ovalbumin, antiFLAG mAb, or anti-CD39 mAb was added per ml of CM. CM was subjected to one or two cycles of binding with one of the following: ovalbumin-conjugated AG, M2 mAb-conjugated AG, or B73 mab-conjugated AG. Each cycle involved continuous gentle agitation of the slurry for 14 h at 4° C. followed by centrifugation to recover supernatants for a subsequent binding cycle or for ATPDase activity measurements.

Figure 3:
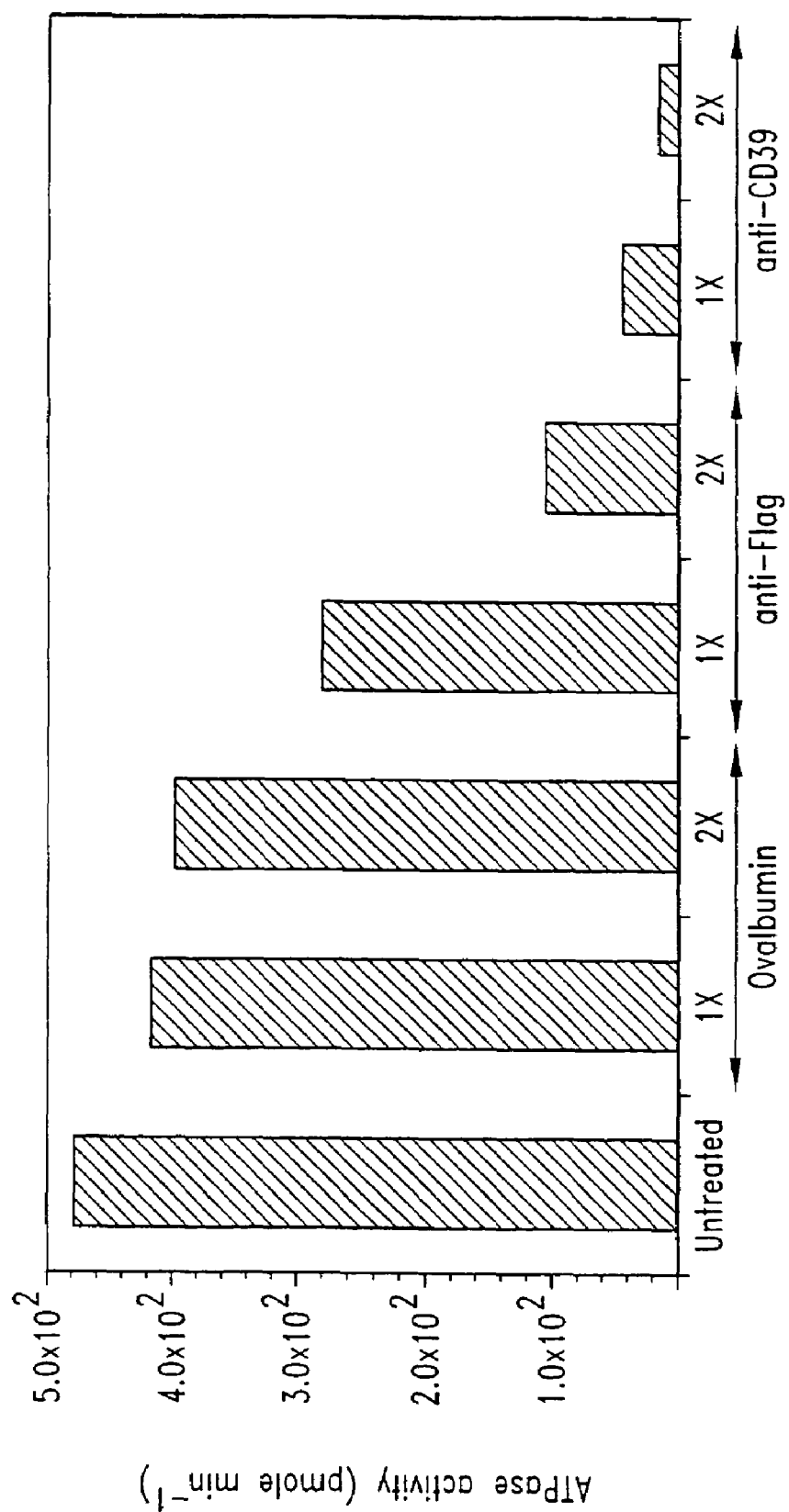
FIG. 3 shows the immunoaffinity depletion of solCD39 from COS-1 conditioned medium (CM) following one (1×) or two (2×) rounds of adsorption. Samples were assayed for ATPase activity as described in Example 7. Data are expressed as pmoles of ATP degraded per minute.

As shown in FIG. 3, immunoprecipitation with anti-CD39 mab-conjugated beads resulted in removal of over 80% of ATPase activity from CM. Over 95% ATPase activity was removed with a second antibody adsorption step. Immunoprecipitation (2 cycles) with anti-FLAG mAb-coated beads also resulted in substantial depletion of enzyme activity. Two rounds of preincubation with a control (ovalbumin-conjugated beads) did not remove significant ATPase activity from the supernatants.

F. Immunoprecipitation of Recombinant solCD39

To characterize recombinant solCD39 polypeptide expression, COS-1 cells were transfected with mammalian expression vectors encoding cell surface CD39 (pHuCD39, Marcus et al., *J. Clin. Invest.* 99:1351, 1997), tagged soluble CD39 (pIL2LFlagSolCD39), or soluble CD40 ligand (pIL-2L-CD40L) and grown in 5% FCS-supplemented DMEM/F12 medium in 10 cm² dishes. Two days after transfection, the medium was replaced with Cys/Met-free medium and cells were incubated for 1 h at 37° C. The culture medium was replaced with fresh Cys/Met-free medium supplemented with 5 μl of [$^{35}$S]-Cys/Met (Amersham, Arlington Heights, Ill.) in order to label newly synthesized polypeptides, and cells were cultured for 5 h at 37° C. CM from the metabolically radiolabeled cells was collected, purified of cells and debris by centrifugation and sterile filtration, and stored at 4° C. until further use.

For radioimmunoprecipitation, 500 μl of $^{35}$S-labeled CM was added to 250 μl of 3% BSA in Tris-buffered saline (TBS), pH 7.7, followed by addition of 50 μl of a 80% slurry of mAb-coated AG beads. In some cases, $^{35}$S-labeled CM were incubated with ovalbumin-coated AG beads to remove nonspecifically binding materials prior to addition of Ab-coated beads. After incubation for 14 h at 4° C., beads were removed by centrifugation and washed three times in cold TBS.

For SDS-PAGE analysis, 35 μl of 4-fold concentrated reducing sample buffer (250 mM Tris/HCl, pH 6.8, 8% (w/v) SDS, 40% (v/v) glycerol, 20% (v/v) 2-mercaptoethanol, 0.05% bromophenol blue dye) was added to each AG pellet, boiled for 5 min, and loaded onto a 8-16% Novex (San Diego, Calif.) polyacrylamide gel. Gels were electrophoresed at 25 mA, prepared for autoradiography by soaking in Enhance (NEN Life Science Products, Boston, Mass.) for 1 h and in H₂O for 20 min, followed by vacuum drying at 80° C. Gels were exposed to Kodak (Rochester, N.Y.) X-omat AR film for 2 h, then developed.

Figure 4:
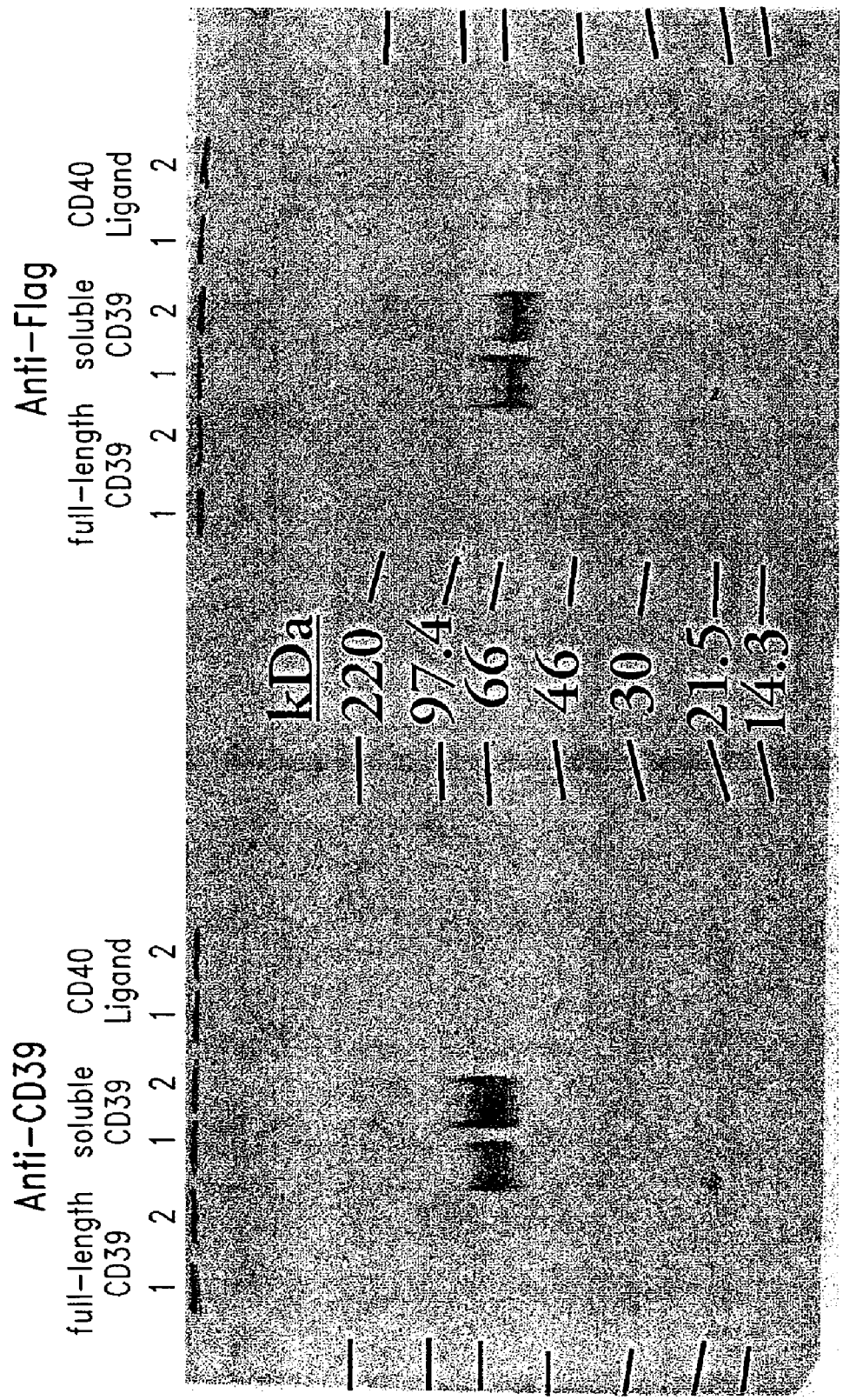
FIG. 4 shows the immunoprecipitation of solCD39 from COS-1 CM. Lane 2 shows the material that specifically bound to the antibody-coated beads. Lane 1 shows material that was pre-incubated with ovalbumin-coated beads to remove non-specifically bound material prior to addition of Ab-coated beads. Migration of molecular weight standards is indicated in kilodaltons (kDa).

As shown in FIG. 4, IL-2L-FlagsolCD39 transfectants secreted a radiolabeled protein of ~66 kD that was recognized by anti-CD39. This protein was not detected in anti-CD39 immunoprecipitated CM from COS-1 cells transfected with a vector encoding full-length CD39 (including N-terminal and C-terminal hydrophobic regions), or with a vector encoding a secreted protein, CD40 ligand. Anti-FLAG mAb immunoprecipitated a similar-sized band from CM of the pIL-2L FlagsolCD39 transfectant, consistent with the presence of the FLAG® peptide in recombinant solCD39. Preclearing radiolabeled culture supernatants with anti-ovalbumin-coated beads failed to remove the 66 kD band, indicating that binding to anti-CD39 and anti-FLAG was specific. Beads coated with an irrelevant, isotype matched control antibody failed to immunoprecipitate the 66 kD band from solCD39 containing CM.

G. Preparation of Additional solCD39 Fusion Constructs

Restriction enzymes were used to prepare a DNA fragment comprising nucleotides 1 through 1488 of SEQ ID NO:1, the coding region of which would be expected to encode a fragment of CD39 lacking the second (most C-terminal) transmembrane domain. Appropriate linker oligonucleotides were prepared (SEQ ID NOs:14 and 15), and used in a three-way ligation of the CD39 DNA, the linker oligonucleotides, and an expression vector comprising regulatory elements allowing expression of a resulting fusion polypeptide in mammalian cells along with DNA encoding a mutated human immunoglobulin Fc (SEQ ID NOs:16 and 17) region that exhibits reduced affinity for Fc receptors (nucleotides 42 through 740 of SEQ ID NO:16). This construct was referred to as CD39Δ2Fc, and when transfected into cells resulted in the expression of a fusion polypeptide comprising amino acids 1 through 474 of SEQ ID NO: 1 and amino acids 1 though 232 of SEQ ID NO:17, which could be detected on the surface of transfected cells using either anti-CD39 or anti-human IgG.

A PCR technique was employed to prepare a fragment of DNA from the CD39Δ2Fc construct that also lacked the first, most amino-proximal transmembrane region, but included CD39 DNA from nucleotides 181 through 1488 (amino acids 39 through 474) of SEQ ID NO:1 and the Fc mutein DNA from CD39Δ2Fc (using the linkers shown in SEQ ID NOs:18 and 19).

The resulting DNA was then ligated into an expression vector that included DNA encoding the murine Interleukin-7 leader sequence (SEQ ID NO:20) ligated immediately proximal to the CD39-encoding sequence. This construct was designated CD39Δ1,Δ2Fc.

DNA encoding the FLAG® peptide (SEQ ID NO:10) and a codon corresponding to nucleotides 178, 179 and 180 of SEQ ID NO:1 was inserted into the CD39Δ1,Δ2Fc construct, in between the leader sequence and the CD39-encoding sequence, to provide a detectable tag for the amino terminus of the fusion polypeptide (using the linkers shown in SEQ ID Nos:21 and 22). The tagged construct was referred to as FlagCD39Δ1,Δ2Fc.

Another construct was prepared that removed the Fc mutein sequences, and added codons corresponding to nucleotides 1489 through 1494 of SEQ ID NO:1 immediately downstream of the CD39 sequences (using the linkers shown in SEQ ID Nos:23 and 24). This construct was designated FlagCD39Δ1,Δ2.

Each of the constructs was transfected into mammalian cells and protein levels were assayed on the surface, in the interior, or in the supernatant fluid of transfected cells using antibodies to FLAG®, CD39, or human IgG.

Example 10

Expression and Activity of pIL2LSolCD39

To facilitate the establishment of a stably producing transfectant in CHO cells, an untagged version of soluble human CD39 (solCD39) was constructed. A 523 bp Spe1/Nde1 fragment containing the FLAG® tag and the first 163 amino acids (aa) of pIL2LFlagSolCD39 was removed, and replaced with a similar fragment from a C-terminally FLAG®-tagged solCD39. Thus the entire solCD39 coding region was reconstituted, sans FLAG®, while retaining the HuIL2 leader and mature IL2 residues. This construct was designated pIL2LSolCD39. The coding region of pIL2LSolCD39, which is shown in SEQ ID NO:7, includes sequences encoding the huIL2 leader (huIL2L, nucleotides 1-72, amino acids 1-24 in SEQ ID NO:7), the first 12 amino acids of mature human IL2 (nucleotides 73-108, amino acids 25-36 in SEQ ID NO:7), a three amino acid linker (nucleotides 109-117, amino acids 37-39 in SEQ ID NO:7), and sol CD39 (nucleotides 118-1434, amino acids 40-478 of SEQ ID NO:7).

To determine whether activity was affected by removal of the N-terminal FLAG® tag, COS-1 cells were transfected with pIL2LFlagSolCD39 and pIL2LSolCD39 and supernatants (sups) were harvested after 5 days. Samples of 10, 20 and 30 μL of 1× sups were assayed for ATPase activity as described in Example 7. As shown in TABLE 3, activity was not affected by removal of the N-terminal FLAG® tag.

TABLE 3

| ATPase Activity in CM from pIL2LFlagSolCD39 and pIL2LSolCD39 Transfectants | | |
|---|---|---|
| Sample | Vol (μL) | CPM × 10³ (net counts) |
| pIL2LFlagSolCD39 | 10 | 23.6 |
|  | 20 | 40.2 |
|  | 30 | 54.4 |
| pIL2LSolCD39 | 10 | 20.1 |
|  | 20 | 36.0 |
|  | 30 | 51.0 |

Example 11

Preparation of Additional solCD39 Fusion Constructs

A. Preparation and Characterization of Trim1 and Trim2 Variants

To characterize the effect of the 12 mature human IL2 (huIL2) residues on the expression of solCD39, the huIL2 residues were removed during the construction of nucleic acid sequences encoding two additional variants of pIL2LSolCD39: pIL2LTrim1 ("Trim1") and pIL2LTrim2 ("Trim2").

The pIL2LTrim1 variant was constructed by purifying a Hind3/Bgl2 restriction fragment from pIL2LSolCD39 which contained the entire solCD39 coding region except for the first four amino acids. This fragment was ligated with a synthetic oligo cassette (containing the huIL2 leader and the first amino acid of mature huIL2) into Sma1/Bgl2 digested pDC206. The huIL2 leader was thus reintroduced and joined to solCD39 with an intervening alanine residue.

The pIL2LTrim2 variant was constructed in a similar fashion using a Spe1/Bgl2 fragment from pIL2LSolCD39 and a synthetic oligo cassette containing the huIL2 leader and the linker-encoded sequences (with the first codon altered to alanine). Thus, the huIL2 leader was restored with an intervening Ala-Ser-Ser linker preceding solCD39.

The N-terminal portions of the pIL2LSolCD39, pIL2LTrim1 and pIL2LTrim2 polypeptides are compared below, with the predicted cleavage points indicated as *:

```
pIL2LSolCD39                            (SEQ ID NO:11)
MALWIDRMQLLSCIALSLALVTNS*APTSSSTKKTQLLs sT QNK. . .

pIL2LTrim1                              (SEQ ID NO:12)
MALWIDRMQLLSCIALSLALVTNS A              T*QNK. . .

pIL2LTrim2                              (SEQ ID NO:13)
MALWIDRMQLLSCIALSLALVTNS                as*sT QNK. . .
```

The polypeptide encoded by the Trim1 construct has the sequence SEQ ID NO:27. Residues 26-464 are a soluble portion of CD39 and the cleavage of the leader sequence is between Ser24 and Ala25.

The expression of Trim1 and Trim2 constructs was analyzed in COS-1 cells cultured in 10 cm plates. After 5 days of incubation, 1× supernatants were examined via ELISA (using anti-CD39) and the phosphate-release assay described in Example 7. As shown in TABLE 4, the specific activities (based on concentrations determined by ELISA) of Trim1 and Trim2 were equivalent to pIL2LFlagSolCD39. Expression levels, however, appeared to be reduced 3-4 fold.

TABLE 4

SolCD39 Expression and Activity in CM
from pIL2LSolCD39 an Trim Transfectants

| Sample | [CD39] µg/mL | Activity (pmol ATP/min/µg) × $10^3$ |
|---|---|---|
| pIL2LSolCD39 | 0.75 | 5.67 |
| pIL2LTrim1 | 0.21 | 8.38 |
| pIL2LTrim2 | 0.21 | 6.67 |

COS-1 cells were also transfected with pIL2LSolCD39, pIL2LTrim1 and pIL2LTrim2 and cultured in T175 flasks (30 mL). 5-day/1× sups were then analyzed via ELISA. As shown in TABLE 5, the ELISA results again indicated lower expression levels for the Trim1 and Trim2 variants.

To further characterize the effect of the human IL2 (huIL2) residues on the expression of solCD39, the pIL2LSolCD39, pIL2LTrim1, and pIL2LTrim2 products were purified using anti-CD39 coated sepharose. The N-terminal amino acid sequence was determined for each of the purified polypeptides. For solCD39 the N-terminus was APTSSSTKKT . . . (residues 25-34 of SEQ ID NO:11). For Trim1 the N-terminus was ATQNKALPEN . . . (residues 25-34 of SEQ ID NO:27). The Trim2 polypeptides had heterogeneous N-termini.

TABLE 5

SolCD39 Expression in CM from pIL2LSolCD39 and Trim Transfectants

| Sample | [CD39] µg/mL |
|---|---|
| pIL2LSolCD39 | 0.796 |
| pIL2LTrim1 | 0.143 |
| pIL2LTrim2 | 0.113 |

B. Preparation and Characterization of Trim3 and Trim4 Variants

Nucleic acids encoding additional solCD39 variants, designated pIL2LTrim3 ("Trim3") and pIL2LTrim4 ("Trim4"), are also constructed using a synthetic oligo cassette strategy. The N-terminal portions of the solCD39, Trim3 and Trim4 polypeptides are compared below. The predicted cleavage points are indicated as *.

```
pIL2LSolCD39                              (SEQ ID NO:11)
MALWIDRMQLLSCIALSLALVTNS*APTSSST KKTQLtssTQNK . . .

pIL2LTrim3                                (SEQ ID NO:28)
MALWIDRMQLLSCIALSLALVTNS*A       ST KKTQLtssTQNK . . .

pIL2LTrim4                                (SEQ ID NO:29)
MALWIDRMQLLSCIALSLALVTNS         ST*KKTQLtssTQNK . . .
```

The polypeptide encoded by the Trim3 construct has the sequence SEQ ID NO:28. Residues 36-474 are a soluble portion of CD39 and the predicted cleavage of the leader sequence is between Ser24 and Ala25. The polypeptide encoded by the Trim4 construct has the sequence SEQ ID NO:29. Residues 35-473 are a soluble portion of CD39 and the predicted cleavage of the leader sequence is between Thr26 and Lys27.

The pIL2LTrim3, and pIL2LTrim4 polypeptides are expressed and purified using anti-CD39 coated sepharose. The N-terminal amino acid sequence and specific activity are determined for each of the polypeptides.

C. Preparation and Characterization of solCD39-L4 Fusion Polypeptides

Figures 23, 24:
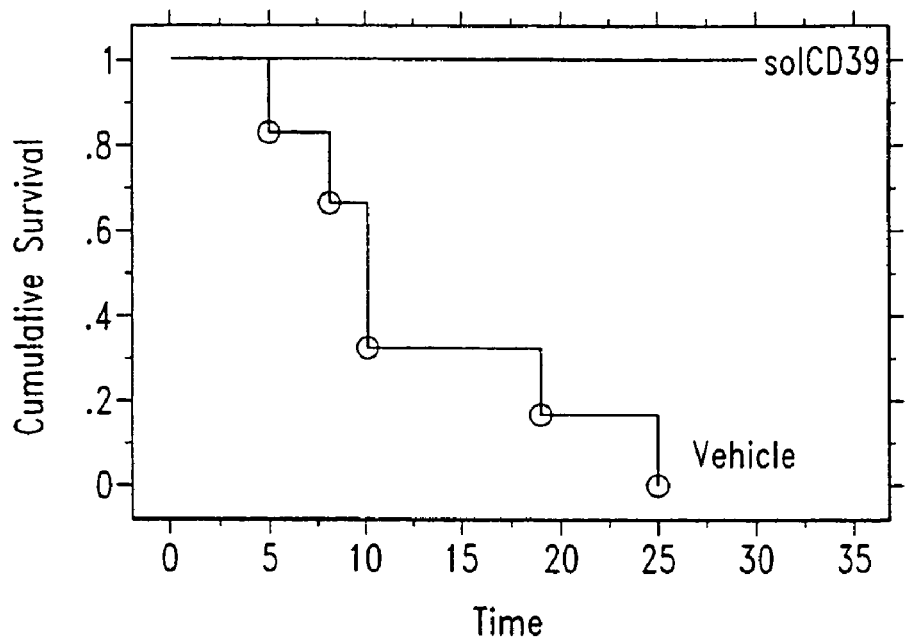
FIG. 23 is a Kaplan-Meier plot showing that solCD39 causes an improvement in survival in a stringent lung ischemia-reperfusion model.
FIG. 24 shows an alignment of the N-terminal amino acid sequences of human CD39 and human CD39-L4.

The CD39 gene family is reported to contain at least four human members: CD39, CD39L2, CD39L3, and CD39L4 (Chadwick and Frischauf, *Genomics* 50:357, 1998). CD39-L4 is reported to be a secreted apyrase (Mulero et al., *J. Biol. Chem.* 274(29):20064, 1999). Additional solCD39 variants are constructed by fusing N-terminal sequences from CD39L2, CD39L3, or CD39L4 to a soluble portion of CD39. The N-terminal amino acid sequences of human CD39 and human CD39-L4 are aligned in FIG. 24.

For one construct, CD39-L4-1, a nucleic acid encoding CD39-L4 amino acid residues 1-37 (Met1 to Ser37 of SEQ ID NO:31) is fused to a nucleic acid encoding CD39 residues 38-476 (Thr38 to Thr476 of SEQ ID NO:2). The polypeptide encoded by the CD39-L4-1 construct has the sequence SEQ ID NO:3. Residues 1-37 are from CD39-L4, residues 38-476 are a soluble portion of CD39, and the predicted site of cleavage of the leader sequence is between Ala20 and Val21.

For another construct, CD39-L4-2, a nucleic acid encoding CD39-L4 amino acid residues 1-48 (Met1 to Leu48 of SEQ ID NO:31) is fused to a nucleic acid encoding CD39 residues 49-476 (Tyr49 to Thr476 of SEQ ID NO:2). Another construct, CD39-L4-3, is identical to CD39-L4-2 except that the Cys residue at position 39 (Cys39) is replaced by another amino acid, preferably Ser. The polypeptides encoded by the CD39-L4-2 and CD39-L4-3 constructs have the sequence SEQ ID NO:4. Residues 1-48 are from CD39-L4, residues 49-476 are a soluble portion of CD39, and the predicted site of cleavage of the leader sequence is between Ala20 and Val21.

Additional constructs are constructed by fusing a portion of the CD39-L4 N-terminal coding region to the CD39 N-terminal coding region. After expression in recombinant cells, the N-terminal sequence, enzymatic activity, and platelet inhibitory activity is determined for each of the polypeptide products.

D. Preparation and Characterization of IgkappaLsolCD39

Nucleic acids encoding an Igkappa leader sequence fused to amino acids from IL-2 and to solCD39 are also constructed. One such construct encodes a polypeptide having an Igkappa leader and four amino acids from IL-2 fused to the N-terminus of the CD39 soluble portion (set forth as residues Thr38 to Thr476 of SEQ ID NO:2). The N-terminus of the encoded polypeptide is therefore: 5'-METDTLLLWVLLLWVPGSTG*APTSTQNKA LPE . . . (amino acids 1-32 of SEQ ID NO:30), where amino acids Met1-Gly20 are the Igkappa leader, Ala21-Ser24 are from IL-2, and Thr25-Glu32 is the beginning of solCD39 sequences. The predicted cleavage site is indicated as *. The polypeptide encoded by the IgkappaLsolCD39 construct has the sequence SEQ ID NO:30. Residues 25-463 are a soluble portion of CD39 and the predicted cleavage of the leader sequence is between Gly20 and Ala21. After expression in recombinant cells, the N-terminal sequence, enzymatic activity, and platelet inhibitory activity is determined for each polypeptide product.

Example 12

Development of a Stably Transfected Cell Line Secreting solCD39

A CHO cell line expressing solCD39 was generated to improve recombinant solCD39 polypeptide production.

A. Preparation of Constructs and Cell Lines for the Stable Expression of Soluble CD39 Polypeptides The solCD39 cDNA insert, containing the recombinant solCD39 sequence and the IL-2 leader but not the FLAG® sequence, was excised from the pIL2LSolCD39 plasmid by XmaI/BglII digestion, then inserted into 2A5Ib, an expression vector containing the DHFR gene and optimized for stable CHO cell lines (Morris et al., In Animal Cell Technology: From Vaccines to Genetic Medicine, M. J. T. Carrondo, B. Griffiths, and J. L. P. Moreira, editors, Kluwer Academic Publishers, Boston. 529-534, 1997).

The solCD39-2A5Ib plasmid was transfected into CHO cells using Lipofectamine (GIBCO BRL; Gaithersburg, Md.) according to manufacturer's recommendations. The CHO cell line used in these studies, DX B-11, had been adapted to serum-free suspension culture conditions. Transfected cells were grown in modified DMEM-F12 medium, supplemented with peptone, glutamine, glucose, transferrin, lipids, and IGF-1 (insulin-like growth factor 1; used solely when cultures were induced for protein expression). After 3 days growth, the cells were transferred to selective medium lacking hypoxanthine and thymidine. Stock cultures were grown at 37° C. in suspension, and passaged every 2-3 days. Induction cultures were grown at 31° C. in suspension, with IGF-1 and sodium butyrate (1-2 mM). Cell density at start of induction cultures was $1.5\text{-}2\times10^6$ cells/ml. The average induction period was 7 days, at which time CM was collected for further analyses.

B. TLC Assays for ADPase and ATPase Activities in CM Containing solCD39

Following growth in selective medium, CM from CHO cell cultures was analyzed for ATPase and ADPase activities. ADPase assays (Marcus et al., *J. Clin. Invest.* 88:1690, 1991) were primarily used in determining enzyme kinetics and pharmacokinetics. Test samples were incubated with 50 µM [$^{14}$C] ADP (NEN Life Science Products) in assay buffer (15 mM Tris, 134 mM NaCl, 5 mM glucose, pH 7.4, containing 10 µM Ap5A ($P^1,P^5$-di[adenosine-5']pentaphosphate, 1 mM ouabain, 10 µM dipyridamole, and 3 mM $CaCl_2$) in a total volume of 50 µl (5 min, 37° C.). Reactions were stopped by placement on ice and addition of 10 µl "stop solution" (160 mM disodium EDTA, pH 7.0, 17 mM ADP, 0.15 M NaCl) to block further metabolism of ADP. Nucleotides, nucleosides, and bases were separated by TLC using isobutanol/1-pentanol/ethylene glycol monoethyl ether/$NH_4OH/H_2O$ (90:60:180:90:120). Radioactivity was quantified by radio TLC scanning (RTLC multiscanner; Packard, Meriden, Conn.). Results were calculated as averages of duplicate to quadruplicate measurements after subtraction of buffer blanks (consistently <1% of total radioactivity). Data were expressed as percentage of ADP metabolized or as pmol ADP metabolized per minute per µl CM. A unit of activity is the quantity of enzyme which will degrade 1 µmol of ADP in 1 min at 37° C. Identical assays were performed using ATP as a substrate in order to examine the kinetics of the ATPase activity of CD39.

As shown in TABLE 6, the stably transfected CHO cells secreted 20-fold higher levels of both enzyme activities compared to CM from transfected COS-1 cells.

TABLE 6

Comparison of ADPase and ATPase Activities in CM Containing solCD39

| Cell Type | ADPase (pmol/min/µl) | ATPase (pmol/min/µl) |
| --- | --- | --- |
| CD39 (CHO) | 1403 | 970 |
| CD39 (COS-1) | 70 | 44 |

C. Affinity Purification of solCD39 from Stably Transfected CHO Cells

Thirty ml of 10-fold concentrated CM from solCD39-secreting CHO cells was added to 3 ml of B73 mAb-coated Sepharose 4B gel slurry and mixed overnight at 4° C. The affinity matrix was pelleted by centrifugation, washed 3 times with PBS, and added to a plastic column. Specifically-bound protein was eluted by the addition of 0.1 M triethylamine, pH 11.5. Fractions (1.2 ml each) were collected in tubes containing 120 µl of neutralizing solution (1 M sodium phosphate, monobasic; pH 4.3) and analyzed for protein content by SDS-PAGE, followed by Coomassie Blue staining. Biological activity was determined using an ATPase assay as described in Example 7, so that peak fractions could be pooled, buffer exchanged into PBS, and concentrated 5-fold. N-linked sugars were removed from purified protein using a kit from Oxford Glycosystems (Rosedale, N.Y.). The recombinant solCD39 was analyzed by SDS-PAGE.

Figure 5A:
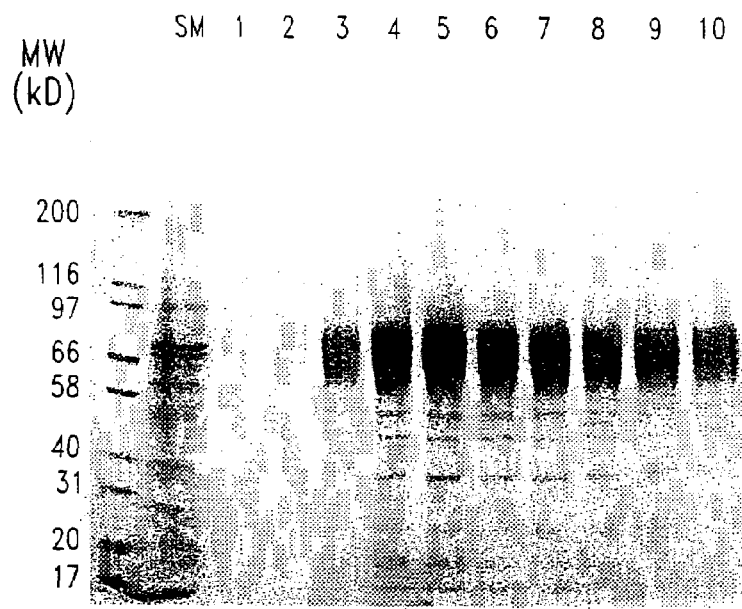
FIG. 5A shows fractions from the immunoaffinity column analyzed by SDS-PAGE.

A prominent band of ~66 kD was present in early eluted fractions, with a peak of Coomassie Blue staining around fraction 5 (FIG. 5A). Over 90% of the protein present was found as this major band. Overloading the polyacrylamide gel did reveal some smaller molecular weight contaminants, however, these appear to be related to the antibodies present on the column and not to the protein loaded on the column.

Figure 5C:
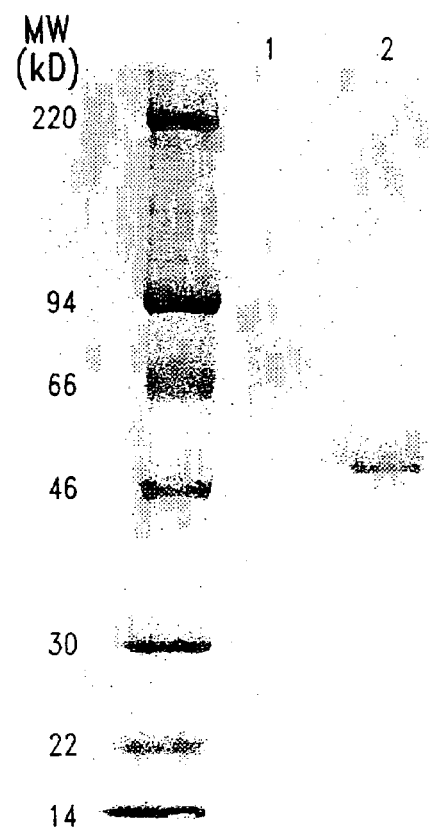
FIG. 5C shows purified solCD39 before (Lane 1) and after (Lane 2) treatment with N-glycanase.
Figure 5B:
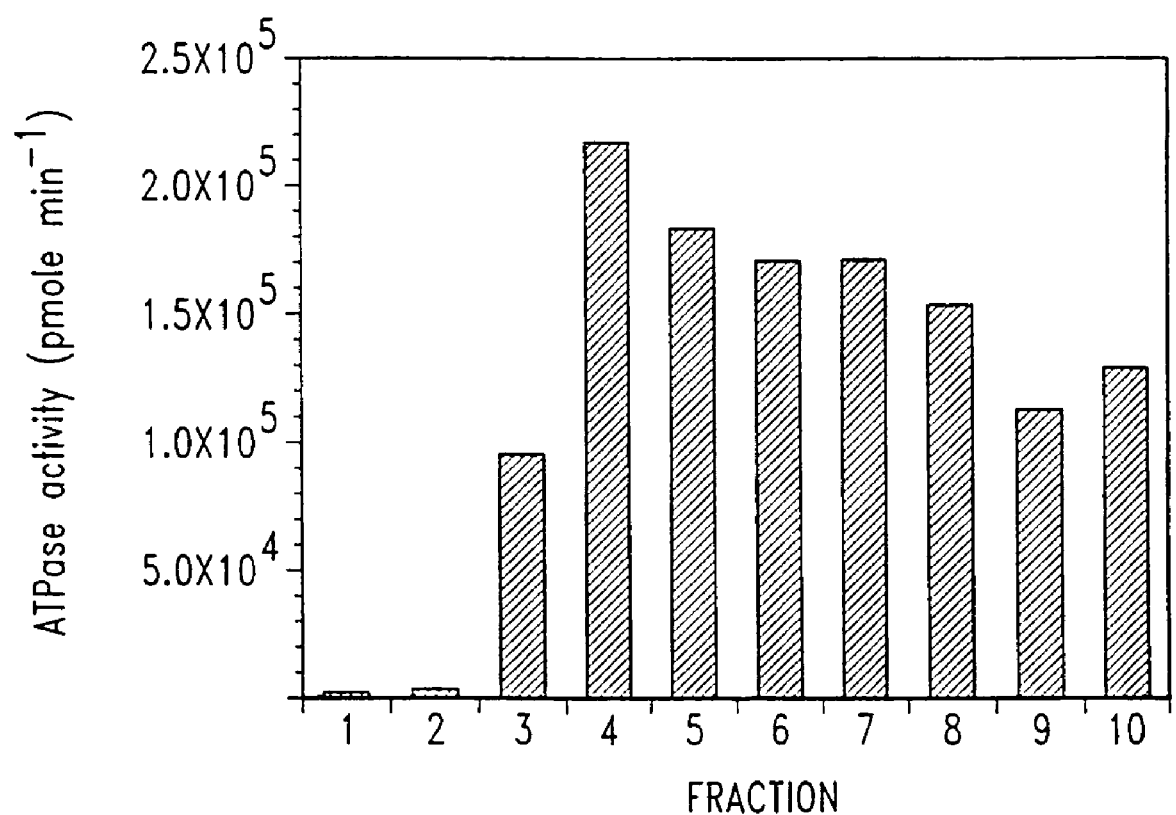
FIG. 5B shows enzyme activity in the fractions.

ATPDase activity of the affinity column fractions correlated with the intensity of protein bands on SDS-PAGE (FIG. 5A, 5B). ATPDase activity was barely detectable in the anti-CD39 column flowthrough, indicating that affinity purification is an effective means of isolating biologically active recombinant solCD39. Treatment of the purified protein with N-glycanase for 18 hours to remove N-linked oligosaccharides caused the broad band of protein at 66 kD to resolve into a much tighter band of protein at approximately 52 kD. the predicted size for solCD39 (FIG. 5C).

The total protein yield from 1 L of CHO-solCD39 CM was ~2 mg. Production of solCD39 was scaled up to 10 liter bioreactors. The resultant conditioned medium contained approximately 50-100 µg/ml of solCD39 according to ELISA analysis. Thus, each 10 L bioreactor run would expected to produce 500-1000 mg of recombinant polypeptide. CHO cell lines expressing additional solCD39 constructs are similarly prepared and characterized.

Example 13

Expression of solCD39 in Veggie-CHO and CS-9 Cells

In this example, soluble CD39 is expressed in CHO cells that have been adapted to grow in suspension in media that does not contain animal proteins (see Rasmussen et al., Cytotechnology 28:31, 1998), or in the presence of IGF-1 in the clonal cell line CS-9.

The dihydrofolate reductase-deficient Chinese hamster ovary cell line, DXB11-CHO is commonly used as a host cell for the production of recombinant polypeptides. DXB11-CHO was adapted to grow in suspension. A serum-free host named Veggie-CHO was then generated by adapting DXB11-CHO cells to growth in serum-free media in the absence of exogenous growth factors such as Transferrin and Insulin-like growth factor (IGF-1). The latter adaptation was achieved by a gradual reduction of serum supplementation in the media and the replacement of serum with low levels of growth factors, IGF-1 and transferrin, in an enriched cell growth media. The suspension adapted serum-free adapted cells were then weaned off these growth factors. The resulting Veggie-CHO cells maintain vigorous growth and high viability as well as a DHFR-deficient phenotype in media that is serum-free and also free of animal-derived proteins. CS-9 cells were also derived from DXB11-CHO cells. The suspension adapted serum-free adapted cells were adapted to grow in the absence of transferrin, then individual clones were isolated. The CS-9 clone was chosen for its stable recombinant protein expression.

Veggie-CHO cells and CS-9 cells are used as a host cell line for the stable, high level expression soluble CD39 polypeptides using methods similar to those described in Example 12.

Example 14

Biochemical Properties of Affinity-Purified solCD39

Purified solCD39 material was subjected to N-terminal amino acid sequencing and mass spectroscopy. Quantitative amino acid analysis of peak fractions (3-9) from the affinity column yielded a ratio of amino acid residues consistent with calculated values for human CD39. The N-terminus of the pIL2LSolCD39 product had the following sequence:

A P T S S S T K K T Q L t s s T Q . . . (residues 25-41 of SEQ ID NO:11).

The first 12 residues represent the mature huIL2 residues; residues 13-15 (tss, lower case) are linker-encoded residues; residues 16,17, etc. (T Q . . . ) are solCD39.

Using the TLC assay system described in Example 12B, the ADPase activity of the membrane-bound HUVEC ecto-ADPase was determined at different pHs in buffers containing 100 mM bis-trispropane (Sigma, St. Louis, Mo.). This was compared to the ADPase activity of purified solCD39 at these pHs. Kinetic constants for CD39 metabolism of ATP and ADP were determined by measuring the initial rates of reaction as analyzed in the TLC system. ADP or ATP at 2.5-150 µM were incubated separately with $2 \times 10^{-9}$ M solCD39.

Figure 6A:
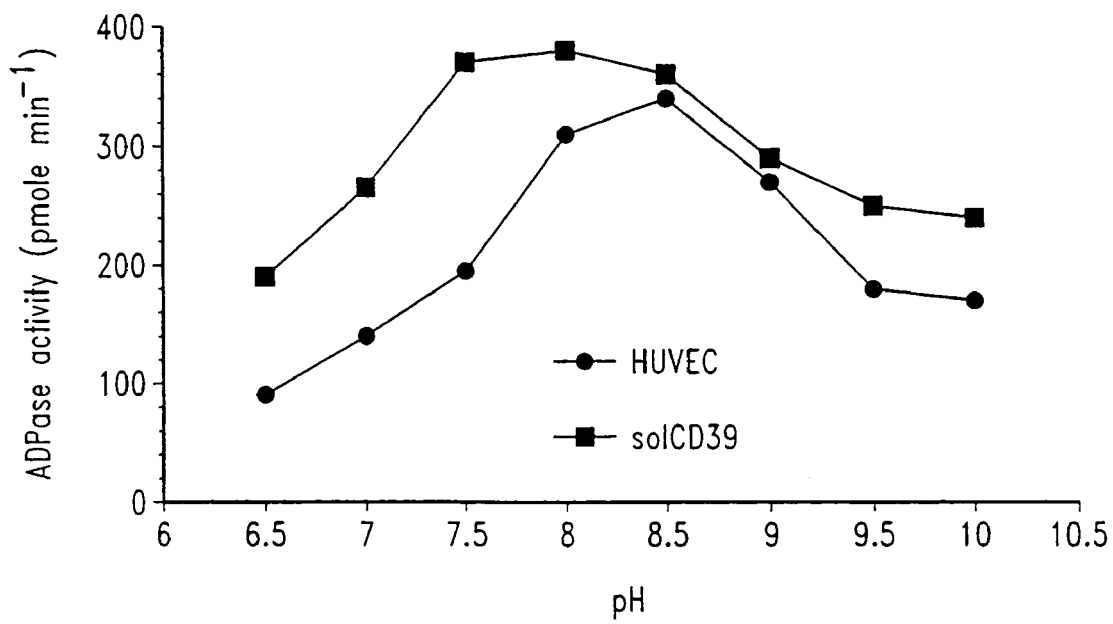
FIG. 6A shows pH optimum profiles of HUVEC membrane ecto-ADPase (●) and recombinant solCD39 (■).

As shown in FIG. 6A, the pH optima for the ecto-ADPase on the surface of HUVEC and for affinity-purified recombinant solCD39 ADPase activities were between pH 8 and 8.5. This indicated that recombinant solCD39 would be maximally active under the same physiological conditions as native CD39/ecto-ADPase.

Figure 6B:
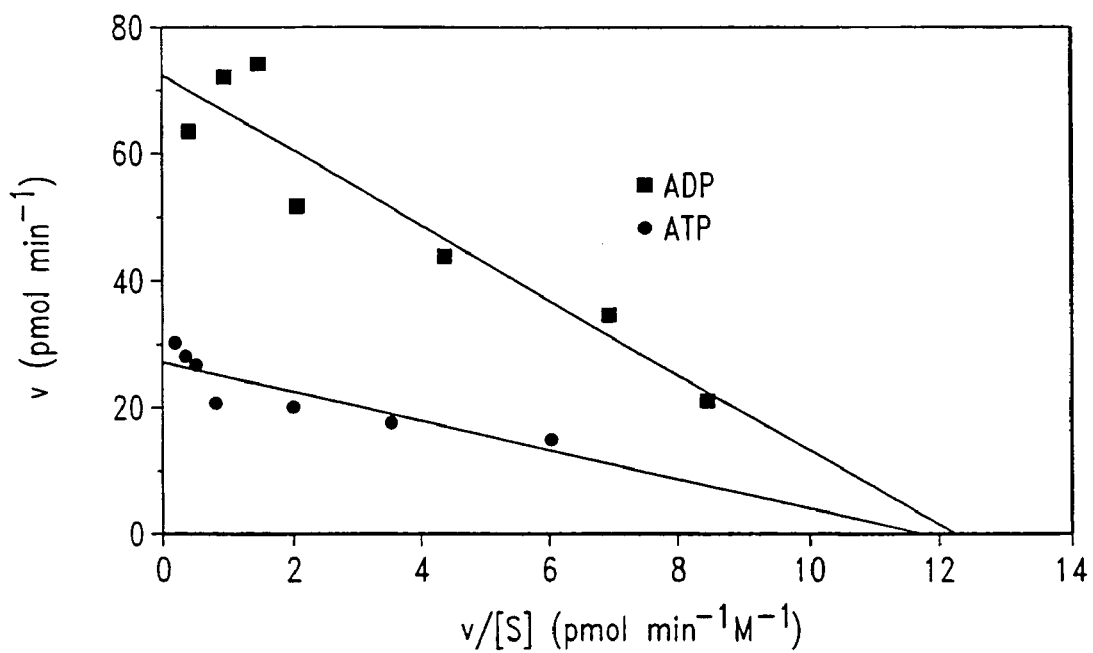
FIG. 6B shows is an Eadie-Hofstee plot of rates of metabolism at different concentrations of ATP (●) or ADP (■) using purified solCD39 (6.5 ng).

Initial rates of ATP and ADP metabolism by recombinant solCD39 were determined as shown in FIG. 6B, and kinetic constants were derived. The $K_m$ and $V_{max}$ for ADP were 5.9 µM and 72 pmol/min, respectively; for ATP a $K_m$ of 2.1 µM and $V_{max}$ of 26 pmol/min were determined. The assays were performed with $2 \times 10^{-9}$ M solCD39, yielding $k_{cat}$ of 720 min$^{-1}$ (ADP) and 260 min$^{-1}$ (ATP). Thus, the specificity constant, $k_{cat}/K_m$ ($1.2 \times 10^8$ min$^{-1}$ M$^{-1}$), was identical for ADP and ATP. The specific activity for purified recombinant solCD39 was 11 U/mg for ADP and 4 U/mg for ATP.

Example 15

Platelet Inhibitory Properties of solCD39

This example shows that recombinant affinity purified solCD39 is effective as an inhibitor of platelet activation and recruitment.

After obtaining informed consent from volunteers, blood was collected via plastic tubing using acid citrate-dextrose (38 mM citric acid; 75 mM sodium citrate; 135 mM glucose) as anticoagulant. Where indicated, volunteers had ingested 650 mg acetylsalicylic acid (ASA) 18 h prior to blood donation. Platelet-rich plasma (PRP) was prepared with an initial whole blood centrifugation (200 g, 15 min, 25° C.), and a second centrifugation of the PRP (90 g, 10 min) to eliminate residual erythrocytes and leukocytes. The stock suspension of PRP was maintained at room temperature under 5% CO$_2$-air.

A. Platelet Aggregation Studies

PRP containing $1.22 \times 10^8$ platelets was pre-incubated (3 min, 37° C.) in an aggregometer cuvette (Lumiaggregometer; Chrono-Log, Havertown, Pa.) alone or in combination with test samples containing solCD39. Total volumes were adjusted to 300 µl with TSG buffer (Marcus et al., *J. Clin. Invest.* 88:1690, 1991; Marcus et al., *J. Clin. Invest.* 99:1351, 1997). After the 3 min preincubation, platelet agonists (ADP or collagen) were added at the concentrations indicated, and the aggregation response recorded for 4-5 min. Where indicated, 10 µM indomethacin (Sigma, St. Louis, Mo.) was added to PRP to inhibit endogenous cyclooxygenase activity.

Figures 7A, 7B:
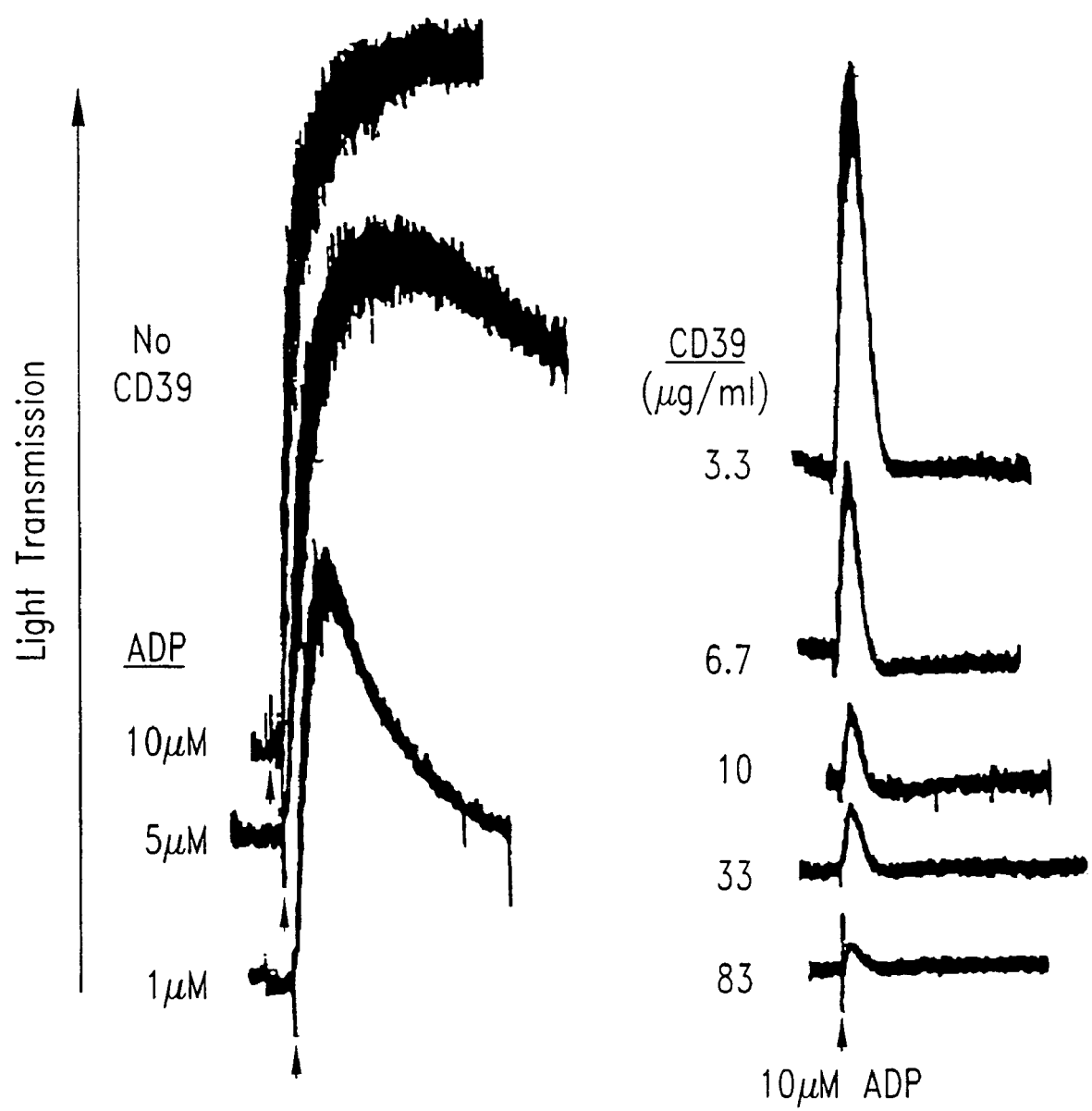
FIG. 7 shows inhibition of ADP-induced platelet reactivity by purified solCD39 in platelet-rich plasma from a donor who had ingested aspirin. The response to increasing concentrations of ADP is shown in FIG. 7A. The effect of increasing quantities of purified solCD39 on the platelet aggregation response to 10 µM ADP is shown in FIG. 7B. Arrows indicate the addition of agonist. Data are presented as relative light transmission vs. time (4 min duration).

As shown in FIG. 7, the addition of 10 µM ADP to PRP alone resulted in a full, irreversible aggregation response; partially reversible aggregation occurred at lower ADP concentrations. However, in the presence of only 3.3 µg/ml solCD39, platelet aggregation induced by 10 µM ADP was abruptly terminated and the curve rapidly returned to baseline. Importantly, the extent of aggregation was reduced to levels below those observed with 1 µM ADP. Higher concentrations of solCD39 had an even more profound inhibitory effect, virtually eliminating the initial burst of aggregation elicited by 10 µM ADP.

Platelet responsiveness to 5 µM ADP was examined in PRP treated with and without the cyclooxygenase inhibitor indomethacin (10 µM), in the presence of CM containing solCD39 from COS-1 and CHO cells. As shown in FIG. 8A, indomethacin treatment resulted in partial reversal of ADP-induced platelet aggregation in the absence of solCD39. In contrast, CM containing solCD39 were capable of completely abrogating platelet responses to ADP, whether PRP was indomethacin-treated or not.

Inhibition of platelet reactivity by CD39 was not limited to blocking the agonistic effects of ADP, as shown in FIGS. 8B and 8C. Collagen, which is another critical platelet agonist, was used at 1 µg/ml to induce platelet aggregation. The presence of solCD39 markedly reduced the response to collagen compared to control (FIG. 8B, upper curves). A similar inhibitory effect of solCD39 was observed in PRP treated with indomethacin (FIG. 8B, lower curves), when collagen was used at 3.3 µg/ml. As shown in FIG. 8C, the effect of solCD39 on collagen-induced aggregation was dose dependent.

B. Inactivation of Enzymatic Activity of solCD39 and the Effect on Inhibition of Platelet Activation To demonstrate that the ability of solCD39 to inhibit platelet activation and recruitment was due to the enzymatic activity of solCD39 and not to some other property, the solCD39 was reacted with FSBA (Fluorosulfonylbenzoyl-adenosine), an ATP analog that inhibits collagen-induced platelet activation (Colman et al., *Blood* 68:565, 1986) and binds irreversibly with ATPDases found on several cell types (Sevigny et al., *Biochem. Biophys. Acta* 1334:73, 1997; Sevigny et al., *Biochem. J.*, 312:351, 1995).

Figure 9A:
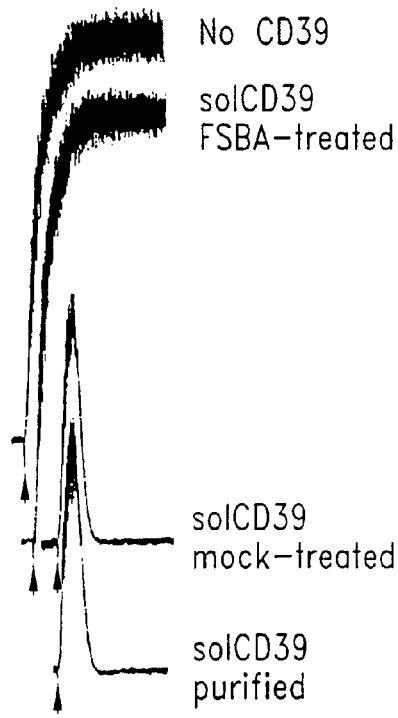
FIG. 9A shows the effects of purified solCD39, FSBA-treated solCD39, and mock-treated solCD39 (each at 4.4 µg/ml) on ASA-treated PRP after addition of 10 µM ADP.
Figure 9B:
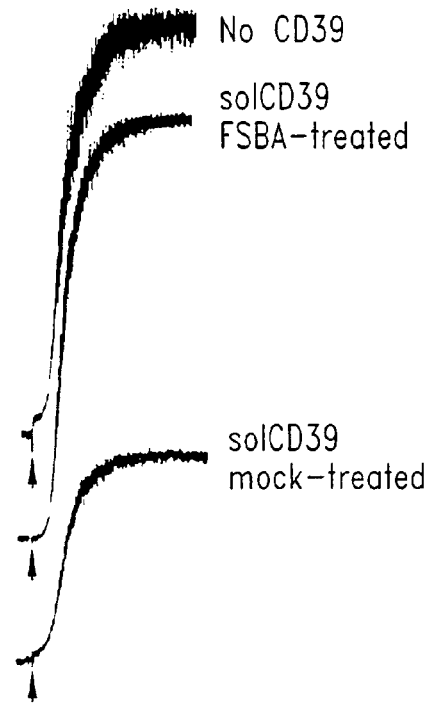
FIG. 9B shows the effects of FSBA-treated solCD39 and mock-treated solCD39 (each at 22 µg/ml) on ASA-treated PRP following addition of 3.3 µg/ml collagen.
Figure 9C:
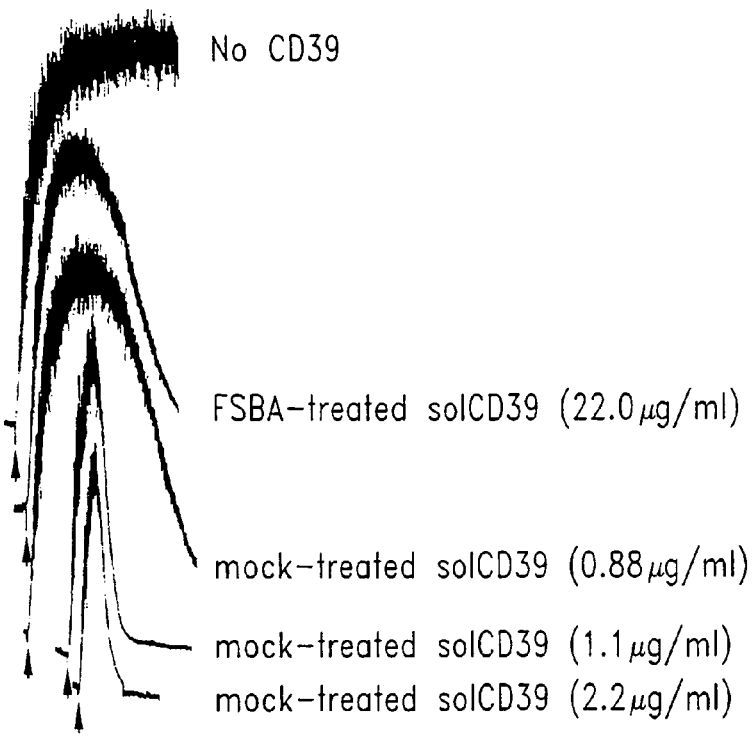
FIG. 9C shows the titration of mock-treated solCD39 (0.88-2.2 µg/ml) against FSBA-treated solCD39 (22 µg/ml). ASA-treated PRP was stimulated with 10 µM ADP. Arrows indicate addition of agonist. Data are presented as relative light transmission vs time.

SolCD39 (2 nmol) was combined with 2 ml labeling buffer (100 mM Hepes, pH 7.4, 200 mM NaCl, 4% dimethylformamide [vol/vol]), 400 µl 5 mM FSBA (Sigma Chemical Co.) dissolved in ethanol, and 1.52 ml water. A mock-treated sample was also prepared in which the FSBA solution was replaced with water. After incubating at 37° for 90 min., the samples were centrifuged in a Centricon-10 filter unit (Amicon Corp.) for 1 hour at 5,500 rpm and buffer exchanged into PBS to remove unreacted material. The effect of FSBA-treated solCD39 on platelet reactivity is shown in FIG. 9.

Induction of platelet activation by ADP (FIG. 9A) or collagen (FIG. 9B) was significantly inhibited by either purified solCD39 or mock FSBA-treated solCD39. In contrast, incubation with FSBA-treated solCD39 did not have a significant effect on platelet activation. A comparative titration of mock-treated solCD39 verses FSBA-treated solCD39 (FIG. 9C) indicated that 22.0 µg/ml of FSBA-treated sol CD39 gave a similar aggregation profile as 0.88 µg/ml of mock-treated solCD39. This indicated that 96% of the aggregation inhibitory activity of solCD39 was lost after FSBA derivitization. Analyses of residual ADPase activity of FSBA-treated solCD39 by the radio-TLC assay system demonstrated that approx. 94% of the enzymatic activity was blocked, while the phosphate release assay indicated that a similar percentage of the ATPase activity was lost as well.

C. Mutagenesis Studies

To identify amino acids involved in the biological activity of solCD39, site directed mutagenesis was used to alter selected amino acid residues in CD39. Mutants were assayed for enzymatic (ATPase and ADPase) and platelet inhibitory (dose-dependent inhibition of platelet aggregation) activities. For one series of mutants, residues within the conserved apyrase regions were replaced with alanine.

Platelet inhibitory activity correlated generally with enzymatic activity. The E174A mutant (residues are numbered as in FIG. 1) was completely devoid of enzymatic activity and had no effect on platelet responsiveness; the S218A mutant retained less than 10% of ADPase activity and approx. 10% of platelet inhibitory activity. Glutamate174 and Serine218 therefore appear to be important for both the enzymatic and platelet inhibitory activities of CD39.

Additional mutant forms of CD39 are expressed and assayed for enzymatic and platelet inhibitory activity in order to identify mutants with increased or decreased activity as well as mutants that preferentially catalyze the ATPase or ADPase reaction.

Example 16

Persistence of solCD39 Following In Vivo Administration in Mice

Balb/c mice (6-8 weeks of age; maintained under specific pathogen-free conditions; Jackson Laboratory, Bar Harbor, Me.) were intravenously injected with 50 µg recombinant solCD39 in 100 µl sterile saline (0.9% NaCl). No overt external difficulties were noted in the animals following injection. At various times after injection (5, 10, 30 min, 1, 2, 4, 8, 24 h), pairs of mice were bled by cardiac puncture and euthanized. Serum was prepared from each blood sample and frozen until assay. The presence of biologically active solCD39 in serum samples was measured in ATPase and ADPase assays. The data were fit using Deltagraph (Deltapoint, Monterey, Calif.). The best fit was derived using double exponential decay. Where indicated, specificity of enzyme activity was determined by incubating serum samples with anti-CD39 mAb-coated beads to remove CD39 prior to testing for ATPase activity.

Figure 10:
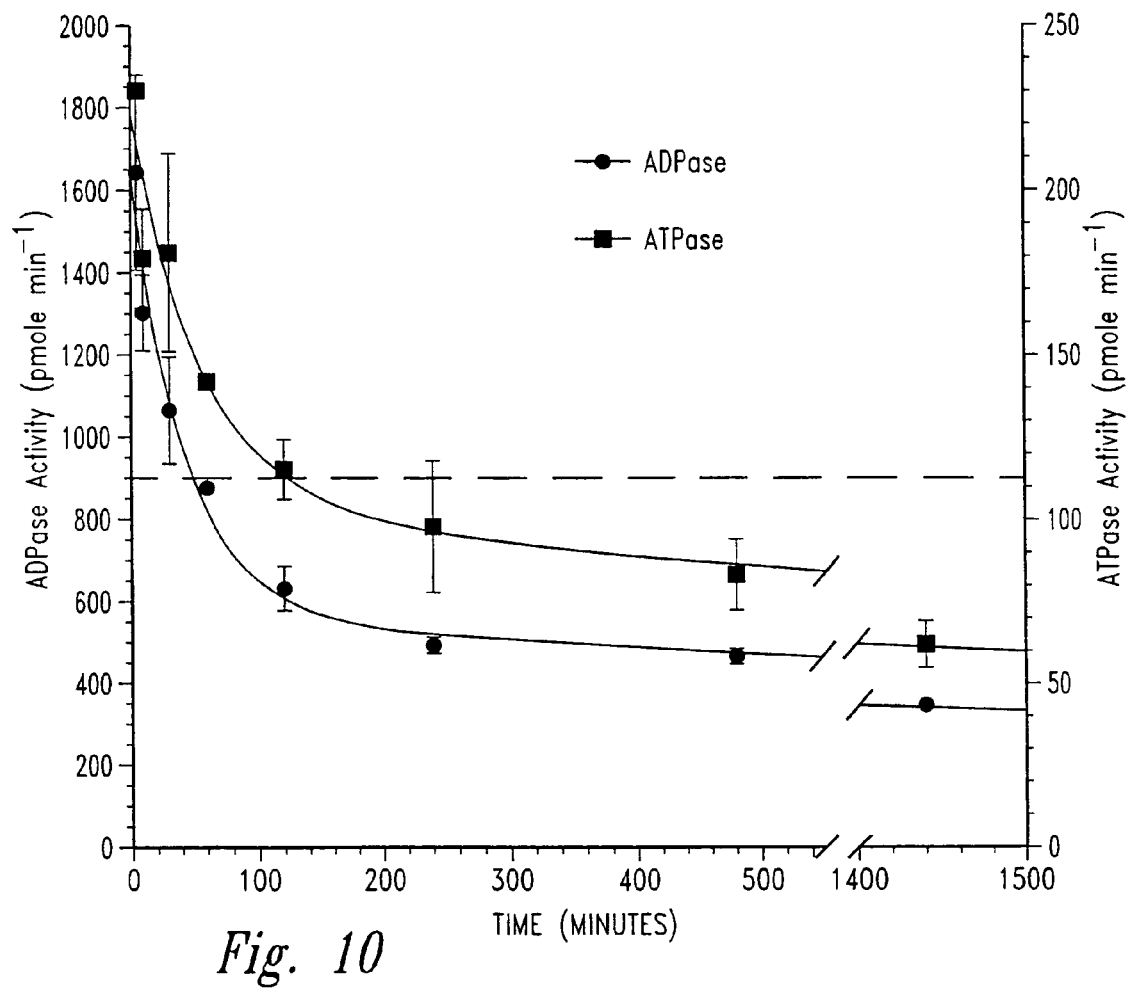
FIG. 10 shows pharmacokinetic analyses of solCD39 in mice. CD39 in serum was measured in the radioactive phosphate release ATPase assay (■) or the ADPase assay (●). Activities are expressed as pmoles nucleotide degraded per minute. The dashed line indicates the ATPase activity of 25 µg/ml of solCD39 in murine serum. Distribution ($t_{1/2}\alpha$=59 min (ATP); 43 min (ADP)) and clearance ($t_{1/2}\beta$=40 h (ATP & ADP)) half-lives were determined using a biphasic curve fit.

As shown in FIG. 10, the data obtained best fit a biphasic exponential curve. The amount of ATPase activity from 25 µg/ml of solCD39 placed in murine serum is presented for comparison. The $t_{1/2}\alpha$ (distribution phase) was calculated to be 59 min in the ATPase assay and 43 min in the ADPase assay. Approximately 55-65% of apyrase activity was cleared from the circulation during this phase. The elimination phase had a $t_{1/2}\beta$ of approximately 40 h in both assays. Preclearing the 10 min, 2 h, and 24 h time point samples with anti-CD39 mAb-coated beads completely eliminated serum ATPase/ADPase activities. These data also demonstrate that the assays specifically detect recombinant human solCD39.

Example 17

Pilot Dose Ranging Study in Yorkshire-Hampshire Pigs

SolCD39 was administered to Yorkshire-Hampshire pigs, which have been developed as a porcine model of thrombosis. Following intravenous injection, CD39 persisted in the circulation and was capable of inhibiting platelet aggregation and recruitment for as much as a week following injection. This is in marked contrast to many other therapeutic agents used for platelet inhibition, wherein the duration of inhibition is very short.

Ten pigs were randomly assigned to receive solCD39 in low (72 µg/kg), medium (221 µg/kg), or high (670 µg/kg) doses. Aspirin was administered orally on a daily basis. Placebo controls consisted of aspirin. Saline controls and solCD39 were administered as a single bolus. Time points were measured following this administration. Blood samples were obtained via an external jugular vein catheter. Bleeding times were measured in pigs receiving placebo controls and in those receiving solCD39 at baseline and at 60 minutes. ADP-induced platelet aggregation was measured at specific time intervals following administration. The concentration of CD39 in serum as a function of time was measured using an ELISA assay.

Administration of solCD39 was well tolerated. It did not induce anemia or thrombocytopenia and, importantly, a second dose of solCD39 could be administered without observable ill effects, such as hypotension, thrombocytopenia, or hemorrhage. Clot retraction was normal following all experiments, indicating that platelet function was essentially normal.

A. Effect of solCD39 on Bleeding Time

Figure 11:
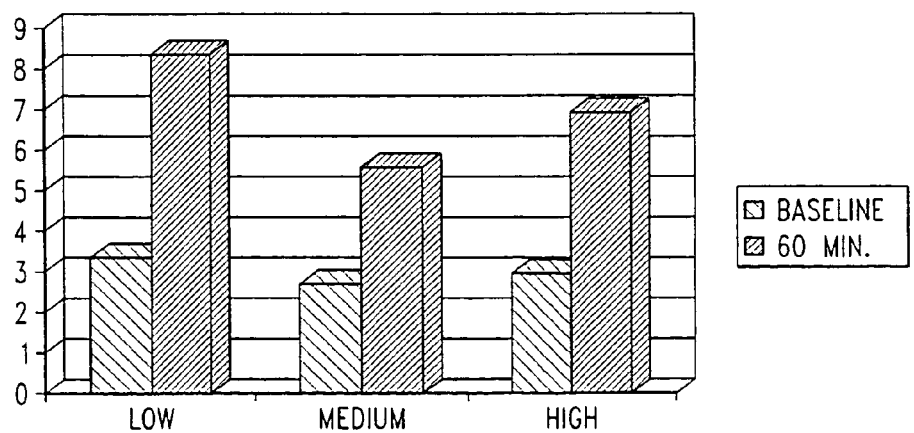
FIG. 11 shows bleeding times at 0 and 60 minutes in pigs treated with low, medium, or high doses of solCD39.

Bleeding time is an absolute measure of platelet function. As shown in FIG. 11, solCD39 induced a prolonged bleeding time. This indicated that a therapeutic effect had been obtained via a mild interference with platelet function. These mild increases in bleeding time were similar to those obtained by aspirin administration. This indicates that the hemorrhagic defect was mild.

B. Effects of Aspirin and solCD39 on Platelet Aggregation

Figure 12A:
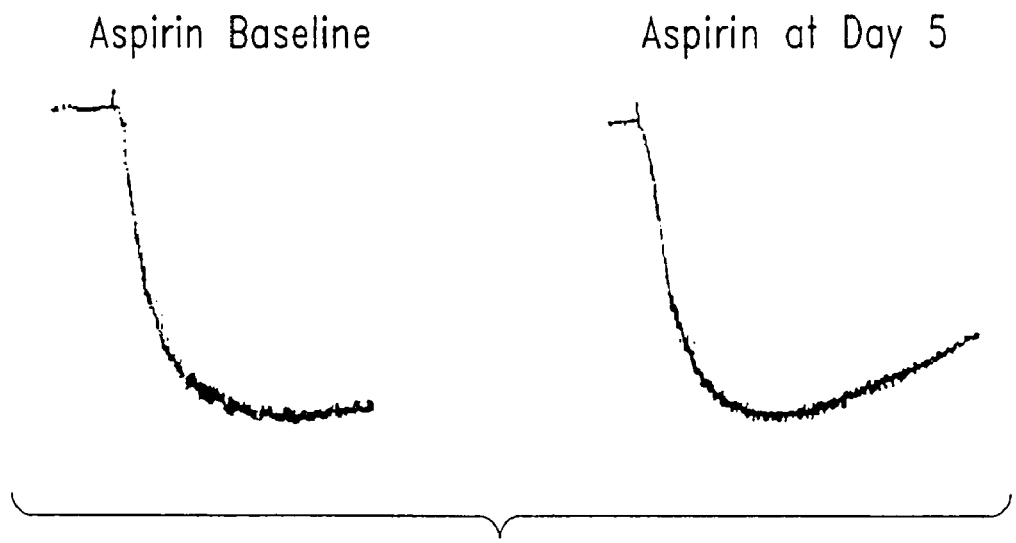
FIG. 12 shows the effect of aspirin on pig platelet aggregation at baseline and day 5 after intravenous administration (FIG. 12A) and the effect of effect of high dose solCD39 on platelet aggregation at baseline and day 7 (FIG. 12B).
Figure 12B:
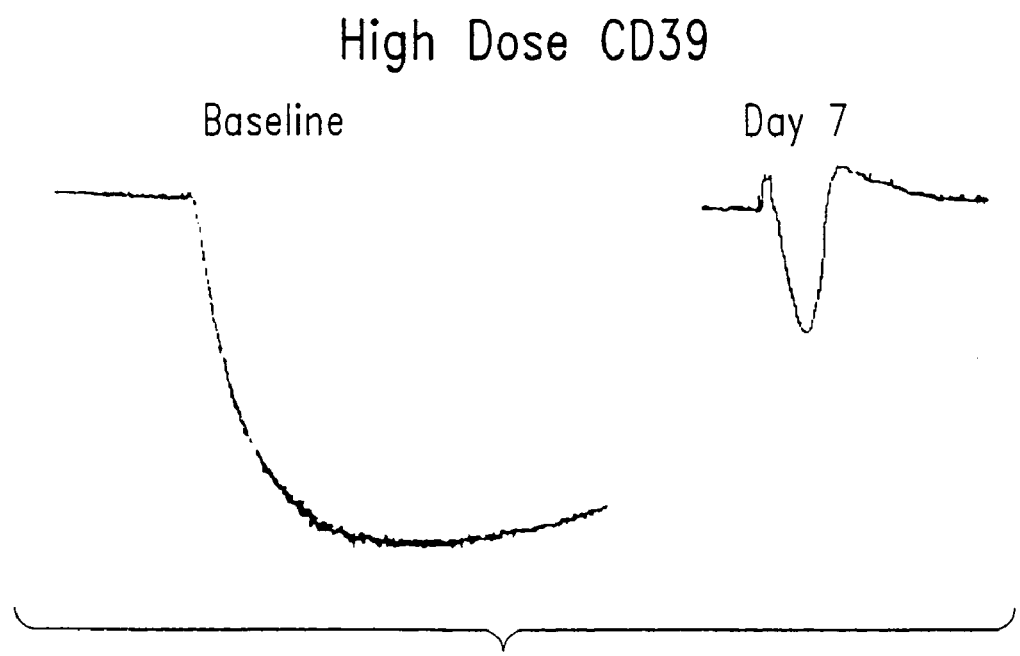
Figure 13:
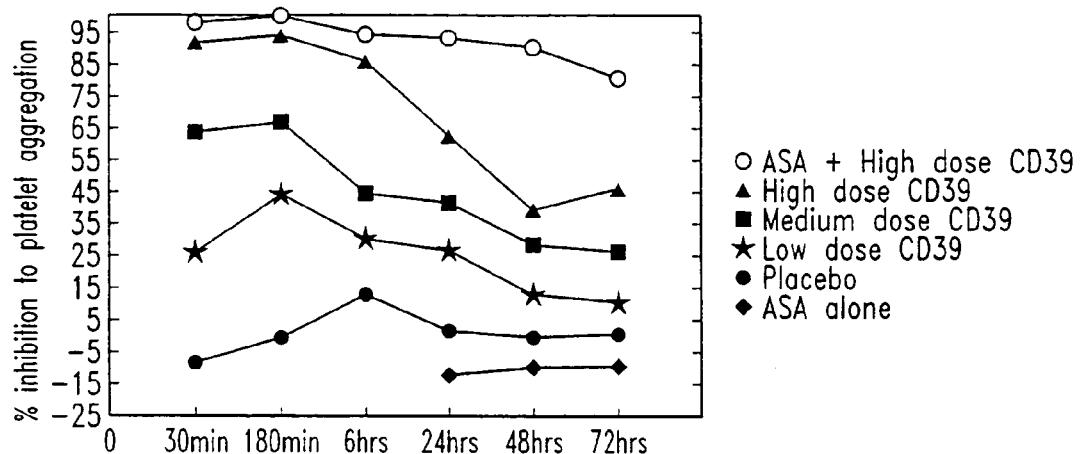
FIG. 13 shows the inhibition of pig platelet aggregation by low, medium, and high doses of solCD39 as a function of time after bolus administration.

FIG. 12A shows the effect of aspirin on platelet aggregation at baseline and at day 5, and FIG. 12B shows the effect of high dose solCD39 on platelet aggregation at baseline and at day 7. Peak heights from the platelet aggregation curves for each of the three solCD39 doses are plotted in FIG. 13. The platelet aggregation data are also compared by plotting relative areas from the platelet aggregation curves for each of the three solCD39 doses. A dose of 670 µg/kg inhibited greater than 90% of ADP induced platelet aggregation. The inhibitory effect was long-lived, with 30% inhibition (after high dose solCD39) at two weeks. These experiments show that solCD39 has potent and long lasting anti-platelet effects, and that these effects are superior to those obtained using aspirin.

C. Persistence of solCD39 in Serum

Figure 14:
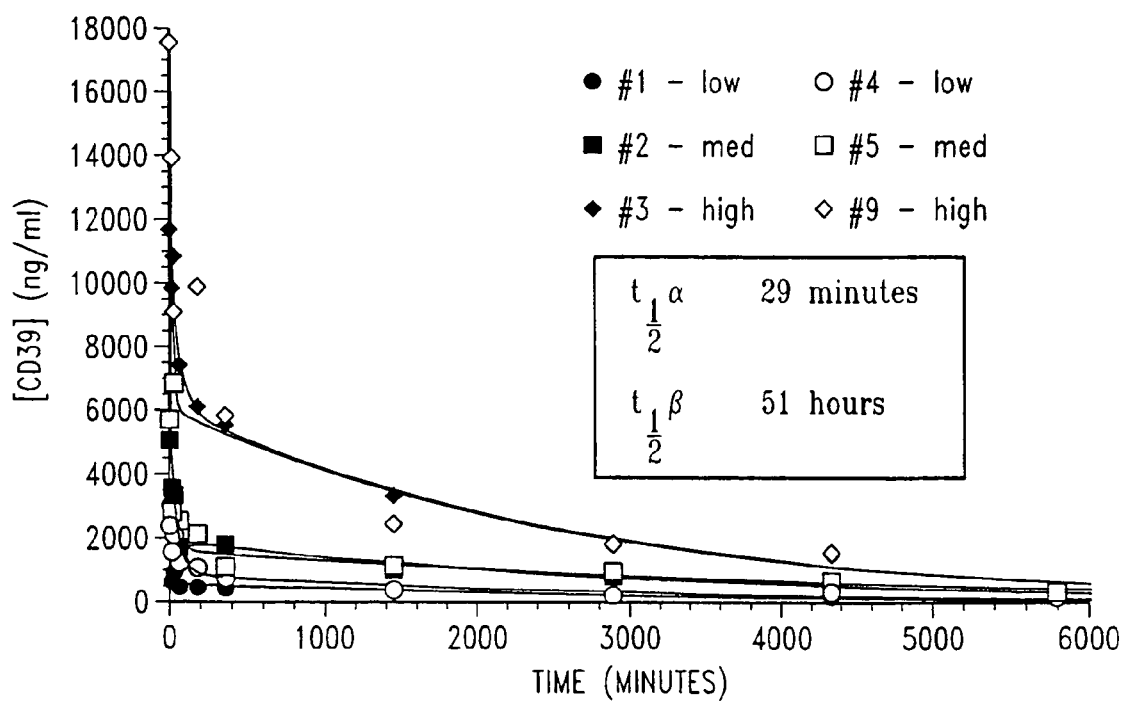
FIG. 14 shows the concentration of CD39 in pig serum as a function of time after low, medium, or high dose administration. Distribution ($t_{1/2}\alpha$=29 min) and clearance ($t_{1/2}\beta$=51 h) half-lives were determined using a biphasic curve fit.

The persistence of solCD39 in porcine serum, as determined by ELISA, is shown in FIG. 14. Distribution and clearance half-lives were determined using a biphasic curve fit. The $t_{1/2}\alpha$ (distribution phase) was calculated to be 29 minutes. The elimination phase had a $t_{1/2}\beta$ of approximately 51 hours. SolCD39 biological activity (ADPase activity) also exhibited a long elimination half-life, approaching 5-7 days, and could still be detected over two weeks after administration. During this time there were no changes in hematologic parameters and no evidence of hemorrhage despite tripling of the bleeding time.

D. Percutaneous Transluminal Coronary Angioplasty (PTCA) Study

Porcine platelets and fibrinogen were labeled with $^{111}$Indium and $^{125}$Iodine respectively for infusion into pigs. Twelve pigs were sedated and anesthetized, and randomly assigned to receive intravenous solCD39 (670 µg/kg) plus heparin and ASA or intravenous saline placebo plus heparin and ASA. Oral ASA was given to all pigs for at least three day prior to the coronary angioplasty procedure, and heparin (100 U/kg) was given at the time of the angioplasty. One to three days prior to the angioplasty an external jugular line was inserted to administer the labeled platelets and fibrin, CD39 or saline, and to facilitate blood draws. Labeled platelets and fibrinogen were given approximately 18 hours prior to balloon injury. Coronary arteries were injured using an oversize balloon. A coronary guide catheter was first advanced into the ascending aorta. An oversized balloon was then advanced into a coronary vessel and inflated at 6 to 8 atmospheres for a total of thirty seconds. The balloon was then deflated and withdrawn. The average ratio of balloon size to vessel size was 1.32 for the placebo group and 1.29 for the CD39 group.

Platelet aggregation and bleeding time were measured 30 minutes after administration. The pigs were killed 24 hours after balloon injury and solCD39 administration, and the labeled platelet ($^{111}$Indium) and fibrin ($^{125}$Iodine) deposition per cm$^2$ was measured in the injured coronary artery segments. The results are summarized in TABLE 7. CD39 administration was well tolerated without bleeding or hemodynamic complications. Moreover, no bleeding was noted during PTCA or after sheath removal and there was no significant difference in hematocrit or platelet counts between the groups.

These results show that the administration of solCD39 results in a significant inhibition of platelet aggregation and prolongation of bleeding time, as well as a trend toward inhibition of platelet and fibrin deposition, after balloon injury in animals. The results also suggest that CD 39 has a minimal risk of inducing bleeding.

TABLE 7

Effects of solCD39 After Balloon Injury

| Treatment | Platelet Deposition Ratio | Fibrin Deposition Ratio | Bleeding Time | % Inhibition of Platelet Aggregation |
|---|---|---|---|---|
| Placebo | 1.78 ± 0.4 | 0.71 ± 0.14 | 3.03 ± 0.2 | 1 ± 10 |
| solCD39 | 1.25 ± 0.19 | 0.62 ± 0.10 | 7.00 ± 0.81 | 80 ± 2 |
| p = value | 0.2 | 0.5 | 0.009 | 0.001 |

After the radioactivity decayed, toluidine-blue stained injured coronary artery segments were examined histologically, in order to further characterize the extent of thrombus formation. A blinded observer qualitatively evaluated the degree of histologic injury in the coronary segments by assessing, on a scale of 1-4 with 4 being the most severe injury, the severity of medial and internal elastic lamina tear, medial separation, and hemorrhage. A composite injury score was obtained by totaling, the three individual scores. The medial injury scores for the placebo and CD39 groups were 2.5 and 2.2 respectively; medial separation scores for the placebo and CD39 groups were 2.0 and 1.6 respectively; the degree of hemorrhage for the placebo and CD39 groups were 2.3 and 2.5 respectively. The composite injury scores for the placebo and CD39 groups were 6.6 and 6.2 respectively. These in vivo results correlate well with results, reported herein, obtained in vitro and ex vivo.

Example 18

Soluble CD39 Provides Additive Inhibition of Platelet Aggregation Over Aspirin and Abciximab An ex vivo study was performed in order to evaluate the additive inhibition of platelet aggregation when soluble CD39 is added to platelet rich plasma from patients receiving: placebo, aspirin, clopidogrel, ticlopidine, or abciximab. Each group consisted of three to six patients. The clopidogrel, ticlopidine, and abciximab groups also received aspirin. Baseline platelet aggregation was measured for each group, in response to the platelet agonists ADP, collagen, or the Thrombin Receptor Activating Peptide $TRAP_{1-6}$. SolCD39 (10 µg/ml or 100 µg/ml) was then added and the additional inhibition of platelet activation (over baseline, in response to the platelet agonists) was measured in each of the five groups. The result are shown in TABLE 8.

TABLE 8

Additive Inhibition of Platelet Aggregation by Soluble CD39

| | Group | | | | |
|---|---|---|---|---|---|
| | Placebo | Aspirin | Clopidogrel | Ticlopidine | Abciximab |
| Baseline | | | | | |
| ADP | 84 ± 4[1] | 69 ± 5 | 58 ± 6 | 76 ± 3 | 0 ± 0 |
| Collagen | 85 ± 1 | 62 ± 8 | 57 ± 9 | 71 ± 17 | 0 ± 0 |
| TRAP | 94 ± 2 | 66 ± 6 | 51 ± 2 | 26 ± 5 | 46 ± 6 |
| SolCD39 10 µg/ml | | | | | |
| ADP | 0 ± 0 100%[2] | 4 ± 2 97% | 5 ± 2 92% | 10 ± 2 86% | 0 ± 0 100% |
| Collagen | 75 ± 2 11% | 21 ± 4 68% | 31 ± 9 48% | 48 ± 18 37% | 0 ± 0 100% |
| TRAP | 70 ± 3 | 38 ± 7 | 35 ± 1 | 19 ± 6 | 22 ± 10 |

TABLE 8-continued

Additive Inhibition of Platelet Aggregation by Soluble CD39

| | Group | | | | |
|---|---|---|---|---|---|
| | Placebo | Aspirin | Clopidogrel | Ticlopidine | Abciximab |
| SolCD39 100 µg/ml | 26% | 45% | 31% | 33% | 52% |
| ADP | 0 ± 0 | 1 ± 0 | 0 ± 0 | 2 ± 2 | 0 ± 0 |
| | 100% | 99% | 100% | 97% | 100% |
| Collagen | 57 ± 5 | 16 ± 4 | 21 ± 6 | 37 ± 15 | 0 ± 0 |
| | 33% | 75% | 64% | 53% | 100% |
| TRAP | 65 ± 4 | 26 ± 5 | 23 ± 3 | 18 ± 7 | 22 ± 9 |
| | 30% | 63% | 55% | 36% | 52% |

[1]Platelet aggregation, arbitrary units
[2]Percent inhibition relative to same agonist in the absence of CD39

Soluble CD39 at a concentration of 10 µg/ml synergistically inhibited ADP, collagen, and TRAP mediated platelet aggregation in patients on aspirin (p<0.001), and this effect was independent of clopidogrel and ticlopidine. Abciximab alone abolished platelet aggregation due to ADP and collagen, but CD39 provided synergistic inhibition of platelet aggregation induced by TRAP (p<0.007). Soluble CD39 at 100 µg/ml provided increased inhibition of platelet aggregation to all agonists. These results were also seen in vitro. Collagen and TRAP induce platelet aggregation via mechanisms in addition to ADP release and recruitment, so the ability of CD39 to inhibit collagen and TRAP-mediated platelet aggregation suggests additional versatility of CD39 as an anti thrombotic agent.

Example 19

Soluble CD39 Inhibits Thrombosis and Limits Ischemic Cerebral Injury in Wild Type and Reconstituted CD39 Null Mice The above examples suggested that soluble CD39 would inhibit ADP-mediated amplification of platelet recruitment in distal microvessels, thereby reducing thrombosis after stroke. The following experiments illustrate the use of CD39 in a microvascular thrombosis (murine ischemic stroke) model. Soluble CD39 inhibited microvascular thrombosis and conferred cerebroprotection in stroke. A notable feature of the solCD39 treatment was the low incidence of intracerebral hemorrhage relative to that reported for other antithrombotic agents.

A. Materials and Methods

C57BL/6J mice (6-8 wk) were obtained from Jackson Laboratories (Bar Harbor, Me.). Untreated mice, and mice treated with 4 mg/kg solCD39, with 5 mg/kg aspirin or phosphate buffered saline, were anesthetized and heparinized (10 U/g), prior to blood collection via cardiac puncture. 80 µL of 3.8% trisodium citrate was added to each mL of blood. Samples from 6-8 mice were pooled and platelet-rich plasma (PRP) was prepared by centrifugation. The PRP contained 400-700×10³ platelets per µL. All experiments were completed within 2 hours of blood collection. PRP (200 µL) was preincubated, for 3 min. at 37° C., with 100 µL Tris-buffered saline buffer (15 mM NaCl, 5 mM glucose, pH 7.4) in an aggregometer cuvette (Lumiaggregometer; Chrono-Log, Havertown, Pa.), and the platelet agonists ADP, collagen, or sodium arachidonate were added at the final concentrations indicated. Aggregation responses were recorded for 2-4 min, and expressed as area under the curve (height times width at ½ height).

The effects of soluble CD39 were tested in a previously validated murine model of stroke injury (Choudhri, T. F., et al., J. Clin. Invest. 102:1301-1310 (1998); Connolly, E. S., Jr., et al., J. Clin. Invest. 97:209-216 (1996); and Connolly, E. S., Jr., et al., Neurosurg. 38(3):523-532 (1996)). Anesthetized mice were maintained at 37±2° C. during and for 90 min following surgery. A midline neck incision was made and the right carotid artery exposed. Middle cerebral artery occlusion was accomplished by advancing a 13-mm heat-blunt tipped 6-0 nylon suture via an arteriotomy in the external carotid stump. The external carotid artery was cauterized to secure hemostasis, and arterial flow reestablished. Carotid artery occlusion never exceed 3 min. The occluding suture was removed after 45 min and cautery was again locally applied to prevent bleeding at the arteriotomy site. Surgical staples were used for wound closure.

Doppler measurement of cerebral cortical blood flow, neurological score (Huang, Z., et al., Science 265:183-1885 (1994)), calculation of infarct volume, measurement of cerebral thrombosis using ¹¹¹In-labeled platelets (Choudhri, T. F., et al., J. Clin. Invest. 102:1301-1310 (1998) and Naka, Y., et al., Circ. Res. 76:900-906 (1995)), detection of intracerebral fibrin (Choudhri, T. F., et al., J. Clin. Invest. 102: 1301-1310 (1998)), and measurement of intracerebral hemorrhage (Choudhri, T. F., et al., J. Clin. Invest. 102:1301-1310 (1998) and Choudhri, T. F. et al., Stroke 28:2296-2302 (1997)) were measured as previously described. The results are described below.

B. Soluble CD39 Abrogates the Ex Vivo Aggregation of Murine Platelets

Figure 15A:
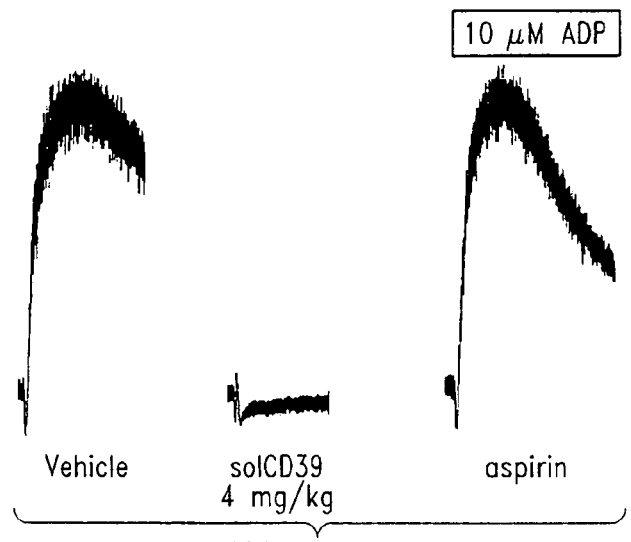
FIG. 15 shows the ex vivo aggregation of murine platelets. Platelets were stimulated with 10 µM ADP (FIG. 15A), 2.5 µg/ml collagen (FIG. 15B), or 0.1 mM sodium arachidonate (FIG. 15C) after the administration of vehicle (saline), soluble CD39 (4 mg/kg) or aspirin (5 mg/kg). Soluble CD39 treatment produced aggregation curves that returned to baseline following stimulation with agonists, but aspirin treatment yielded such a pattern only when arachidonate was the agonist.
Figure 15B:
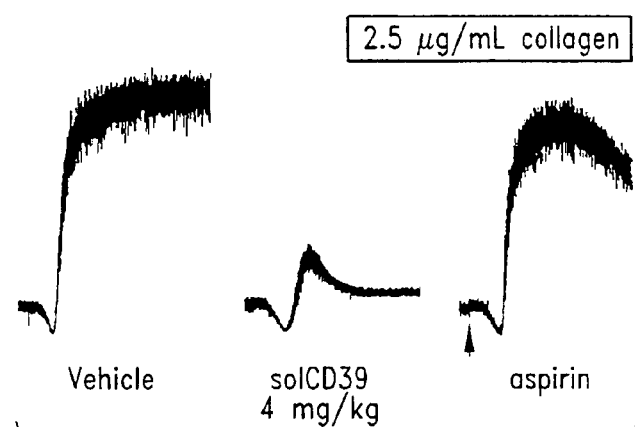

Platelet-rich plasma was obtained from mice 1 hour after injection of saline (vehicle), soluble CD39, or aspirin. Ex vivo platelet aggregation was studied to ascertain the relative potency of solCD39 as compared to aspirin (which can improve the outcome following a transient ischemic attack). Platelets from control and aspirin-treated mice strongly aggregated following stimulation with ADP (FIG. 15A) or collagen (FIG. 15B).

Figure 15C:
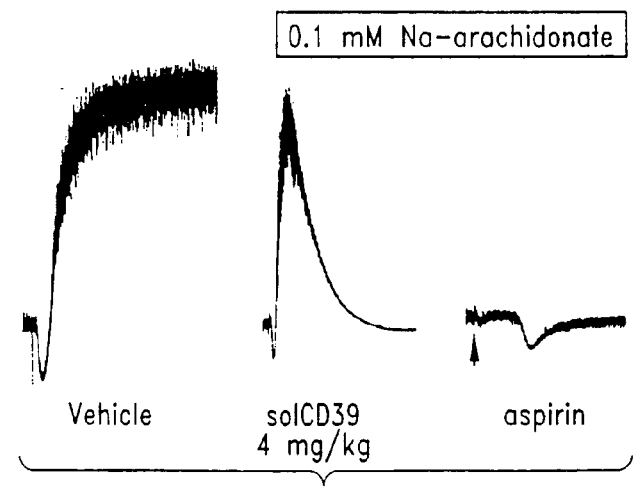

Soluble CD39 abrogated platelet aggregation in the presence of ADP, and attenuated aggregation in the presence of collagen and arachidonate. In contrast, aspirin treatment only blocked platelet reactivity to arachidonate (FIG. 15C). The platelets from mice pretreated with solCD39 showed an initial aggregation in the presence of arachidonate, but rapidly disaggregated and returned to the resting state before a full response occurred (FIG. 15C).

Figure 16:
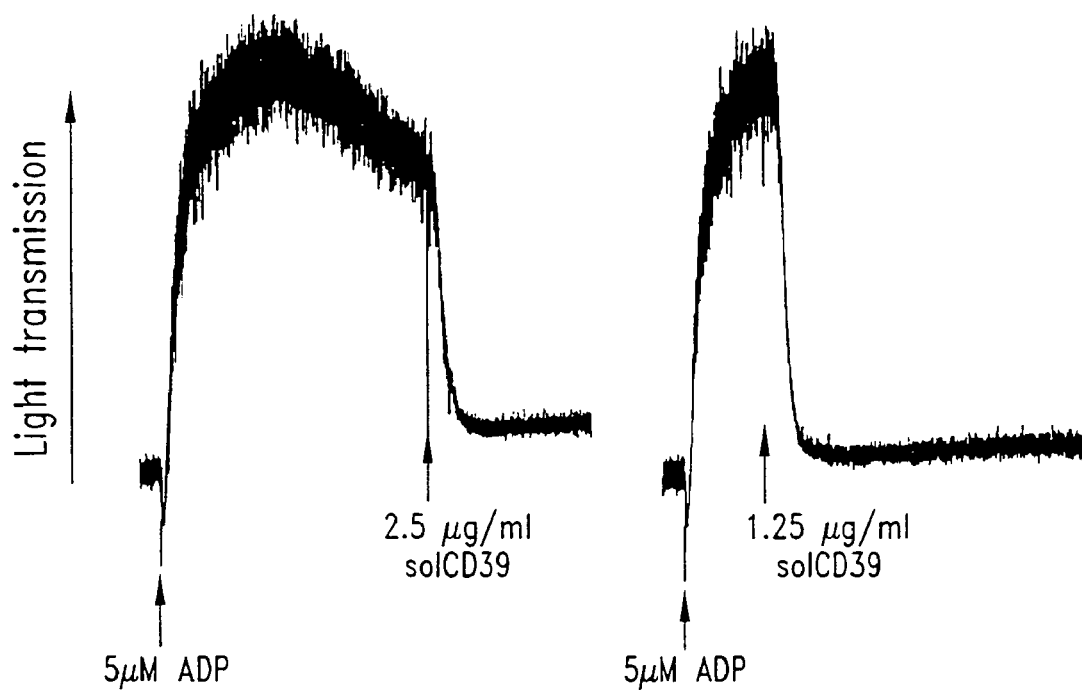
FIG. 16 shows reversal of the ADP-induced aggregation response in murine platelets when solCD39 is added at the peak of the aggregation response.

C. Soluble CD39 Is Effective Even When Added at the Peak of the Aggregation Response ADP (5 µM) was added to mouse platelets in vitro to induce an aggregation response. Soluble CD39 (2.5 µg/ml or 1.25 µg/ml) was added at the peak of the aggregation response. The solCD39 immediately reversed the aggregation response, as shown in FIG. 16. This result demonstrates that SolCD39 is able to reverse an aggregation response, rapidly returning platelets to a resting state, even when added at the peak of the response. This result likely reflects the fact that at the peak of the aggregation response ADP is prominent in the releasate from the aggregating platelets. Soluble CD39 metabolizes this ADP to the biologically inactive compound AMP almost instantaneously, accounting for the rapid descent of the aggregation curve in FIG. 16, right side.

D. Soluble CD39 Reduces the Sequelae of Stroke

Figure 17A:
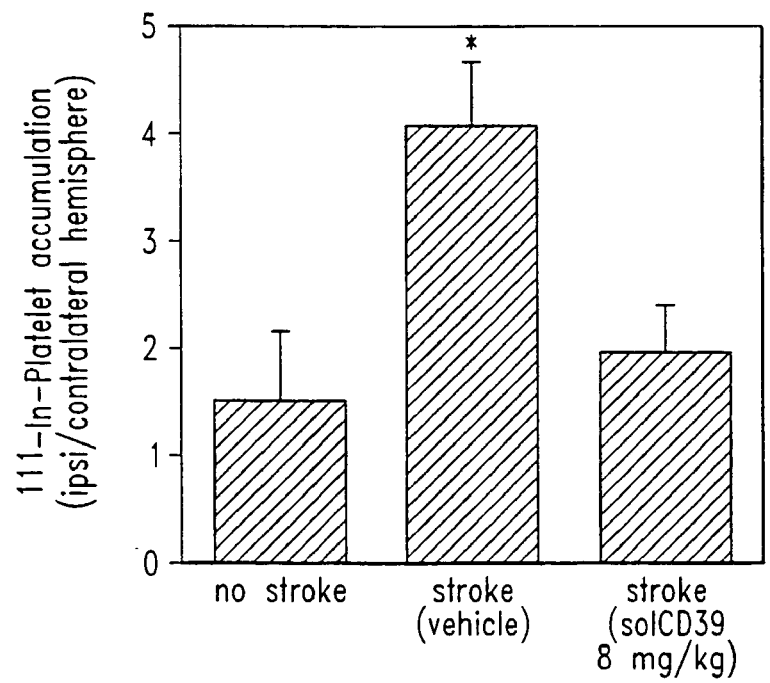
FIG. 17 shows the inhibition of platelet (n=20, FIG. 17A) and fibrin (n=3, FIG. 17B) deposition following induction of stroke in mice pretreated with 8 mg/kg soluble CD39. "Fibrin" is a positive control, "Ipsilat" is ipsilateral (i.e., the ischemic hemisphere), and "Contralat" is the nonischemic hemisphere.
Figure 17B:
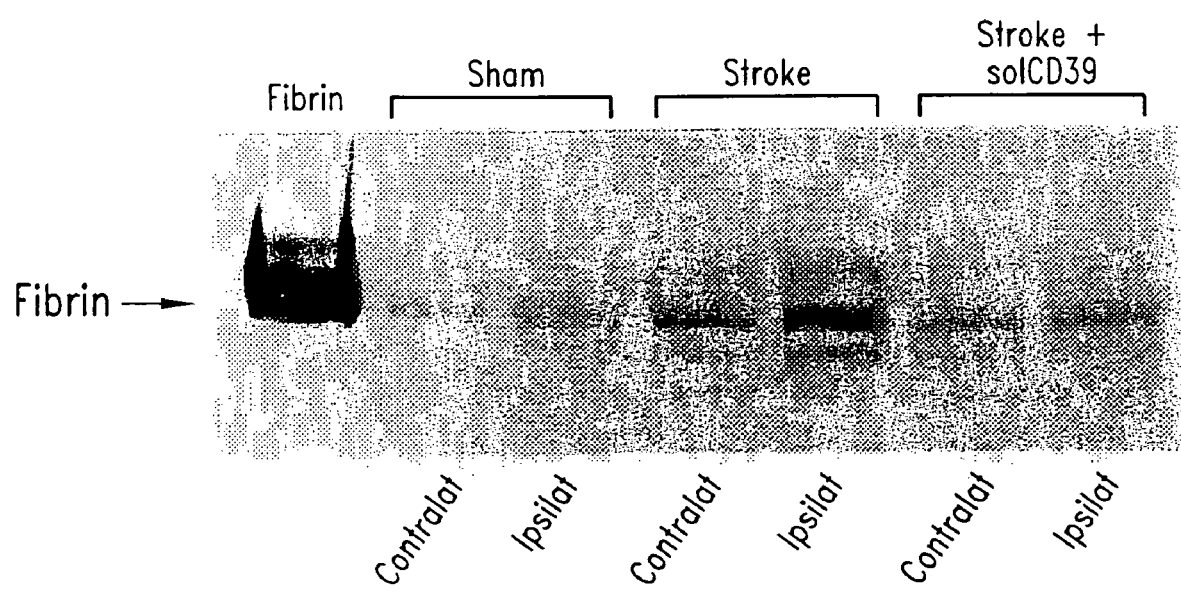

Intravenously injected soluble CD39 showed therapeutic utility in stroke. Soluble CD39 inhibited platelet accumulation in the ipsilateral cerebral hemisphere following induction of stroke, as shown in FIG. 17A. Similarly, solCD39 decreased the level of fibrin accumulation in the ipsilateral hemisphere (vs. contralateral) as measured by Western blot analysis using a fibrin specific antibody (FIG. 17B).

Figure 18A:
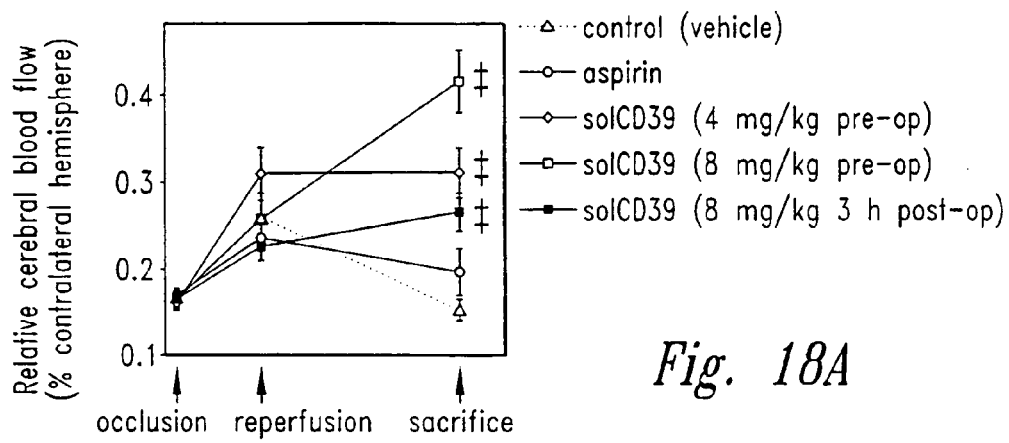
FIG. 18A shows cerebral blood flow, 18B shows cerebral infarct volume, 18C shows neurological score (where higher scores indicate a worse deficit (Connolly, E. S., Jr., et al., Neurosurg. 38(3):523-532 (1996)), 18D shows mortality, and 18E shows intracerebral hemorrhage. *$p<0.05$, ‡$p<0.01$, †$p<0.001$.

The ability of solCD39 to reduce thrombosis, as measured by decreased platelet and fibrin deposition, was accompanied by improved postischemic cerebral perfusion 24 hours after stroke induction, as shown in FIG. 18A. In contrast, when aspirin was administered at a clinically relevant dose (that inhibited the ex vivo response of platelets to arachidonate) no improvement was seen in postischemic cerebral blood flow (FIG. 18A).

Figure 18B:
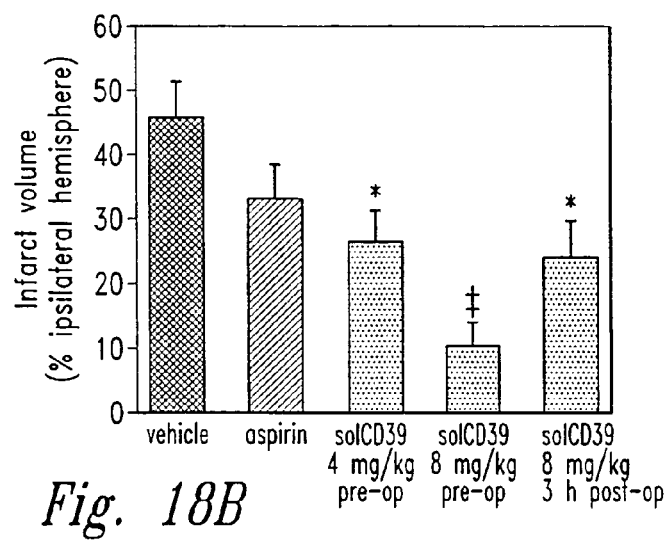
FIG. 18 shows the comparative effects of vehicle (n=23), soluble CD39 (n=67) and aspirin (n=27) on the outcome of induced stroke in mice.
Figure 18C:
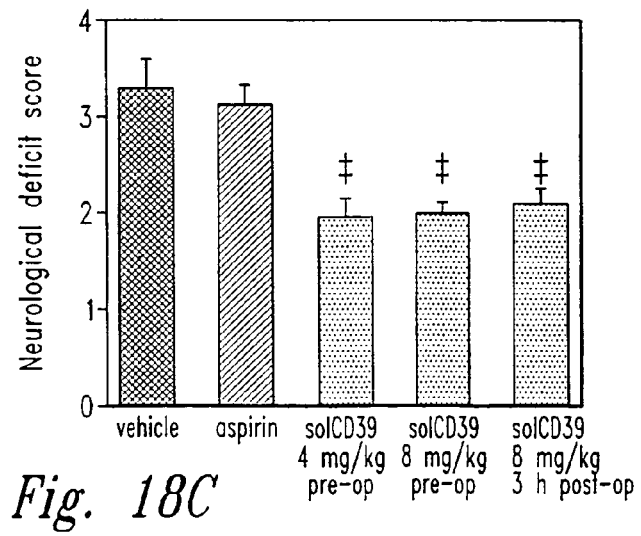
Figure 18D:
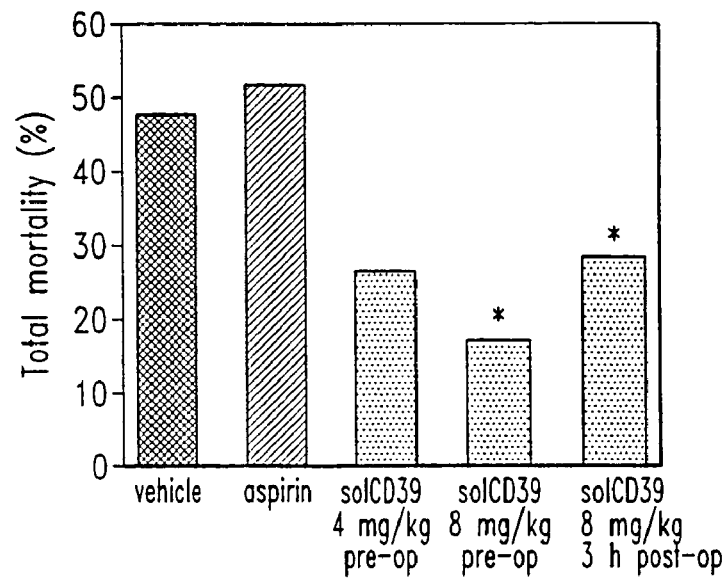

Preoperatively administered solCD39 conferred a dose-dependent diminution of cerebral infarct volume, as measured by digital histological analysis (FIG. 18B). Aspirin, in contrast, showed a tendency to decrease cerebral infarct volume, although this effect was not statistically significant. The administration of soluble CD39 either prior to, or up to 3 h following, stroke reduced both neurological deficit (FIG. 18C) and mortality (FIG. 18D).

Figure 18E:
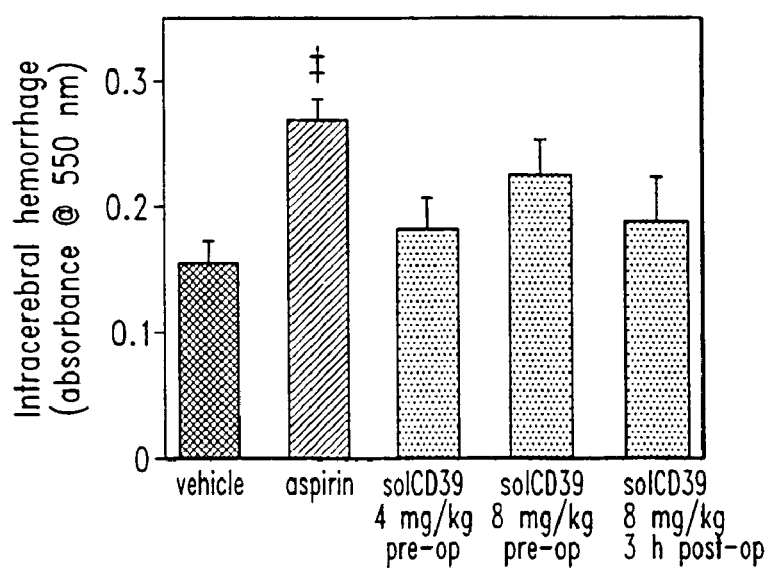
Figure 19:
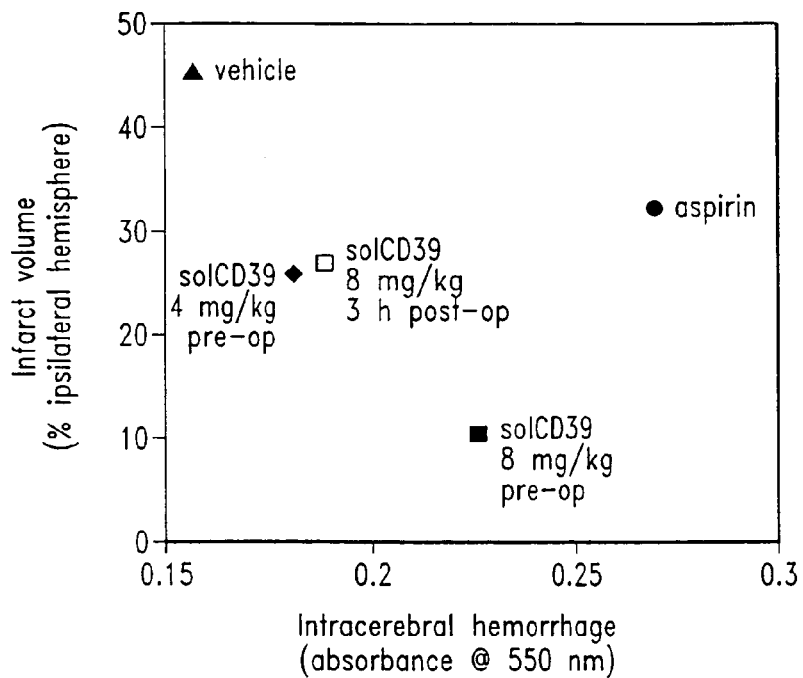
FIG. 19 shows a covariate plot of cerebral infarct volume vs. intracerebral hemorrhage. Vehicle (saline), aspirin (ASA, 5 mg/kg prior to stroke), soluble CD39 (4 & 8 mg/kg, prior to stroke), and soluble CD39 (8 mg/kg, 3 h following stroke induction in mice) are compared.

The effects of soluble CD39 and aspirin on the development of intracerebral hemorrhage following stroke are shown in FIG. 18E. Aspirin increased intracerebral hemorrhage (as measured spectrophotometrically) significantly, but there was no significant increase in intracerebral hemorrhage at any dose of soluble CD39 tested. At these doses, soluble CD39 inhibited both platelet and fibrin accumulation and promoted an increase in postischemic blood flow, as shown in FIGS. 17A, 17B, and 18A. FIG. 19 shows a covariate plot of cerebral infarct volume vs. intracerebral hemorrhage for each treatment, and indicates that aspirin is less capable of reducing infarct volume and preventing intracerebral hemorrhage than soluble CD39. In summary, at the doses tested in the mouse stroke model, solCD39 conferred protection without inducing the bleeding problems that often accompany anti-thrombotic therapy regimens.

E. CD39 Null Mice Can be Reconstituted with Soluble CD39

Figure 20A:
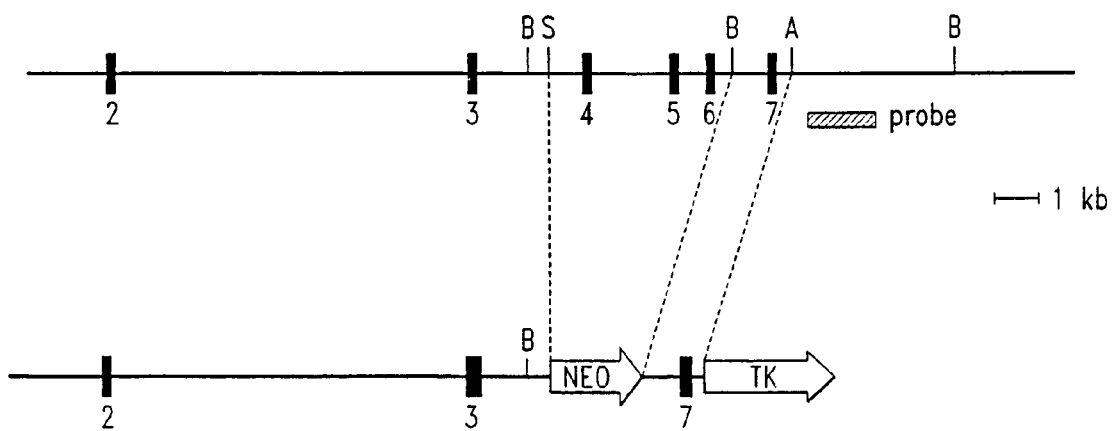
FIG. 20A shows the construct used to generate CD39−/− mice by homologous recombination. The labeled restriction sites are BglII (B), SpeI (S), and Asp718 (A).
Figure 20B:
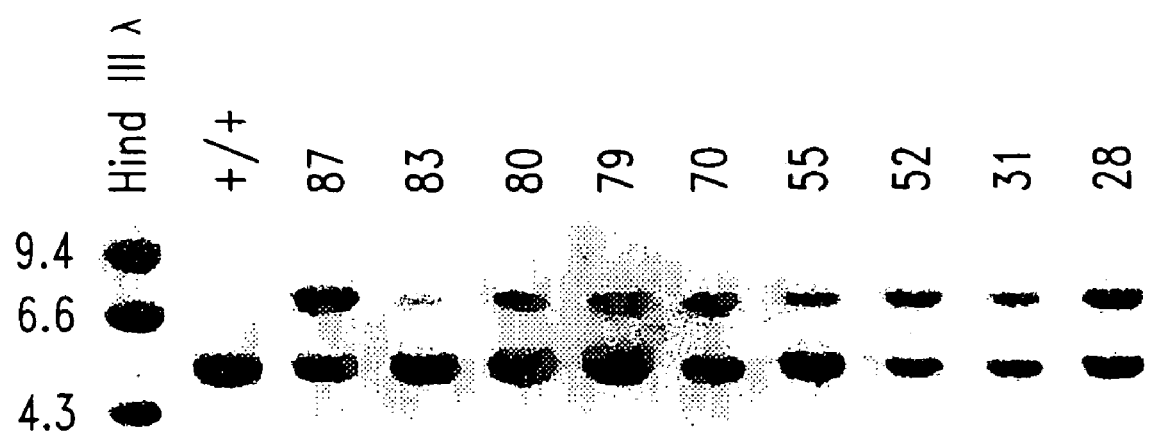
FIG. 20B shows a genomic Southern blot as used to identify ES clones having a disrupted CD39 allele.

CD39−/− mice were generated using a gene targeting vector in which exons 4-6, encoding apyrase conserved regions 2-4 (Handa, M. & Guidotti, G., *Biochem. Biophys. Res. Commun.* 218:916-923 (1996); Wang, T. F. & Guidotti, G., *J. Biol. Chem.* 271:9898-9901 (1996); Maliszewski, C. R., et al., *J. Immunol.* 153:3574-3583 (1994); and Schoenborn, M. A., et al., *Cytogen Cell Gen.* 81(3-4):287-280 (1998)), were replaced with a PGKneo cassette, as shown in FIG. 20A. The gene targeting vector, in which a 4.1 kb SpeI-BglII fragment containing exons 4-6 was replaced with a PGKneo cassette, was introduced into 129-derived ES cells. Cells were selected in G418 and gancyclovir. Nine ES clones with a disrupted CD39 allele, as identified by genomic Southern blot analyses of BglII digested DNA as shown in FIG. 20B, were injected into blastocysts and the resulting chimeras crossed to C57BL/6 to produce CD39+/− heterozygotes. CD39−/− mice were generated at the expected Mendelian frequency from CD39+/− intercrosses. The CD39−/− mice used in the experiments described below represent random C57BL/6×129 hybrids.

Figure 21:
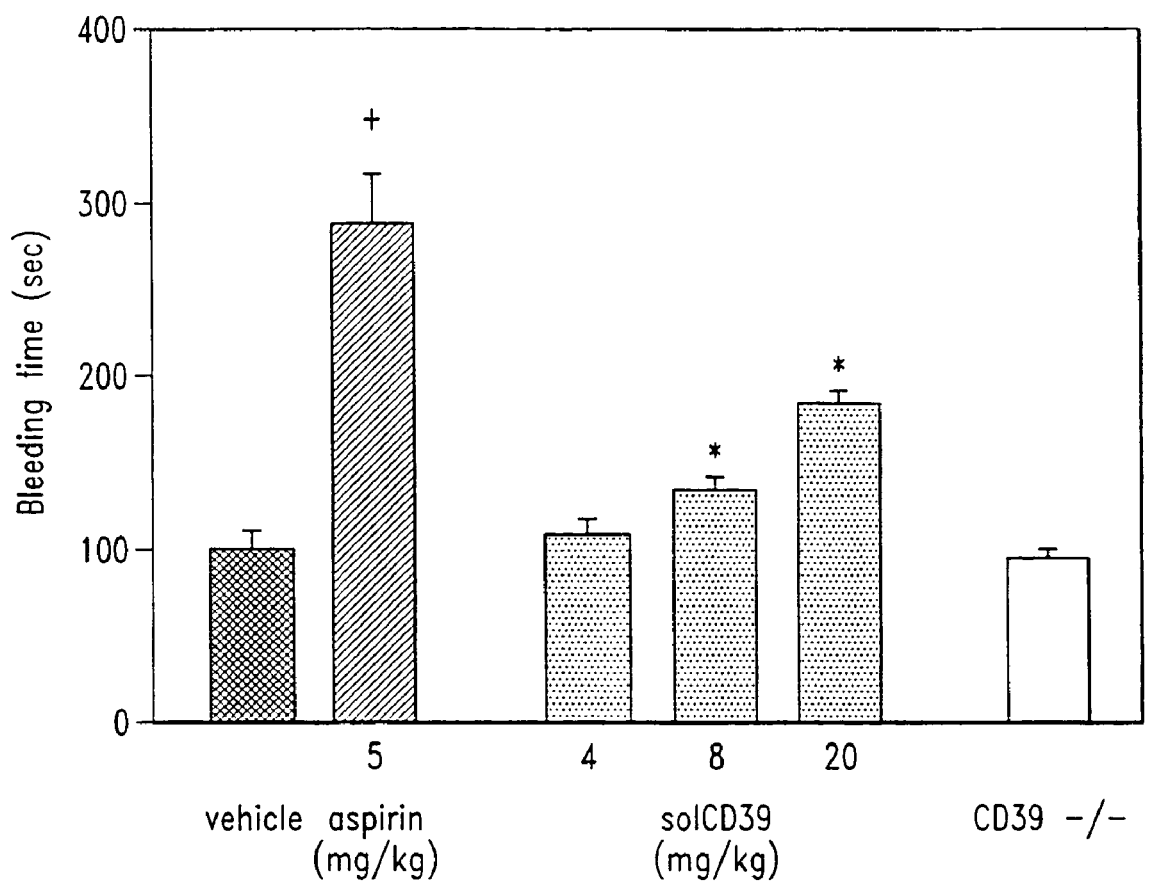
FIG. 21 shows the bleeding times in control (n=15), aspirin-treated (5 mg/kg, n=10), solCD39-treated (4, 8, and 20 mg/kg, n=25) and solCD39−/− mice (n=10). (*$p<0.05$, ‡$p<0.01$, †$p<0.001$).
Figure 22A:
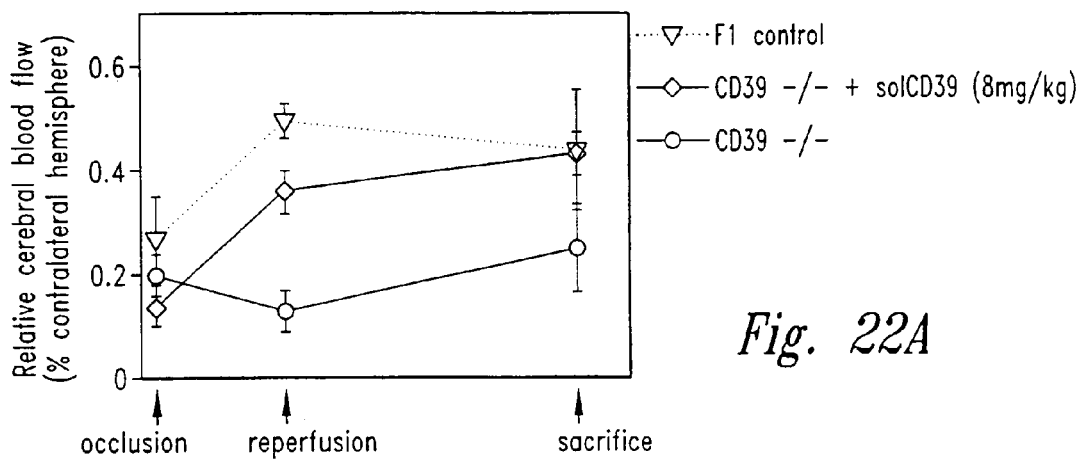
FIG. 22A shows cerebral blood flow, 22B shows cerebral infarct volume, 22C shows neurological score, 22D shows mortality, and 22E shows intracerebral hemorrhage. *$p<0.05$, ‡$p<0.01$, †$p<0.001$.
Figure 22B:
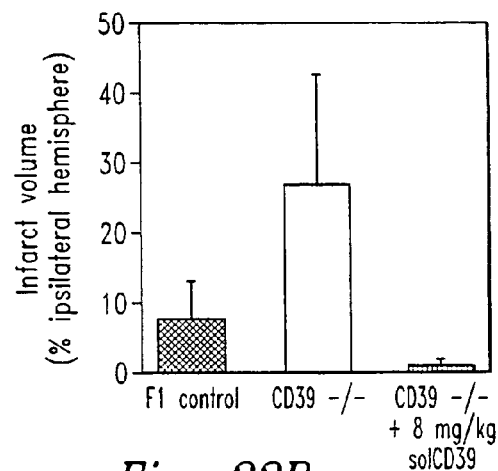
FIG. 22 shows a comparison of stroke outcomes in control (C57BL/6J×129/J F1) mice (n=6), CD39−/− mice (n=5), and CD39/− mice which were "reconstituted" with solCD39 (n=6).
Figure 22C:
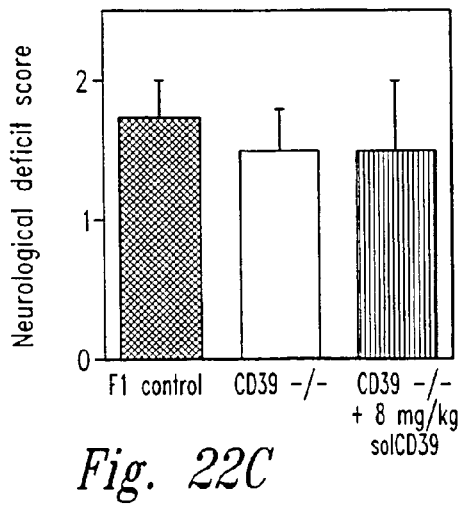
Figure 22D:
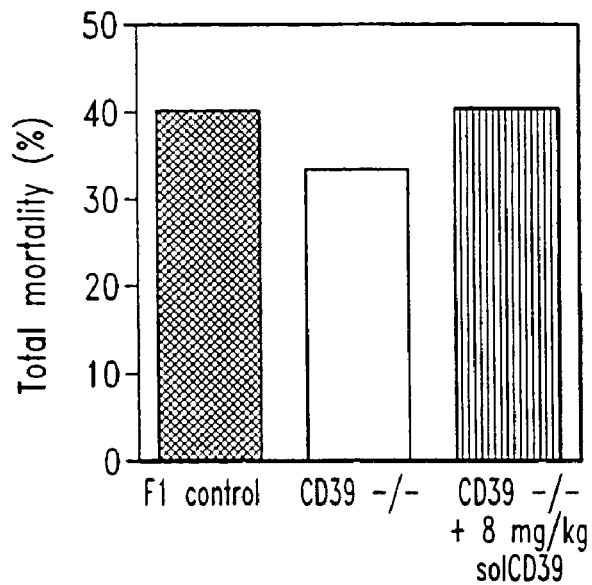
Figure 22E:
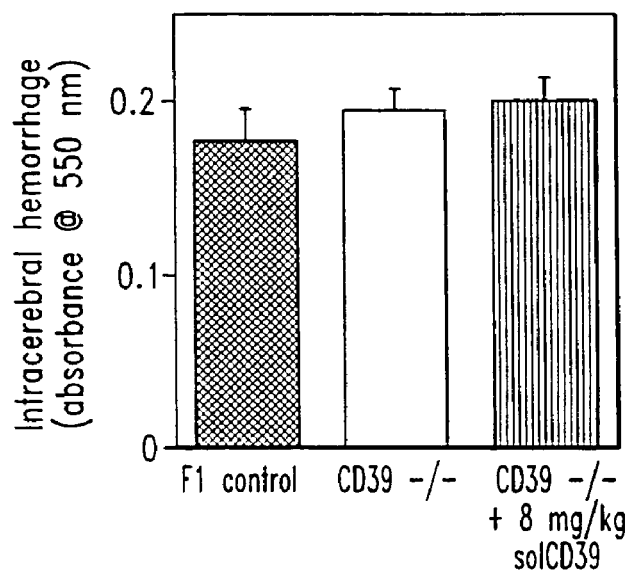

Homozygous CD39−/− mice were overtly normal, and did not display an obvious phenotype in the unperturbed state. Hematological profiles, including erythrocyte parameters, platelet counts, leukocyte counts and differentials, and coagulation screening, were normal. As shown below, the CD39-null mice did not exhibit a prothrombotic phenotype unless challenged by experimental stroke. Under those conditions, the defect was abolished and normal blood fluidity was restored by administration of soluble CD39. Bleeding times of CD39−/− mice were normal, indicating that normal blood flow in an unperturbed animal is not dependent upon endogenous expression of CD39. As is seen in normal mice, CD39−/− animals exhibited markedly increased bleeding times following the administration of aspirin or following administration of increasing doses of solCD39 as shown in FIG. 21. CD39−/− mice subjected to focal cerebral ischemia exhibited diminished blood flow following reperfusion as compared to genetically matched controls (FIG. 22A), indicating that endogenous CD39 contributes to maintenance of hemostasis during episodes of vascular injury. When solCD39 (8 mg/kg) was administered to the CD39−/− mice, these mice were "reconstituted" as shown by a postischemic blood flow similar to untreated controls. CD39−/− mice demonstrated increased cerebral infarction volume as compared to genotype-matched controls following induced stroke (FIG. 22B). CD39−/− mice "reconstituted" with solCD39 had markedly diminished infarct volume, indicating a protective effect of solCD39. Other parameters (neurological deficit scores, overall mortality, and intracerebral hemorrhage) did not differ between groups (FIG. 22 C, D, E).

These results demonstrate that CD39 inhibits microvascular thrombosis and confers cerebroprotection without inducing intracerebral hemorrhage in a murine model of stroke. Soluble CD39 decreased platelet deposition, fibrin deposition, and cerebral infarction volume. Soluble CD39 reduced infarction volume and restored postischemic blood flow even when administered three hours following stroke induction. This result is important because the average patient experiencing a stroke appears in the emergency room approximately three hours after the initial event occurs. The ability to treat patients with solCD39 after three hours provides an important advantage over many other agents designed to inhibit platelet reactivity.

Example 20

Soluble CD39 Improves Survival in a Mouse Ischemia Model

C57BL/6 mice were anesthetized and ventilated, and their thoraces were opened to surgically expose both pulmonary hila. Either physiological saline or soluble CD39 (8 mg/kg) was administered intravenously, after which the left pulmonary hilum was cross-clamped for one hour. The cross-clamp was removed for three hours of reperfusion, and then a cross-clamp was applied to the right hilum for a thirty minute observation period. This latter maneuver effectively removed the normal lung from circulation, so that the mouse must survive on the function of the post-ischemic left lung. The results are shown, in the form of a Kaplan-Meier survival plot, in FIG. 23. All of the mice given saline (n=6) died prior to the thirty minute time point whereas all of the sol39-treated mice (n=3) survived for thirty minutes.

The long lasting effects of soluble CD39 are also shown to be clinically useful in the reduction of complications of atherosclerosis, such as myocardial infarction, stroke, and peripheral vascular occlusion. Patients suffering from these conditions demonstrate an abundance of activated platelets in their circulation, and such activated platelets have a lowered threshold for ADP stimulation. Soluble CD39 metabolically deletes ADP from the fluid phase of activated platelets and reverses their prothrombotic characteristics.

The relevant disclosures of publications cited herein are specifically incorporated by reference. The examples presented above are not intended to be exhaustive or to limit the scope of the invention. The skilled artisan will understand that variations and modifications and variations are possible in light of the above teachings, and such modifications and variations are intended to be within the scope of the invention.

---

We claim:

1. A method for inhibiting platelet activation and recruitment in a mammal in need of such treatment comprising administering an effective amount of a soluble CD39 polypeptide consisting of a structure X-Y wherein X is an Ala residue or heterologous peptides selected from the group consisting of amino acids 25-39 of SEQ ID NO:11, amino acids 25-35 of SEQ ID NO:28, amino acids 27-34 of SEQ ID NO:29, and amino acids 21-24 of SEQ ID NO:30 and Y is selected from the group consisting of:
   (a) a polypeptide consisting of amino acids 36-478 of SEQ ID NO:2;
   (b) a fragment of the polypeptide of (a) consisting of consecutive amino acids of (a) wherein said fragment has apyrase activity;
   (c) a variant polypeptide that is at least 95% identical in amino acid sequence to (a) or (b) wherein said variant polypeptide has apyrase activity; and
   (d) a substituted polypeptide consisting of the amino acids of (a), (b), or (c) with at least one conservative amino acid substitution wherein said substituted polypeptide has apyrase activity.

2. The method of claim 1 wherein Y is a polypeptide consisting of amino acids 38-476 or 39-476 of SEQ ID NO:2.

3. The method of claim 1 wherein X is selected from the group consisting of:
   (a) amino acids 25-39 of SEQ ID NO:11, amino acids 25-35 of SEQ ID NO:28, amino acids 27-34 of SEQ ID NO:29, and amino acids 21-24 of SEQ ID NO:30;
   (b) a fragment consisting of consecutive amino acids of any of the amino acid sequences of (a) wherein said X-Y polypeptide has apyrase activity; and
   (c) a substituted polypeptide consisting of the amino acids of (a) or (b) with at least one conservative amino acid substitution wherein said X-Y polypeptide has apyrase activity.

4. A method of inhibiting platelet activation and recruitment in a mammal in need of such treatment comprising administering an effective amount of a soluble CD39 polypeptide selected from the group consisting of: SEQ ID NO: 6, amino acids 25-464 of SEQ ID NO:27, amino acids 25-474 of SEQ ID NO:28, amino acids 27-473 of SEQ ID NO:29 and amino acids 21-463 of SEQ ID NO:30.

5. The method of claim 4 wherein the soluble CD39 polypeptide consists of the sequence of amino acids 21-463 of SEQ ID NO: 30.

6. The method according to claim 1 wherein the soluble CD39 polypeptide has been produced by culturing a recombinant cell that expresses the soluble CD39 polypeptide under conditions permitting expression of the CD39 polypeptide, and recovering the expressed CD39 polypeptide.

7. The method according to claim 4 wherein the soluble CD39 polypeptide has been produced by culturing a recombinant cell that expresses the soluble CD39 polypeptide under conditions permitting expression of the CD39 polypeptide, and recovering the expressed CD39 polypeptide.

8. The method of claim 6 wherein the recombinant cell comprises a nucleic acid having a sequence selected from the group consisting of:
   (a) SEQ ID NO:5; and
   (b) DNA sequences which, due to degeneracy of the genetic code, encode the polypeptide encoded by SEQ ID NO:5.

9. The method of claim 7 wherein the recombinant cell comprises a nucleic acid having a sequence selected from the group consisting of:
   (a) SEQ ID NO:5; and
   (b) DNA sequences which, due to degeneracy of the genetic code, encode the polypeptide encoded by SEQ ID NO:5.

10. The method of claim 6 wherein the recombinant cell comprises a nucleic acid having a sequence selected from the group consisting of:
 (a) SEQ ID NO:7; and
 (b) DNA sequences which, due to degeneracy of the genetic code, encode the polypeptide encoded by SEQ ID NO:7.

11. The method of claim 7 wherein the recombinant cell comprises a nucleic acid having a sequence selected from the group consisting of:
 (a) SEQ ID NO:7; and
 (b) DNA sequences which, due to degeneracy of the genetic code, encode the polypeptide encoded by SEQ ID NO:7.

12. The method of claim 1 wherein the soluble CD39 polypeptide is administered in a composition comprising a pharmaceutically acceptable carrier.

13. The method of claim 4 wherein the soluble CD39 polypeptide is administered in a composition comprising a pharmaceutically acceptable carrier.

14. The method of claim 1 wherein the soluble CD39 polypeptide is administered in combination with at least one other antithrombotic or antiplatelet composition.

15. The method of claim 4 wherein the soluble CD39 polypeptide is administered in combination with at least one other antithrombotic or antiplatelet composition.

16. The method of claim 1 wherein the soluble CD39 polypeptide is administered in combination with aspirin.

17. The method of claim 4 wherein the soluble CD39 polypeptide is administered in combination with aspirin.

18. The method of claim 1 wherein the soluble CD39 polypeptide is administered parenterally.

19. The method of claim 4 wherein the soluble CD39 polypeptide is administered parenterally.

20. The method of claim 1 wherein the soluble CD39 polypeptide is administered intravenously.

21. The method of claim 4 wherein the soluble CD39 polypeptide is administered intravenously.

22. The method of claim 1 wherein the mammal is suffering from unstable angina, myocardial infarction, stroke, coronary artery disease or injury, myocardial infarction, atherosclerosis, peripheral vascular occlusion, preeclampsia, embolism, a platelet-associated ischemic disorder including lung ischemia, coronary ischemia, and cerebral ischemia, a thrombotic disorder including coronary artery thrombosis, cerebral artery thrombosis, intracardiac thrombosis, peripheral artery thrombosis, venous thrombosis, thrombosis and coagulopathy associated with exposure to a foreign or injured tissue surface, deep venous thrombosis (DVT), pulmonary embolism (PE), transient ischemic attack (TIAs), or another related condition where vascular occlusion is the common underlying feature.

23. The method of claim 4 wherein the mammal is suffering from unstable angina, myocardial infarction, stroke, coronary artery disease or injury, myocardial infarction, atherosclerosis, peripheral vascular occlusion, preeclampsia, embolism, a platelet-associated ischemic disorder including lung ischemia, coronary ischemia, and cerebral ischemia, a thrombotic disorder including coronary artery thrombosis, cerebral artery thrombosis, intracardiac thrombosis, peripheral artery thrombosis, venous thrombosis, thrombosis and coagulopathy associated with exposure to a foreign or injured tissue surface, deep venous thrombosis (DVT), pulmonary embolism (PE), transient ischemic attack (TIAs), or another related condition where vascular occlusion is the common underlying feature.

24. The method of claim 1 wherein the soluble CD39 is administered to inhibit thrombus formation or reformation, occlusion, reocclusion, stenosis, or restenosis of blood vessels, or stroke.

25. The method of claim 4 wherein the soluble CD39 is administered to inhibit thrombus formation or reformation, occlusion, reocclusion, stenosis, or restenosis of blood vessels, or stroke.

26. The method of claim 1 wherein the soluble CD39 is administered in conjunction with angioplasty, carotid endarterectomy, anastomosis of vascular graft, atherectomy, stent placement, placement of a chronic cardiovascular device such as an in-dwelling catheter or prosthetic valve or vessel, or bypass surgery.

27. The method of claim 4 wherein the soluble CD39 is administered in conjunction with angioplasty, carotid endarterectomy, anastomosis of vascular graft, atherectomy, stent placement, placement of a chronic cardiovascular device such as an in-dwelling catheter or prosthetic valve or vessel, or bypass surgery.

\* \* \* \* \*